(12) United States Patent
Ennishi et al.

(10) Patent No.: US 11,692,228 B2
(45) Date of Patent: Jul. 4, 2023

(54) GENE EXPRESSION PROFILES FOR B-CELL LYMPHOMA AND USES THEREOF

(71) Applicant: Provincial Health Services Authority, Vancouver (CA)

(72) Inventors: Daisuke Ennishi, Okayama (JP); Aixiang Jiang, Vancouver (CA); Ryan Morin, Maple Ridge (CA); David Scott, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 0 days.

(21) Appl. No.: 17/285,665

(22) PCT Filed: Oct. 15, 2019

(86) PCT No.: PCT/IB2019/058784
§ 371 (c)(1),
(2) Date: Apr. 15, 2021

(87) PCT Pub. No.: WO2020/079591
PCT Pub. Date: Apr. 23, 2020

(65) Prior Publication Data
US 2022/0002814 A1    Jan. 6, 2022

Related U.S. Application Data

(60) Provisional application No. 62/745,556, filed on Oct. 15, 2018.

(51) Int. Cl.
*C12Q 1/6886*    (2018.01)
(52) U.S. Cl.
CPC ..... *C12Q 1/6886* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2009/0226905 A1* 9/2009 Joubert ............ G01N 33/57419
435/6.12
2017/0029904 A1* 2/2017 Rodig .................. A61K 31/704

FOREIGN PATENT DOCUMENTS

WO    WO 2015/069790    * 11/2014

OTHER PUBLICATIONS

Tuttle et al PLoS ONE. Jan. 2014. 9: e87325 (Year: 2014).*
Chen et al Molecular & Cellular Proteomics. 2002. 1: 304-313 (Year: 2002).*
Vogel et al Nature Review Genet. Mar. 2012. 13(4): 227-232 (Year: 2012).*
Min et al BMC Genomics. 2010. 11:96 (Year: 2010).*
Hanke et al. Clinical Chemistry. 2007. 53: 2070-2077 (Year: 2007).*
Palmer BMC Genomics. 2006. 7:115 (Year: 2006).*
Xu-Monette et al Modern Pathology. 2015. 28:1555-1573 (Year: 2015).*
Ennishi et al. J Clin Oncol. 37: 190-201, published online Dec. 3, 2018, p. 190-201 and Appendix, 27 pages total; and Supplementary Methods, 13 pages and Table 10A (Year: 2018).*
Schmitz R, Wright GW, Huang DW, et al: Genetics and pathogenesis of diffuse large B-cell lymphoma. N Engl J Med 378:1396-1407, 2018.
Ennishi, D. et al., "Double-Hit Gene Expression Signature Defines a Distinct Subgroup of Germinal Center B-Cell-Like Diffuse Large B-Cell Lymphoma". J Clin Oncol, Jan. 20, 2019, vol. 37(3), pp. 190-201, (whole document).
Lenz G, Wright G, Dave SS, et al: Stromal gene signatures in large-B-cell lymphomas. N Engl J Med 359:2313-23, 2008.
Shipp MA, Ross KN, Tamayo P, et al: Diffuse large B-cell lymphoma outcome prediction by gene-expression profiling and supervised machine learning. Nat Med 8:68-74, 2002.
Alizadeh AA, Eisen MB, Davis RE, et al: Distinct types of diffuse large B-cell lymphoma identified by gene expression profiling. Nature 403:503-11, 2000.
Swerdlow SH, Campo E, Pileri SA, et al: The 2016 revision of the World Health Organization (WHO) classification of lymphoid neoplasms. Blood 127:2375-2390, 2016.
Scott DW, King RL, Staiger AM, et al: High-grade B-cell lymphoma with MYC and BCL2 and/or BCL6 rearrangements with diffuse large B-cell lymphoma morphology. Blood 131:2060-2064, 2018.
Ennishi D, Mottok A, Ben-Neriah S, et al: Genetic profiling of MYC and BCL2 in diffuse large B-cell lymphoma determines cell-of-origin-specific clinical impact. Blood 129:2760-2770, 2017.
Ott G, Rosenwald A, Campo E: Understanding MYC-driven aggressive B-cell lymphomas: pathogenesis and classification. Hematology 575-583, 2013.
Sarkozy C, Traverse-Glehen A, Coiffier B: Double-hit and double-protein-expression lymphomas: aggressive and refractory lymphomas. Lancet Oncol 16:e555-e567, 2015.
Johnson NA, Slack GW, Savage KJ, et al: Concurrent expression of MYC and BCL2 in diffuse large B-cell lymphoma treated with rituximab plus cyclophosphamide, doxorubicin, vincristine, and prednisone. J Clin Oncol 30:3452¬3459, 2012.
Green TM, Young KH, Visco C, et al: Immunohistochemical double-hit score is a strong predictor of outcome in patients with diffuse large B-cell lymphoma treated with rituximab plus cyclophosphamide, doxorubicin, vincristine, and prednisone. J Clin Oncol 30:3460-3467, 2012.

(Continued)

*Primary Examiner* — Carla J Myers
(74) *Attorney, Agent, or Firm* — Oven Wiggs Green & Mutala LLP

(57) ABSTRACT

The present invention relates to gene expression profiles for B-cell lymphoma. More specifically, the present invention relates to gene expression profiles for diagnosis, prognosis or therapy selection for an aggressive B-cell lymphoma.

17 Claims, 21 Drawing Sheets

Specification includes a Sequence Listing.

(56) References Cited

OTHER PUBLICATIONS

Johnson NA, Savage KJ, Ludkovski 0, et al: Lymphomas with concurrent BCL2 and MYC translocations: the critical factors associated with survival. Blood 114:2273-2279, 2009.
Savage KJ, Johnson N a, Ben-neriah S, et al: MYC gene rearrangements are associated with a poor prognosis in diffuse large B-cell lymphoma patients treated with R-CHOP chemotherapy. Blood 114:3533-3537, 2009.
Pasqualucci L, Trifonov V, Fabbri G, et al: Analysis of the coding genome of diffuse large B-cell lymphoma. Nat Genet 43:830-7, 2011.
Morin RD, Mendez-Lago M, Mungall AJ, et al: Frequent mutation of histone-modifying genes in non-Hodgkin lymphoma. Nature 476:298-303, 2011.
Morin RD, Mungall K, Pleasance E, et al: Mutational and. structural analysis of diffuse large B-cell lymphoma using whole-genome sequencing. Blood 122:1256-65, 2013.
Lohr JG, Stojanov P, Lawrence MS, et al: Discovery and prioritization of somatic mutations in diffuse large B-cell lymphoma (DLBCL) by whole-exome sequencing. Proc Natl Acad Sci U S A 109:3879-3884, 2012.
Chapuy B, Stewart C, Dunford AJ, et al: Molecular subtypes of diffuse large B cell lymphoma are associated with distinct pathogenic mechanisms and outcomes. Nat Med 24:679-690, 2018.
Reddy A, Zhang J, Davis NS, et al: Genetic and functional drivers of diffuse large B cell lymphoma. Cell 171:481-494. e15, 2017.
Kridel R, Mottok A, Farinha P, et al: Cell-of-origin of transformed follicular lymphoma. Blood 126:2118-2127, 2015.
Arthur S, Jiang A, Grande B, et al: Genome-wide discovery of somatic coding and regulatory variants in Diffuse Large B-cell Lymphoma. Nat Commun 9: 4001, 2018.
Drtega-Molina A, Boss IW, Canela A, et al: The histone lysine methyltransferase KMT2D sustains a gene expression program that represses B cell lymphoma development. Nat Med 21:1199-1208, 2015.
Jiang Y, Ortega-Molina A, Geng H, et al: CREBBP Inactivation Promotes the Development of HDAC3-Dependent Lymphomas. Cancer Discov 7:38¬53, 2017.
Scott DW, Mottok A, Ennishi D, et al: Prognostic significance of diffuse large B-cell lymphoma cell of origin determined by digital gene expression in formalin-fixed paraffin-embedded tissue biopsies. J Clin Oncol 33:2848-2856, 2015.
Victora GD, Dominguez-Sola D, Holmes AB, et al: Identification of human germinal center light and dark zone cells anti their relationship to human B-cell lymphomas. Blood 120:2240-8, 2012.
Milpied P, Cervera-Marzal I, Mollichella M-L, et al: Human germinal center transcriptional programs are de-synchronized in B cell lymphoma. Nat Immunol 19:1013-1024, 2018.
Mottok A, Wright G, Rosenwald A, et al: Molecular classification of primary mediastinal large B-cell lymphoma using routinely available tissue specimens. Blood 132:2401-2405, epub Sep. 26, 2018.
Dominguez-Sola D, Victora GD, Ying CY, et al: The proto-oncogene MYC is required for selection in the germinal center and cyclic reentry. Nat Immunol 13:1083-1091, 2012.
Calado DP, Sasaki Y, Godinho SA, et al: The cell-cycle regulator c-Myc is essential for the formation and maintenance of germinal centers. Nat Immunol 13:1092-1100, 2012.
Green MR, Kihira S, Liu CL, et al: Mutations in early follicular lymphoma progenitors are associated with suppressed antigen presentation. Proc Natl Acad Sci USA 112:E1116-25, 2015.
Davids MS, Roberts AW, Seymour .1F, et al: Phase i first-in-human study of venetoclax in patients with relapsed or refractory non-Hodgkin lymphoma. J Clin Oncol 35:826-833, 2017.
Scott DW, Wright GW, Williams PM, et al: Determining cell-of-origin subtypes of diffuse large B-cell lymphoma using gene expression in formalin-fixed paraffin-embedded tissue. Blood 123:1214-1217, 2014.
Cancer Genome Atlas Research Network: Comprehensive molecular characterization of gastric adenocarcinoma. Nature 513:202-9, 2014.
Love MI, Huber W, Anders S: Moderated estimation of fold change and dispersion for RNA-seq data with DESeq2. Genome Biol 15:550, 2014.
Sergushichev A: An algorithm for fast preranked gene set enrichment analysis using cumulative statistic calculation. bioRxiv 60012, 2016.
R. Schmitz, G. W. Wright et al., "Genetics and Pathogenesis of Diffuse Large B-Cell Lymphoma", The New England Journal of Medicine, 378: 1396-407. Apr. 12, 2018.
D. Ennishi, Phd. et al., "Double-Hit Gene Expression Signature Defines a Distinct Subgroup of Germinal Center B-Cell-Like Diffuse Large B-Cell Lymphoma", Journal of Clinical Oncology, vol. 37(3), pp. 190-201. Jan. 20, 2019.
Mockler et al., "Applications of DNA tiling arrays for whole-genome analysis", Genomics, 85(1):1-15, Jan. 1, 2005.
Ye et al., "Prognostic impact of concurrent MYC and BCL6 rearrangements and expression in de novo diffuse large B-cell lymphoma", Oncotarget, 7(3):2401-2416, Jan. 19, 2016.
Merron et al., "Double hit lymphoma: How do we define it and how do we treat it?", Best Practice & Research Clinical Haematology, 31(3):233-240, Jul. 26, 2018.
Daisuke Ennishi et al. "The Double-Hit Gene Expression Signature Defines a Clinically and Biologically Distinct Subgroup within GCB-DLBCL", Blood (2018) 132 (Suppl_1):921, http://doi.org/10.1182/blood-2018-99-116827. Nov. 29, 2018.

* cited by examiner

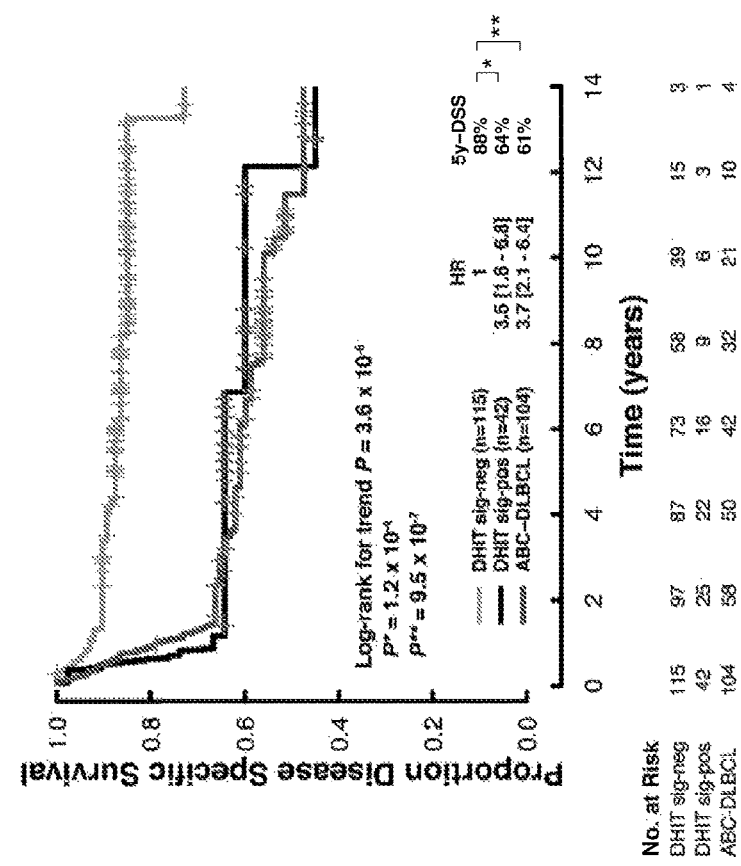
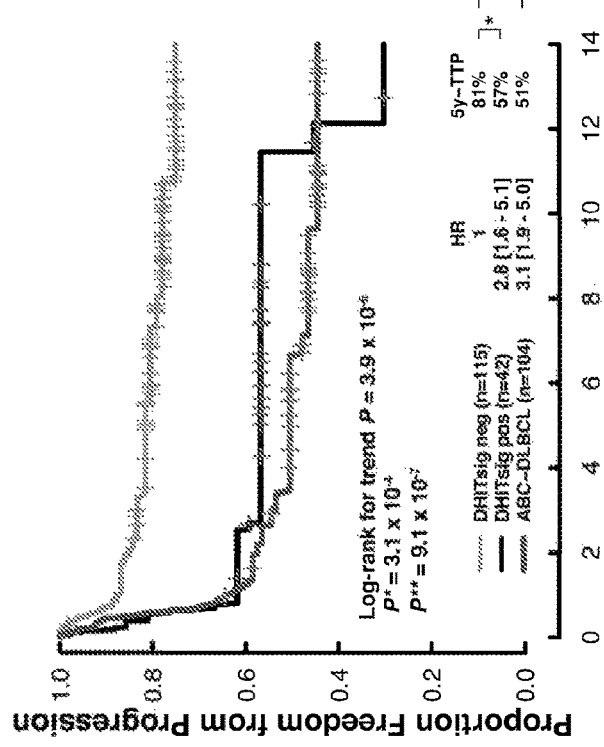
FIGURE 6 (A and B)

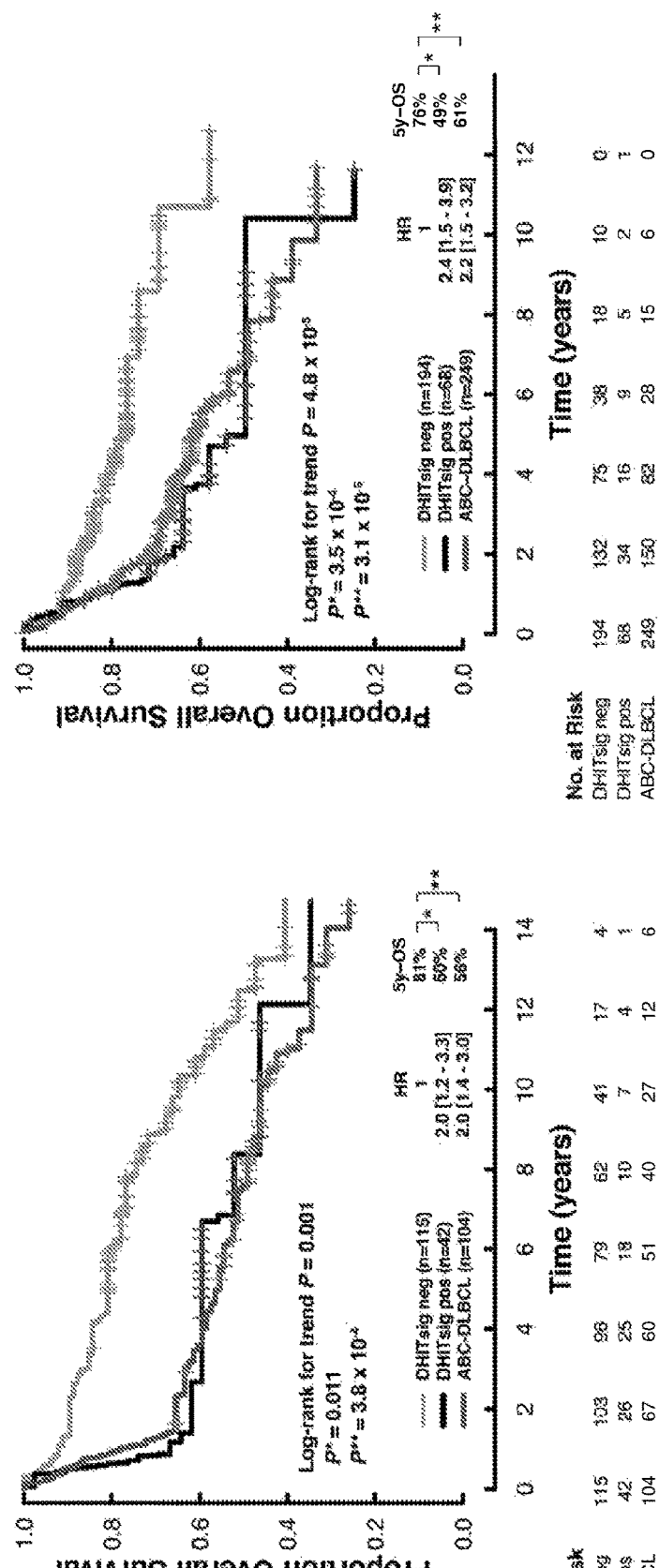
FIGURE 6 (C and D)

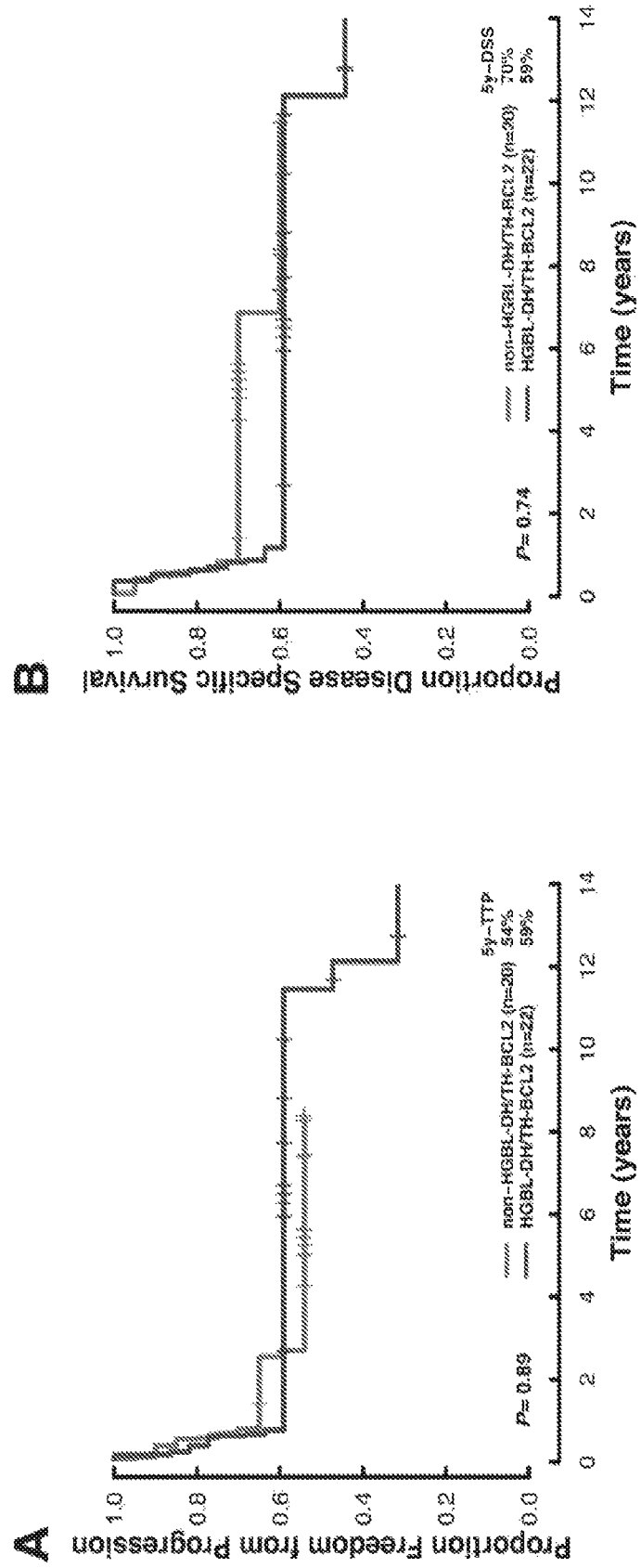
FIGURE 7 (A and B)

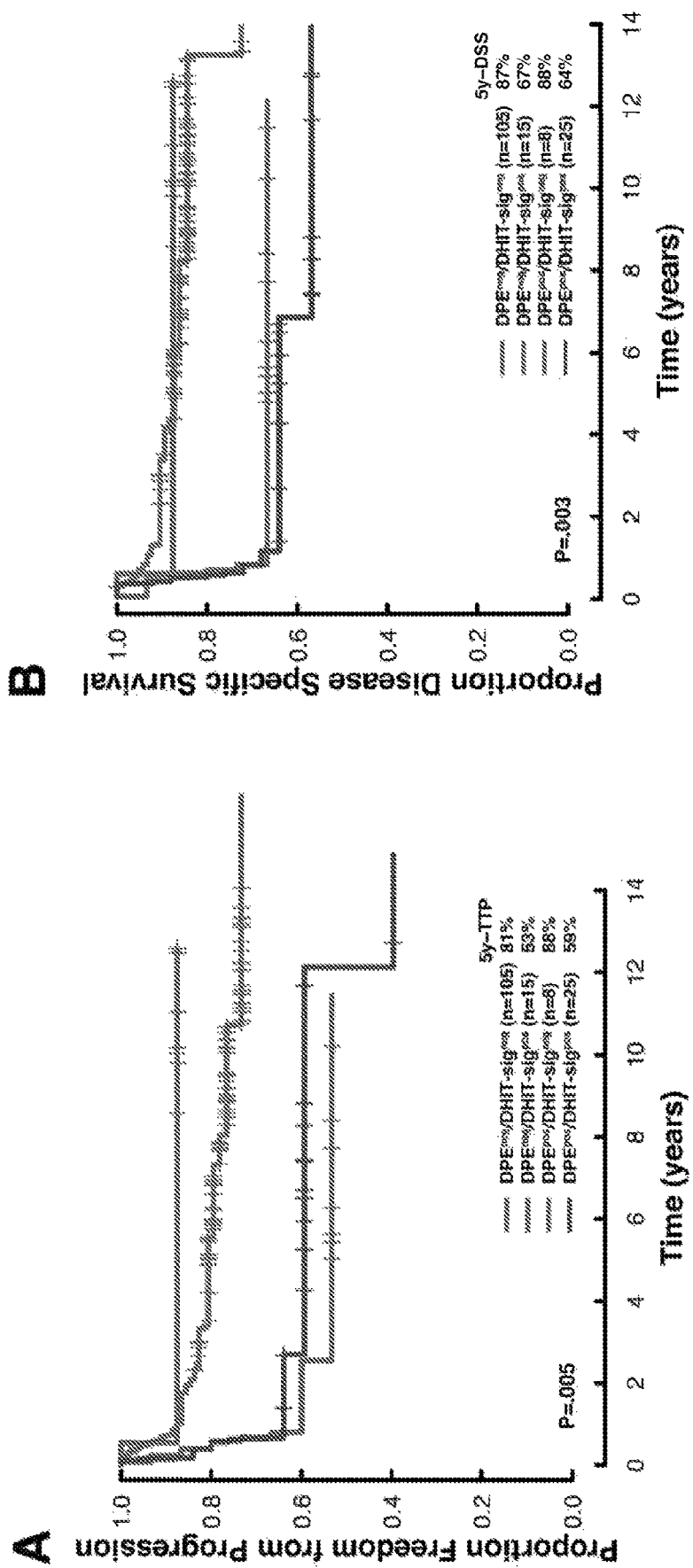
FIGURE 8 (A and B)

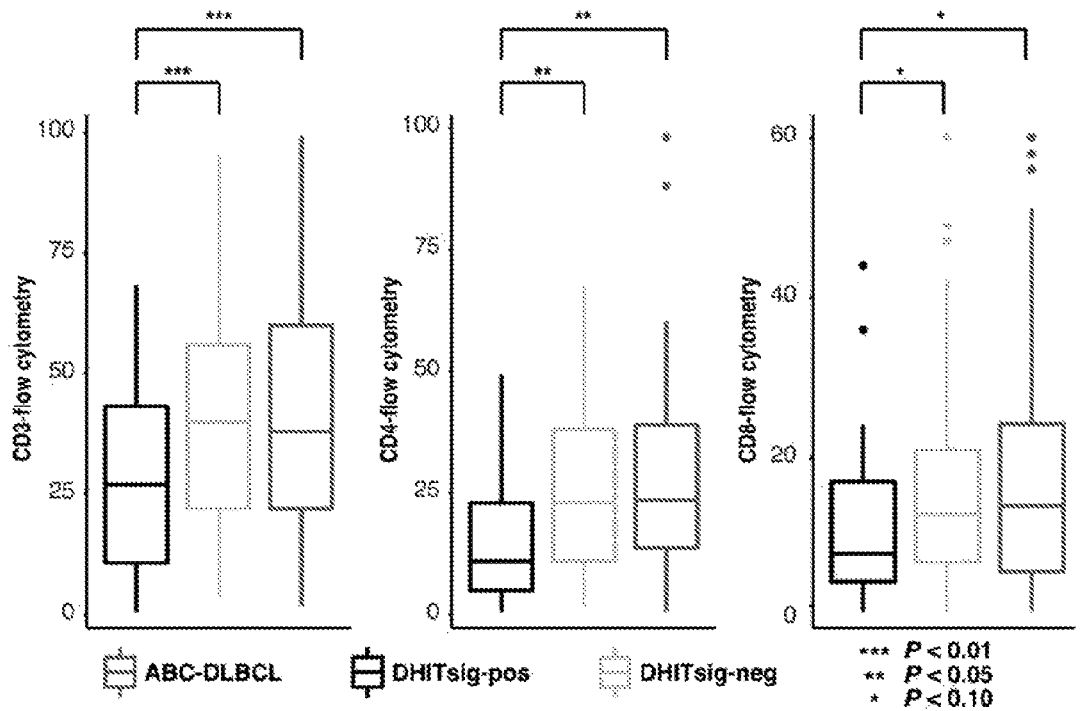
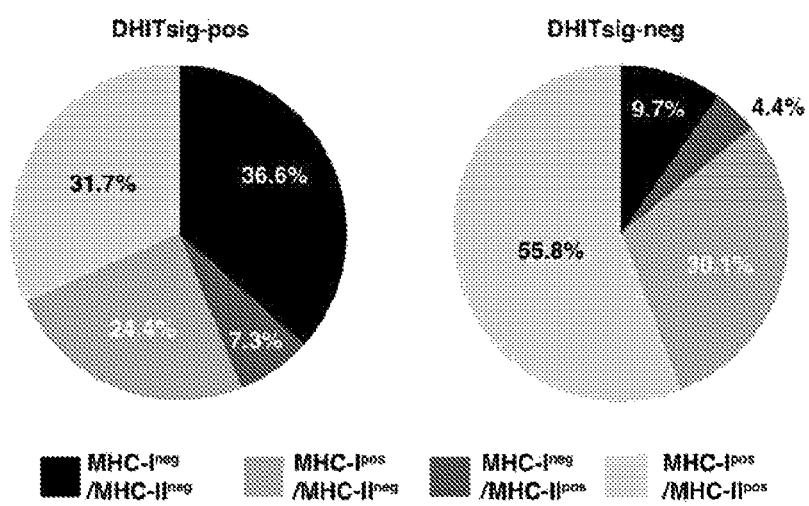
FIGURE 11 (A and B)

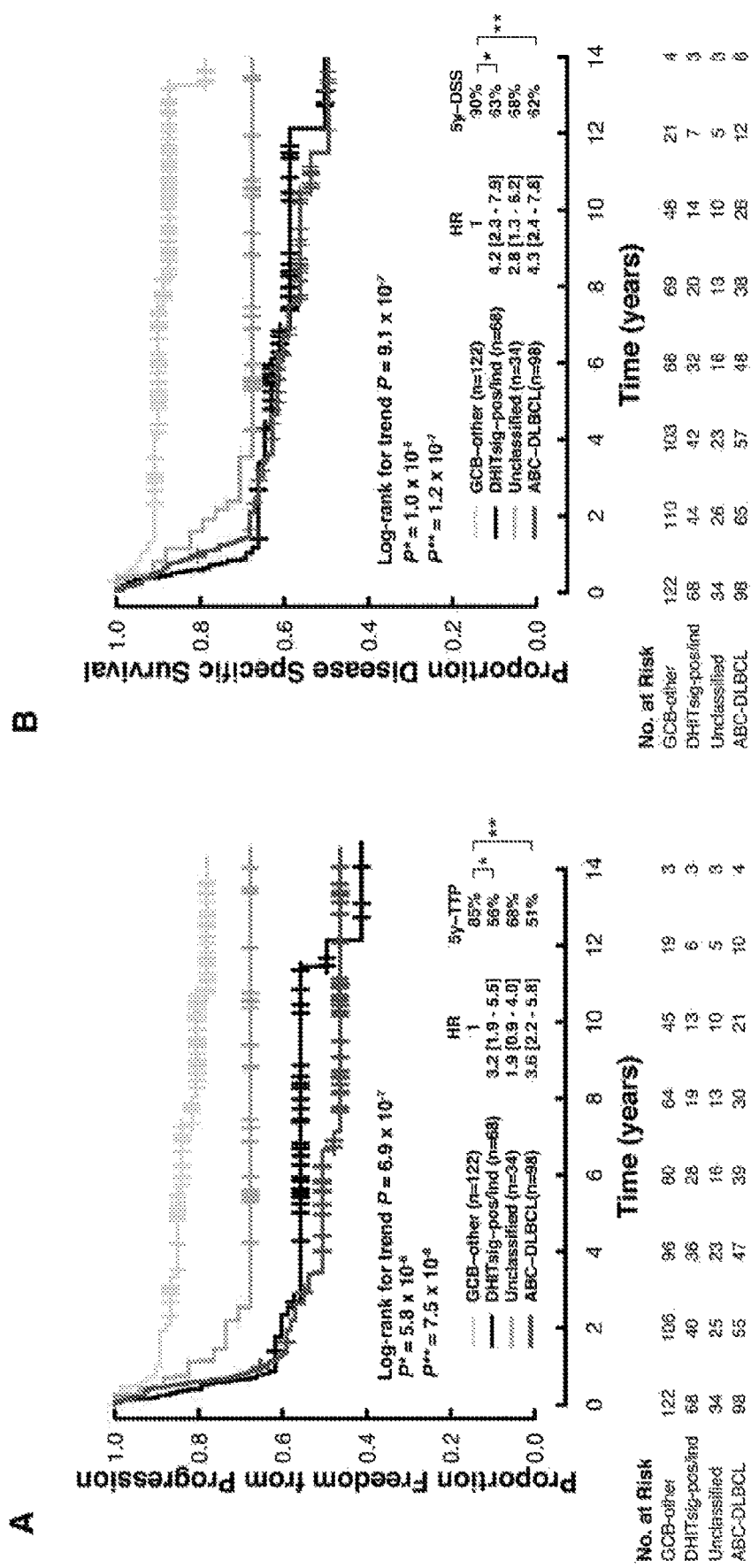
FIGURE 15 (A and B)

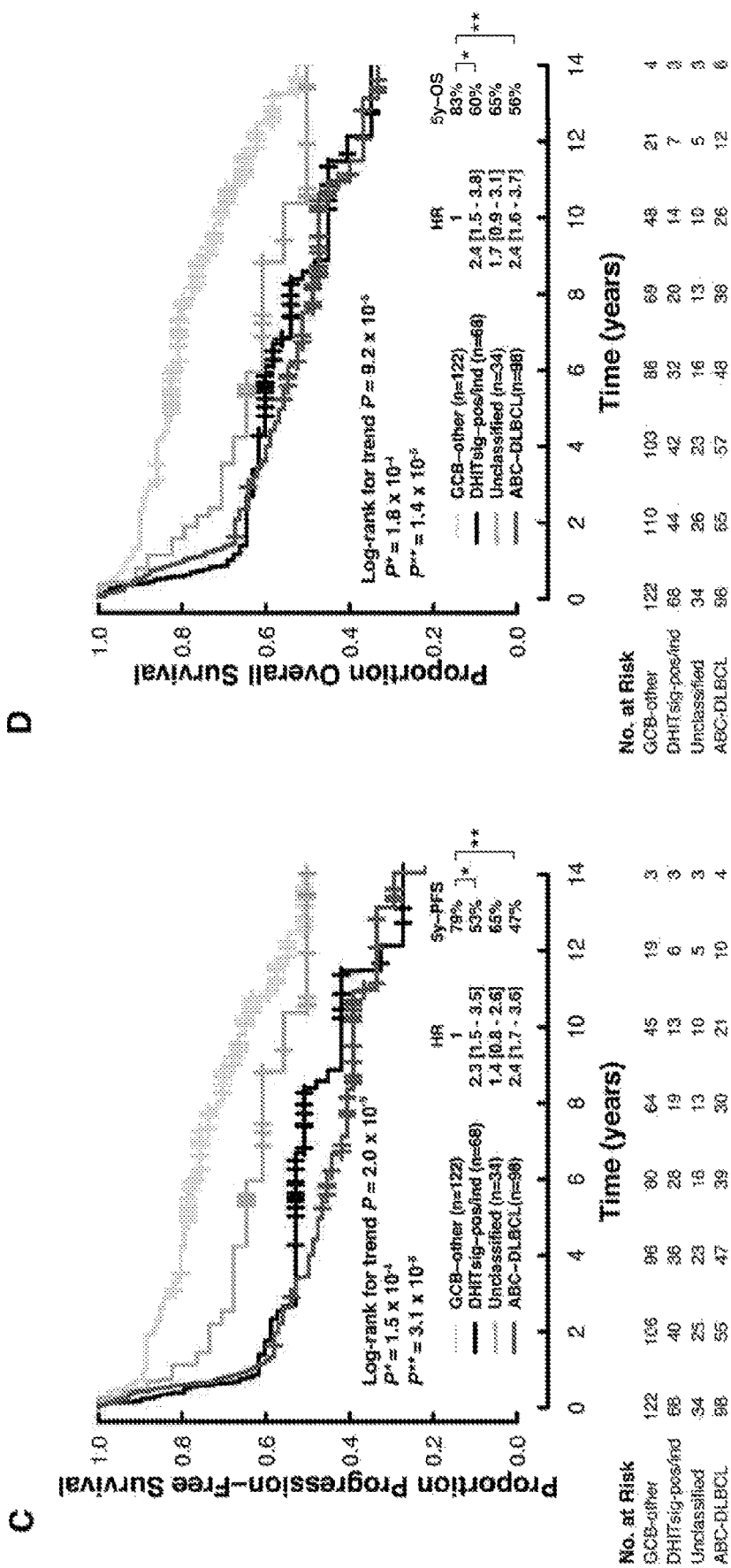
FIGURE 15 (C and D)

SEQUENCE LISTING

```
<160> NUMBER OF SEQ ID NOS: 90

<210> SEQ ID NO 1
<211> LENGTH: 100
<212> TYPE: DNA
<213> ORGANISM: Artificial Sequence
<220> FEATURE:
<223> OTHER INFORMATION: Probe

<400> SEQUENCE: 1
agtggaaagc ctcatttgaa gagctccacg atgtggacca ctttgaaatt gttgagaatc      60
tgacccagaa ggacaacgtg ctcacccaga ttatcttgaa                           100

<210> SEQ ID NO 2
<211> LENGTH: 100
<212> TYPE: DNA
<213> ORGANISM: Artificial Sequence
<220> FEATURE:
<223> OTHER INFORMATION: Probe

<400> SEQUENCE: 2
gtcaagatca gcaacactat ttctgagcgg gtcatgaatc actggcagga agacctgatg      60
tttggctacc agttcctgaa tggctgcaac cctgtgttga                           100

<210> SEQ ID NO 3
<211> LENGTH: 100
<212> TYPE: DNA
<213> ORGANISM: Artificial Sequence
<220> FEATURE:
<223> OTHER INFORMATION: Probe

<400> SEQUENCE: 3
cactgtgggt tgcaggccca atgcagaaga gtattaagaa agatgctcaa gtcccatggc      60
```
acagagcaag gcgggcaggg aacggttatt tttctaaata    100

<210> SEQ ID NO 4
<211> LENGTH: 100
<212> TYPE: DNA
<213> ORGANISM: Artificial Sequence
<220> FEATURE:
<223> OTHER INFORMATION: Probe

<400> SEQUENCE: 4
atagacactc cccgaagtct tttgttcgca tggtcacaca ctgatgctta gatgttccag    60
taatctaata tggccacagt agtcttgatg accaaagtcc    100

<210> SEQ ID NO 5
<211> LENGTH: 100
<212> TYPE: DNA
<213> ORGANISM: Artificial Sequence
<220> FEATURE:
<223> OTHER INFORMATION: Probe

<400> SEQUENCE: 5
gatatcacta ataacctctc cattgtgatc ctggctctgc gcccatctga cgagggcaca    60
tacgagtgtg ttgttctgaa gtatgaaaaa gacgctttca    100

<210> SEQ ID NO 6
<211> LENGTH: 100
<212> TYPE: DNA
<213> ORGANISM: Artificial Sequence
<220> FEATURE:
<223> OTHER INFORMATION: Probe

<400> SEQUENCE: 6
tttgtgtaca gtatgtgtct agcaaagcca ccaagggcct cacctttccc acagtctctc    60
cctggggttt ttttcatccc tgccaagaac tctgggcact    100

<210> SEQ ID NO 7
<211> LENGTH: 100
<212> TYPE: DNA
<213> ORGANISM: Artificial Sequence
<220> FEATURE:
<223> OTHER INFORMATION: Probe

<400> SEQUENCE: 7
ccgggcaacc tcagatgacc gacttttccc tttgagcctc agtttctcta gctgagaaat    60
ggagatgtac tactctctcc tttacctttta cctttaccac    100

<210> SEQ ID NO 8
<211> LENGTH: 100
<212> TYPE: DNA
<213> ORGANISM: Artificial Sequence
<220> FEATURE:
<223> OTHER INFORMATION: Probe

<400> SEQUENCE: 8
gccatcgcag cgtcaaaggt gcaggaggcg cccattgatg agcattggat catcgagtgc    60
aatgacggcg tcttccagcg gctccgggac tgggccccac    100

<210> SEQ ID NO 9
<211> LENGTH: 100
<212> TYPE: DNA
<213> ORGANISM: Artificial Sequence
<220> FEATURE:
<223> OTHER INFORMATION: Probe

<400> SEQUENCE: 9

```
taatgacacg ctcttcgtgc tgtgtgccgt ctctctctcc atctgtctct acaaaatctc    60
taagatgtcc ttagccaaca tttacttgga gtccaagggc                         100
```

<210> SEQ ID NO 10
<211> LENGTH: 100
<212> TYPE: DNA
<213> ORGANISM: Artificial Sequence
<220> FEATURE:
<223> OTHER INFORMATION: Probe

<400> SEQUENCE: 10

```
cgtgtttgtg gtcaacagat gacaacagcc gtcctccctc ctagggtctt gtgttgcaag    60
ttggtccaca gcatctccgg ggctttgtgg gatcagggca                         100
```

<210> SEQ ID NO 11
<211> LENGTH: 100
<212> TYPE: DNA
<213> ORGANISM: Artificial Sequence
<220> FEATURE:
<223> OTHER INFORMATION: Probe

<400> SEQUENCE: 11

```
gggcactgtt taaaggaaag ttccgagaag gcatcgacaa gccggaccct cccacctgga    60
agacgcgcct gcggtgcgct ttgaacaaga gcaatgactt                         100
```

<210> SEQ ID NO 12
<211> LENGTH: 100
<212> TYPE: DNA
<213> ORGANISM: Artificial Sequence
<220> FEATURE:
<223> OTHER INFORMATION: Probe

<400> SEQUENCE: 12

```
gtggagctgg ataatcagat agttactgct acccagagca atatctgtga tgaagacagt    60
gctacagaga cctgctacac ttatgacaga aacaagtgct                         100
```

<210> SEQ ID NO 13
<211> LENGTH: 100
<212> TYPE: DNA
<213> ORGANISM: Artificial Sequence
<220> FEATURE:
<223> OTHER INFORMATION: Probe

<400> SEQUENCE: 13

```
gatcttaggc atgtgctggt atccacagtt aattccctgc taaatgccat gtttatcacc    60
ctaattaata gaatggaggg gactccaaag ctggaactga                         100
```

<210> SEQ ID NO 14
<211> LENGTH: 100
<212> TYPE: DNA
<213> ORGANISM: Artificial Sequence
<220> FEATURE:
<223> OTHER INFORMATION: Probe

<400> SEQUENCE: 14

```
ctgttactag cattcacatg gaacaaattg ctgccgtggg aggatgacaa agaagcatga    60
gtcaccctgc tggataaact tagacttcag gctttatcat                         100
```

<210> SEQ ID NO 15

```
<211> LENGTH: 100
<212> TYPE: DNA
<213> ORGANISM: Artificial Sequence
<220> FEATURE:
<223> OTHER INFORMATION: Probe

<400> SEQUENCE: 15
tcggacaccg aggagaatgt caagaggcga acacacaacg tcttggagcg ccagaggagg      60
aacgagctaa aacggagctt ttttgccctg cgtgaccaga                          100

<210> SEQ ID NO 16
<211> LENGTH: 100
<212> TYPE: DNA
<213> ORGANISM: Artificial Sequence
<220> FEATURE:
<223> OTHER INFORMATION: Probe

<400> SEQUENCE: 16
tgcttctctc ctgcagctcc acctacgtca acggtgtcat gattgtcctg gcggatgctt      60
tctacggcat agtgaacttc ctgatgacca tcgcgtccta                          100

<210> SEQ ID NO 17
<211> LENGTH: 100
<212> TYPE: DNA
<213> ORGANISM: Artificial Sequence
<220> FEATURE:
<223> OTHER INFORMATION: Probe

<400> SEQUENCE: 17
tttgccacca ctgcaagcaa aagtctggag aagttcacca acgacaagaa cgattaggga      60
aaatatgctg ctgtgggtta acaactcaga aagtccctga                          100

<210> SEQ ID NO 18
<211> LENGTH: 100
<212> TYPE: DNA
<213> ORGANISM: Artificial Sequence
<220> FEATURE:
<223> OTHER INFORMATION: Probe

<400> SEQUENCE: 18
gatgggctac aatatggtca cagatgtgac attgatgtgt ccactgaagc catgtatgct      60
gcaaccagac gagaaggatt taatgatgtg gtgagaggaa                          100

<210> SEQ ID NO 19
<211> LENGTH: 100
<212> TYPE: DNA
<213> ORGANISM: Artificial Sequence
<220> FEATURE:
<223> OTHER INFORMATION: Probe

<400> SEQUENCE: 19
tctcagcctc catgacatct ctaccgaaat gtgccgggag aaagaagagc tggtgctctt      60
ggtccttggc cagcagcctg taatctccca ggaggacagg                          100

<210> SEQ ID NO 20
<211> LENGTH: 100
<212> TYPE: DNA
<213> ORGANISM: Artificial Sequence
<220> FEATURE:
<223> OTHER INFORMATION: Probe

<400> SEQUENCE: 20
gtcggacgcg ctgtgcgagt ttgacgcggt gctggccgac ttcgcgtcgc ccttccacga      60
```
gcgccacttc cactacgagg agcacctgga gcgcatgaag                                  100

<210> SEQ ID NO 21
<211> LENGTH: 100
<212> TYPE: DNA
<213> ORGANISM: Artificial Sequence
<220> FEATURE:
<223> OTHER INFORMATION: Probe

<400> SEQUENCE: 21
cccacagttc atcaaagcca ccatcgtgca ccaagaccag gcttacgatg acaagatcta           60
ctacttcttc cgagaggaca atcctgacaa gaatcctgag                                 100

<210> SEQ ID NO 22
<211> LENGTH: 100
<212> TYPE: DNA
<213> ORGANISM: Artificial Sequence
<220> FEATURE:
<223> OTHER INFORMATION: Probe

<400> SEQUENCE: 22
gggctggagt gaccatagga ttctggatca accatttctt ccagcttgta tccaagcccg           60
ctgaatctct ccctgttatt cagaacatcc caccactcac                                 100

<210> SEQ ID NO 23
<211> LENGTH: 100
<212> TYPE: DNA
<213> ORGANISM: Artificial Sequence
<220> FEATURE:
<223> OTHER INFORMATION: Probe

<400> SEQUENCE: 23
ccgcacagca ttttctaaag aagaatcgaa gcctgaccac tttcaccttg ggcaagaagg           60
tttggccttt gagttgctat tctatgctga agagcctgct                                 100

<210> SEQ ID NO 24
<211> LENGTH: 100
<212> TYPE: DNA
<213> ORGANISM: Artificial Sequence
<220> FEATURE:
<223> OTHER INFORMATION: Probe

<400> SEQUENCE: 24
acctcctaat ctaagaggat ccagcctacc tggaaagcca accagtcctc ataatggaca           60
agatccacca gctcctcctg tggactaact ttgtgatatg                                 100

<210> SEQ ID NO 25
<211> LENGTH: 100
<212> TYPE: DNA
<213> ORGANISM: Artificial Sequence
<220> FEATURE:
<223> OTHER INFORMATION: Probe

<400> SEQUENCE: 25
tgcaagtttt gaacctaagt aaacctcaat ccggagggcc tagcggtaag gtgggcgctg           60
tgtctattga agtgcttagc aataaagaaa ggtagtgagt                                 100

<210> SEQ ID NO 26
<211> LENGTH: 100
<212> TYPE: DNA
<213> ORGANISM: Artificial Sequence
<220> FEATURE:

<223> OTHER INFORMATION: Probe

<400> SEQUENCE: 26
aaagaaggag gcgtcacttt cacttgggtg gagaaggaca tcagcggtaa gacccagatc    60
cagtccgtgg aaccatacac aaagcagcag ctgaacaaca                          100

<210> SEQ ID NO 27
<211> LENGTH: 100
<212> TYPE: DNA
<213> ORGANISM: Artificial Sequence
<220> FEATURE:
<223> OTHER INFORMATION: Probe

<400> SEQUENCE: 27
cactcaaaga agccaggaaa gagattaaac agctcaaaca ggtcatcgaa accatgcgga    60
gcagcttggc tgataaagat aaaggcattc agaaatattt                          100

<210> SEQ ID NO 28
<211> LENGTH: 100
<212> TYPE: DNA
<213> ORGANISM: Artificial Sequence
<220> FEATURE:
<223> OTHER INFORMATION: Probe

<400> SEQUENCE: 28
ccctcaaagg aggaaattgc tcagaagacc tcttatgtat cctgaaaagg gctccattca    60
agaagtcatg ggcctacctc caagtggcaa agcatctaaa                          100

<210> SEQ ID NO 29
<211> LENGTH: 100
<212> TYPE: DNA
<213> ORGANISM: Artificial Sequence
<220> FEATURE:
<223> OTHER INFORMATION: Probe

<400> SEQUENCE: 29
agacccgctt ctcctttccg cacacccggc ctgtcaccct gctttccctg cctctacttg    60
acttggaatt ggctgaagac tacacaggaa tgcatcgttc                          100

<210> SEQ ID NO 30
<211> LENGTH: 100
<212> TYPE: DNA
<213> ORGANISM: Artificial Sequence
<220> FEATURE:
<223> OTHER INFORMATION: Probe

<400> SEQUENCE: 30
gagcctcttg agaaattgtt actcattgaa ctggagcatc aagacatctc atggaagtgg    60
atacggagtg atttggtgtc catgcttttc actctgagga                          100

<210> SEQ ID NO 31
<211> LENGTH: 100
<212> TYPE: DNA
<213> ORGANISM: Artificial Sequence
<220> FEATURE:
<223> OTHER INFORMATION: Probe

<400> SEQUENCE: 31
agttcggtgg ggtcatgtgt gtggagagcg tcaaccggga gatgtcgccc ctggtggaca    60
acatcgccct gtggatgact gagtacctga accggcacct                          100

<210> SEQ ID NO 32
<211> LENGTH: 100
<212> TYPE: DNA
<213> ORGANISM: Artificial Sequence
<220> FEATURE:
<223> OTHER INFORMATION: Probe

<400> SEQUENCE: 32
aggctgacaa agttggggct gagaacacaa tcacctattc acttctcatg cacccggatg     60
ctctggaaga gcctgatgac cagaaccgta tttagtctcc                          100

<210> SEQ ID NO 33
<211> LENGTH: 100
<212> TYPE: DNA
<213> ORGANISM: Artificial Sequence
<220> FEATURE:
<223> OTHER INFORMATION: Probe

<400> SEQUENCE: 33
gatggctgtg cctgtcagct gcatggagct tcgttcaagt attttctgag cctgatggat     60
ttacagtgat cttcagtggt ctggggaata acgctggtgg                          100

<210> SEQ ID NO 34
<211> LENGTH: 100
<212> TYPE: DNA
<213> ORGANISM: Artificial Sequence
<220> FEATURE:
<223> OTHER INFORMATION: Probe

<400> SEQUENCE: 34
ggacacgtag gcggtaccac taaggttttg gtaatgagcc attcaaaccg acagcagtgt     60
gaaggtgtgt caaggtgtat attctcgtgg ctcggcattc                          100

<210> SEQ ID NO 35
<211> LENGTH: 100
<212> TYPE: DNA
<213> ORGANISM: Artificial Sequence
<220> FEATURE:
<223> OTHER INFORMATION: Probe

<400> SEQUENCE: 35
ggtggtcttg aactggcttt agcctgtgat atacgagtag cagcttcctc tgcaaaaatg     60
ggcctggttg aaacaaaatt ggcgattatt cctggtggag                          100

<210> SEQ ID NO 36
<211> LENGTH: 100
<212> TYPE: DNA
<213> ORGANISM: Artificial Sequence
<220> FEATURE:
<223> OTHER INFORMATION: Probe

<400> SEQUENCE: 36
ggcaaatgaa atggaagggg aaggaaaaca gaatggatca ggcatggaga ccaaacacag     60
cccactagag gttggcagtg agagttctga agaccagtat                          100

<210> SEQ ID NO 37
<211> LENGTH: 100
<212> TYPE: DNA
<213> ORGANISM: Artificial Sequence
<220> FEATURE:
<223> OTHER INFORMATION: Probe

<400> SEQUENCE: 37
ctgctgttat gcagagccat ttcctctaga atttggataa taaagatgct tattgtctct   60
cccttctcca gttctgggaa tttacaggca caatacactt                         100

<210> SEQ ID NO 38
<211> LENGTH: 100
<212> TYPE: DNA
<213> ORGANISM: Artificial Sequence
<220> FEATURE:
<223> OTHER INFORMATION: Probe

<400> SEQUENCE: 38
tgctctcctt gggatgatgg ctggctagtc agccttgcat gtattccttg gctgaatggg   60
agagtgcccc atgttctgca agactacttg gtattcttgt                         100

<210> SEQ ID NO 39
<211> LENGTH: 100
<212> TYPE: DNA
<213> ORGANISM: Artificial Sequence
<220> FEATURE:
<223> OTHER INFORMATION: Probe

<400> SEQUENCE: 39
ttgaaaatcg gcccaagaag gagcaggttc tggaactgga gcgggagaat gaaatgctga   60
agaccaaaaa ccaggagctg cagtccatca tccaggccgg                         100

<210> SEQ ID NO 40
<211> LENGTH: 100
<212> TYPE: DNA
<213> ORGANISM: Artificial Sequence
<220> FEATURE:
<223> OTHER INFORMATION: Probe

<400> SEQUENCE: 40
aaacactttc cagagttccc tgcaacccgt gcttatgcag atagttacta ttatgaagat   60
ggaggaatga agccaagagt gatgaaagaa gctgtatcta                         100

<210> SEQ ID NO 41
<211> LENGTH: 100
<212> TYPE: DNA
<213> ORGANISM: Artificial Sequence
<220> FEATURE:
<223> OTHER INFORMATION: Probe

<400> SEQUENCE: 41
gcctggagta cttcaaggga gccattcccc ttagaaagct gaagacgtgg taccagacat   60
ctgaggactg ctccagggat gccatcgttt ttgtaactgt                         100

<210> SEQ ID NO 42
<211> LENGTH: 100
<212> TYPE: DNA
<213> ORGANISM: Artificial Sequence
<220> FEATURE:
<223> OTHER INFORMATION: Probe

<400> SEQUENCE: 42
atgcctgagg ggatcaggct tttctactcc aggcaaacct gccccatctt gtcgcttttα   60 ggacctccca caacctggtt ccccacacat ccatagttct                         100

<210> SEQ ID NO 43
<211> LENGTH: 100
<212> TYPE: DNA
<213> ORGANISM: Artificial Sequence

```
<220> FEATURE:
<223> OTHER INFORMATION: Probe

<400> SEQUENCE: 43
ccatgtctta gggcttcctg taggtaacta tgtccagctc ttggcaaaaa tcgataatga      60
attggtggtc agggcttaca cccctgtctc cagtgatgat                          100

<210> SEQ ID NO 44
<211> LENGTH: 100
<212> TYPE: DNA
<213> ORGANISM: Artificial Sequence
<220> FEATURE:
<223> OTHER INFORMATION: Probe

<400> SEQUENCE: 44
tttcttccat gttttagaaa atgaggcctg tttggggaag gtaccctggt gatgttttttg     60 ctagacatta gctgtagctg acagcataag gagagtcgca                          100

<210> SEQ ID NO 45
<211> LENGTH: 100
<212> TYPE: DNA
<213> ORGANISM: Artificial Sequence
<220> FEATURE:
<223> OTHER INFORMATION: Probe

<400> SEQUENCE: 45 attgcgctc tcataggcct gtccgtagca gcagtggttc ttctcgcctt cattgttacc       60
gcctgtgtgc tctgctacct gttcatcagc tctaagcccc                          100

<210> SEQ ID NO 46
<211> LENGTH: 100
<212> TYPE: DNA
<213> ORGANISM: Artificial Sequence
<220> FEATURE:
<223> OTHER INFORMATION: Probe

<400> SEQUENCE: 46
ccctgccctc ttgtctgcca cggggcgagt ctggcacctc tttcttctga cctcagacgg      60
ctctgagcct tatttctctg gaagcggcta agggacggtt                          100

<210> SEQ ID NO 47
<211> LENGTH: 100
<212> TYPE: DNA
<213> ORGANISM: Artificial Sequence
<220> FEATURE:
<223> OTHER INFORMATION: Probe

<400> SEQUENCE: 47
cagattttac aggctgaatt attggcagta tatggagcag acccaggcac acaggattct      60
agtgggaaaa ctcccgttga ttatgcaagg caaggagggc                          100

<210> SEQ ID NO 48
<211> LENGTH: 100
<212> TYPE: DNA
<213> ORGANISM: Artificial Sequence
<220> FEATURE:
<223> OTHER INFORMATION: Probe

<400> SEQUENCE: 48
actgattata cctctagtat agatgtatgg tctgctggct gtgtgttggc tgagctgtta      60
ctaggacaac caatatttcc agggatagt ggtgtggatc                           100
```

<210> SEQ ID NO 49
<211> LENGTH: 100
<212> TYPE: DNA
<213> ORGANISM: Artificial Sequence
<220> FEATURE:
<223> OTHER INFORMATION: Probe

<400> SEQUENCE: 49
tggaagacaa agtgcgttcc ttaaagacag acattgagga gagcaaatac cgacagcgcc    60
acctgaaggt ggagttgaag agcttcctgg aggtgctgga    100

<210> SEQ ID NO 50
<211> LENGTH: 100
<212> TYPE: DNA
<213> ORGANISM: Artificial Sequence
<220> FEATURE:
<223> OTHER INFORMATION: Probe

<400> SEQUENCE: 50
gcttgggaga accctctccc ttctctgaga aagaaagatg tcgaatgggt attccacaga    60
cgagaatttc cgctatctca tctcgtgctt cagggccagg    100

<210> SEQ ID NO 51
<211> LENGTH: 100
<212> TYPE: DNA
<213> ORGANISM: Artificial Sequence
<220> FEATURE:
<223> OTHER INFORMATION: Probe

<400> SEQUENCE: 51
gtccaaattc ttgggtggtg acatggaaca cacccatttg gtgaaaggct tggattttgc    60
tctgcttcaa aaggtacgag ctgagattgc cagcaaagag    100

<210> SEQ ID NO 52
<211> LENGTH: 100
<212> TYPE: DNA
<213> ORGANISM: Artificial Sequence
<220> FEATURE:
<223> OTHER INFORMATION: Probe

<400> SEQUENCE: 52
tctgcactgg aagaagtacg acatctatga gaagcaaacc aaggaggaaa ccgactctgt    60
agtgctgata gaaaacctga agaaagcctc tcagtgatgg    100

<210> SEQ ID NO 53
<211> LENGTH: 100
<212> TYPE: DNA
<213> ORGANISM: Artificial Sequence
<220> FEATURE:
<223> OTHER INFORMATION: Probe

<400> SEQUENCE: 53
ggcaaaacat cagtgtctgt gggtagttgg aatcttcagt tcctgtgagc gtcggcgtct    60
tctgggcctg tggagtttct tggacagggg ccgcggggct    100

<210> SEQ ID NO 54
<211> LENGTH: 100
<212> TYPE: DNA
<213> ORGANISM: Artificial Sequence
<220> FEATURE:
<223> OTHER INFORMATION: Probe

<400> SEQUENCE: 54
gtggcctcct ggcatcattt gttattgcct ctgaaacaag ccttactgcc tggagggctt    60
agattcctgc ttctccaatg tagtgtgggt atcttgtagg                         100

<210> SEQ ID NO 55
<211> LENGTH: 100
<212> TYPE: DNA
<213> ORGANISM: Artificial Sequence
<220> FEATURE:
<223> OTHER INFORMATION: Probe

<400> SEQUENCE: 55
aactacatcc tgaactcgac gtcctgaggt ataatacaac agagcacttt ttgaggcaat    60
tgaaaaacca acctacactc ttcggtgctt agagagatct                         100

<210> SEQ ID NO 56
<211> LENGTH: 100
<212> TYPE: DNA
<213> ORGANISM: Artificial Sequence
<220> FEATURE:
<223> OTHER INFORMATION: Probe

<400> SEQUENCE: 56
aaggcaagtc tcaggaaccc atgcaggtac atcgcttgca cctgttttta gcttatttaa    60
tgacgggctt ttgggaagag ctgcccgcat actgagagac                         100

<210> SEQ ID NO 57
<211> LENGTH: 100
<212> TYPE: DNA
<213> ORGANISM: Artificial Sequence
<220> FEATURE:
<223> OTHER INFORMATION: Probe

<400> SEQUENCE: 57
gccttcgcgt ccgggttggg agcttgctgt gtctaacctc caactgctgt gctgtctgct    60
agggtcacct cctgtttgtg aaagggggacc ttcttgttcg                        100

<210> SEQ ID NO 58
<211> LENGTH: 100
<212> TYPE: DNA
<213> ORGANISM: Artificial Sequence
<220> FEATURE:
<223> OTHER INFORMATION: Probe

<400> SEQUENCE: 58
tggaagccat caacaatttg cccagtaaca tgccactgcc ttcagcttct cctcttcacc    60
aacttgacct gaaaccttct ttgcccttgc agaacagtgg                         100

<210> SEQ ID NO 59
<211> LENGTH: 100
<212> TYPE: DNA
<213> ORGANISM: Artificial Sequence
<220> FEATURE:
<223> OTHER INFORMATION: Probe

<400> SEQUENCE: 59
ggattgtagg tgcaagctgt ccagagaaaa gagtccttgt tccagcccta ttctgccact    60
cctgacaggg tgaccttggg tatttgcaat attcctttgg                         100

<210> SEQ ID NO 60
<211> LENGTH: 100
<212> TYPE: DNA

<213> ORGANISM: Artificial Sequence
<220> FEATURE:
<223> OTHER INFORMATION: Probe

<400> SEQUENCE: 60
ttctcttacc cagagatgcc catgagctga cattttactc atccctctgc ctccaagaag    60
gcctgtatta tacgtgtcct cctgggggtt ggagatgatc    100

<210> SEQ ID NO 61
<211> LENGTH: 100
<212> TYPE: DNA
<213> ORGANISM: Artificial Sequence
<220> FEATURE:
<223> OTHER INFORMATION: Probe

<400> SEQUENCE: 61
ccactttgga gttgtctacc acggagaata catagaccag gcccagaatc gaatccaatg    60
tgccatcaag tcactaagtc gcatcacaga gatgcagcag    100

<210> SEQ ID NO 62
<211> LENGTH: 100
<212> TYPE: DNA
<213> ORGANISM: Artificial Sequence
<220> FEATURE:
<223> OTHER INFORMATION: Probe

<400> SEQUENCE: 62
ggcaaacgct gtgttatcct ctttgcagac catcccagaa tttgcagaga ctctagaact    60
tattgaatct gatcctgtag catggagtga cgttaccagt    100

<210> SEQ ID NO 63
<211> LENGTH: 100
<212> TYPE: DNA
<213> ORGANISM: Artificial Sequence
<220> FEATURE:
<223> OTHER INFORMATION: Probe

<400> SEQUENCE: 63
ctctcctctc ctccttgtct ggctctgttg acaaaccggg catgtttggc agtaaattgg    60
caccgtgtca cactgtttcc tgggattcaa gtatgcaacc    100

<210> SEQ ID NO 64
<211> LENGTH: 99
<212> TYPE: DNA
<213> ORGANISM: Artificial Sequence
<220> FEATURE:
<223> OTHER INFORMATION: Probe

<400> SEQUENCE: 64
cctttctttc tcctcgccgg cccgagagca ggaacacgat aacgaaggag gcccaacttc    60
attcaataag gagcctgacg gatttatccc agacggtag    99

<210> SEQ ID NO 65
<211> LENGTH: 100
<212> TYPE: DNA
<213> ORGANISM: Artificial Sequence
<220> FEATURE:
<223> OTHER INFORMATION: Probe

<400> SEQUENCE: 65
ctgagaccat atccttaaat gtaaaaggcc ctggactaca gaggatggtg cttgttgact    60
taccaggtgt gattaatact gtgacatcag gcatggctcc    100

<210> SEQ ID NO 66
<211> LENGTH: 100
<212> TYPE: DNA
<213> ORGANISM: Artificial Sequence
<220> FEATURE:
<223> OTHER INFORMATION: Probe

<400> SEQUENCE: 66
ctgtctgtgt cccgacacat aatctctgtc tcttggacct gccaccatca ctttctgggt    60
caggattgga attgggatgg aatgggacag ttgtctataa                         100

<210> SEQ ID NO 67
<211> LENGTH: 100
<212> TYPE: DNA
<213> ORGANISM: Artificial Sequence
<220> FEATURE:
<223> OTHER INFORMATION: Probe

<400> SEQUENCE: 67
ctgtctgtgt cccgacacat aatctctgtc tcttggacct gccaccatca ctttctgggt    60
caggattgga attgggatgg aatgggacag ttgtctataa                         100

<210> SEQ ID NO 68
<211> LENGTH: 100
<212> TYPE: DNA
<213> ORGANISM: Artificial Sequence
<220> FEATURE:
<223> OTHER INFORMATION: Probe

<400> SEQUENCE: 68
gccatccagc actgccattc ccgtggagtt gtccatcgtg acatcaagga tgagaacatc    60
ctgatagacc tacgccgtgg ctgtgccaaa ctcattgatt                         100

<210> SEQ ID NO 69
<211> LENGTH: 100
<212> TYPE: DNA
<213> ORGANISM: Artificial Sequence
<220> FEATURE:
<223> OTHER INFORMATION: Probe

<400> SEQUENCE: 69
gcatggggaa gtttgtcccg ctggctggaa gcctggcagt gacacgatta agcccaacgt    60
ggatgacagc aaggaatatt tctccaaaca caattaggct                         100

<210> SEQ ID NO 70
<211> LENGTH: 100
<212> TYPE: DNA
<213> ORGANISM: Artificial Sequence
<220> FEATURE:
<223> OTHER INFORMATION: Probe

<400> SEQUENCE: 70
gcatttggag tcctgctgta tgaaatgttg gctgggcagg caccctttga aggggaggat    60
gaagatgaac tcttccaatc catcatggaa cacaacgtag                         100

<210> SEQ ID NO 71
<211> LENGTH: 100
<212> TYPE: DNA
<213> ORGANISM: Artificial Sequence
<220> FEATURE:
<223> OTHER INFORMATION: Probe

<400> SEQUENCE: 71
ttcattgttc cagcttctcg cttcaagctc ctgaagggag ctgagcacat aacgacttac    60
acgttcaata ctcacaaagc ccagcatacc ttctgtaaga                          100

<210> SEQ ID NO 72
<211> LENGTH: 100
<212> TYPE: DNA
<213> ORGANISM: Artificial Sequence
<220> FEATURE:
<223> OTHER INFORMATION: Probe

<400> SEQUENCE: 72
ctgacatttc aagctgaccc tgtgatctct gccctgtctt cgggcgacag gagccagaaa    60
atcagggaca tggctgatgg ctgcggatgc tggaaccttg                          100

<210> SEQ ID NO 73
<211> LENGTH: 100
<212> TYPE: DNA
<213> ORGANISM: Artificial Sequence
<220> FEATURE:
<223> OTHER INFORMATION: Probe

<400> SEQUENCE: 73
tagggcagct cagtccctgg cctcttagca ccacattcct gttttcagc ttatttgaag     60 tcctgcctca ttctcactgg agcctcagtc tctcctgctt                          100

<210> SEQ ID NO 74
<211> LENGTH: 100
<212> TYPE: DNA
<213> ORGANISM: Artificial Sequence
<220> FEATURE:
<223> OTHER INFORMATION: Probe

<400> SEQUENCE: 74
cctgtgttcc caagagaatt acattattga caaaagactc caagacgagg atgccagtag    60
tacccagcag aggcgccaga tatttagagt taataaagat                          100

<210> SEQ ID NO 75
<211> LENGTH: 100
<212> TYPE: DNA
<213> ORGANISM: Artificial Sequence
<220> FEATURE:
<223> OTHER INFORMATION: Probe

<400> SEQUENCE: 75
catttgaatt gtctcctgac tactgtccag taaggaggcc cattgtcact tagaaaagac    60
acctggaacc catgtgcatt tctgcatctc ctggattagc                          100

<210> SEQ ID NO 76
<211> LENGTH: 100
<212> TYPE: DNA
<213> ORGANISM: Artificial Sequence
<220> FEATURE:
<223> OTHER INFORMATION: Probe

<400> SEQUENCE: 76
tggtgaatca tttgaactga agattgtgcg acggggaatg cctcccggag gaggaggcga    60
agtggttttc tcatgtcctg tgaggaaggt cttgaagccc                          100

<210> SEQ ID NO 77
<211> LENGTH: 100

<212> TYPE: DNA
<213> ORGANISM: Artificial Sequence
<220> FEATURE:
<223> OTHER INFORMATION: Probe

<400> SEQUENCE: 77
ctgcggcaag acctcgctgc tcatggtgta cagccagggc tccttccccg agcactacgc    60
cccatcggtg ttcgagaagt acacggccag cgtgaccgtt                         100

<210> SEQ ID NO 78
<211> LENGTH: 100
<212> TYPE: DNA
<213> ORGANISM: Artificial Sequence
<220> FEATURE:
<223> OTHER INFORMATION: Probe

<400> SEQUENCE: 78
tcccgccagg tggcctcggc cttcatcgtc atcctctgtt gcgccattgt ggtggaaaac    60
cttctggtgc tcattgcggt ggcccgaaac agcaagttcc                         100

<210> SEQ ID NO 79
<211> LENGTH: 100
<212> TYPE: DNA
<213> ORGANISM: Artificial Sequence
<220> FEATURE:
<223> OTHER INFORMATION: Probe

<400> SEQUENCE: 79
ccactaaatc ctaggtggga aatggcctgt taactgatgg cacattgcta atgcacaaga    60
aataacaaac cacatccctc tttctgttct gagggtgcat                         100

<210> SEQ ID NO 80
<211> LENGTH: 100
<212> TYPE: DNA
<213> ORGANISM: Artificial Sequence
<220> FEATURE:
<223> OTHER INFORMATION: Probe

<400> SEQUENCE: 80
gtgtctcttg atccatccga agcaggccct ccacgttatc taggagatcg ctacaagttt    60
tatctggaga atctcaccct ggggatacgg gaaagcagga                         100

<210> SEQ ID NO 81
<211> LENGTH: 100
<212> TYPE: DNA
<213> ORGANISM: Artificial Sequence
<220> FEATURE:
<223> OTHER INFORMATION: Probe

<400> SEQUENCE: 81
tcatttgtat gtaggaccag gagtatctcc tcaggtgacc agttttgggg acccgtatgt    60
ggcaaattct aagctgccat attgaacatc atcccactgg                         100

<210> SEQ ID NO 82
<211> LENGTH: 100
<212> TYPE: DNA
<213> ORGANISM: Artificial Sequence
<220> FEATURE:
<223> OTHER INFORMATION: Probe

<400> SEQUENCE: 82
tttaatccaa gatacagaac ctgtgatgct ttcacctata ctggctgtgg agggaatgac    60
aataactttg ttagcaggga ggattgcaaa cgtgcatgtg          100

<210> SEQ ID NO 83
<211> LENGTH: 100
<212> TYPE: DNA
<213> ORGANISM: Artificial Sequence
<220> FEATURE:
<223> OTHER INFORMATION: Probe

<400> SEQUENCE: 83
agatgctcaa ggagaacaag gtgttgaaga cactgaatgt ggaatccaac ttcatttctg     60
gagctgggat tctgcgcctg gtagaagccc tcccatacaa                          100

<210> SEQ ID NO 84
<211> LENGTH: 100
<212> TYPE: DNA
<213> ORGANISM: Artificial Sequence
<220> FEATURE:
<223> OTHER INFORMATION: Probe

<400> SEQUENCE: 84
tgcaaaacca tttgcaacca tcagagccag cgcacctgtg cagccttctg caggtcactc     60
agctgccgca aggagcaagg caagttctat gaccatctcc                          100

<210> SEQ ID NO 85
<211> LENGTH: 100
<212> TYPE: DNA
<213> ORGANISM: Artificial Sequence
<220> FEATURE:
<223> OTHER INFORMATION: Probe

<400> SEQUENCE: 85
cgagtgatgg gtctaggccc tgaaactgat gtcctagcaa taacctcttg atccctactc     60
accgagtgtt gagcccaagg ggggatttgt agaacaagcc                          100

<210> SEQ ID NO 86
<211> LENGTH: 100
<212> TYPE: DNA
<213> ORGANISM: Artificial Sequence
<220> FEATURE:
<223> OTHER INFORMATION: Probe

<400> SEQUENCE: 86
gtggaggccg aggacatttt cctgaagggc aggggttggc aacttttcaa catggagtgc     60
caaactgcta acccgtcttc tagtgtgtga aatagggac                           100

<210> SEQ ID NO 87
<211> LENGTH: 100
<212> TYPE: DNA
<213> ORGANISM: Artificial Sequence
<220> FEATURE:
<223> OTHER INFORMATION: Probe

<400> SEQUENCE: 87
catcgcgacg gccaaaagga gcggcgcggt cttcgtggtg ttcgtggcag gtgatgatga     60
acagtctaca cagatggctg caagttggga agatgataaa                          100

<210> SEQ ID NO 88
<211> LENGTH: 100
<212> TYPE: DNA
<213> ORGANISM: Artificial Sequence
<220> FEATURE:
<223> OTHER INFORMATION: Probe

```
<400> SEQUENCE: 88
acagacaaga gtgggcgaca gtggaagctg aagtccttcc agaccaggga caaccagggc      60
attctctatg aagctgcacc cacctccacc ctcacctgtg                          100

<210> SEQ ID NO 89
<211> LENGTH: 100
<212> TYPE: DNA
<213> ORGANISM: Artificial Sequence
<220> FEATURE:
<223> OTHER INFORMATION: Probe

<400> SEQUENCE: 89
cctctggact gaacccaca tctgcacctc caacatctgc ttcagcggtc cctgtttctc       60
ctgttccaca gtcgccaata cctcccttac ttcaggaccc                          100

<210> SEQ ID NO 90
<211> LENGTH: 100
<212> TYPE: DNA
<213> ORGANISM: Artificial Sequence
<220> FEATURE:
<223> OTHER INFORMATION: Probe

<400> SEQUENCE: 90
ctacctcttc aattggaatg gctttggggc cacaagtgac cgctttgccc tgagagctga      60
atctatcgac tgcatggttc cagtcaccga gagtctgctg                          100
```

GENE EXPRESSION PROFILES FOR B-CELL LYMPHOMA AND USES THEREOF

CROSS-REFERENCE TO RELATED APPLICATIONS

This application is a 371 national phase entry of Patent Cooperation Treaty application No. PCT/IB2019/058784 filed 15 Oct. 2019, which claims the benefit of U.S. provisional patent application No. 62/745,556 filed 15 Oct. 2018. Both of the foregoing applications are hereby incorporated by reference herein in their entirety.

FIELD OF INVENTION

The present invention relates to gene expression profiles for B-cell lymphoma. More specifically, the present invention relates to gene expression profiles for diagnosis, prognosis or therapy selection for aggressive B-cell lymphomas.

STATEMENT REGARDING SEQUENCE LISTING

The Sequence Listing associated with this application is provided in computer readable text format and is hereby incorporated by reference into the specification. The name of the text file containing the Sequence Listing is Sequence_Listing.txt. The text file is 23.4 kb in size and was created on 15 Sep. 2021, and is being electronically submitted via EFS-Web.

BACKGROUND OF THE INVENTION

The biological heterogeneity in diffuse large B-cell lymphoma (DLBCL) has prompted significant effort to define distinct molecular subgroups within the disease[1-3]. Accordingly, the most recent revision of the WHO classification divides tumors with DLBCL morphology into cell-of-origin (COO) molecular subtypes: activated B-cell-like (ABC) and germinal center B-cell-like (GCB) subtypes and recognizes high-grade B-cell lymphoma with MYC and BCL2 and/or BCL6 rearrangements (HGBL-DH/TH)[4], which includes tumors with either DLBCL or high-grade morphology. Approximately 8% of tumors with DLBCL morphology are HGBL-DH/TH and all HGBL-DH/TH with BCL2 translocations (HGBL-DH/TH-BCL2) of DLBCL morphology belong to the GCB molecular subgroup[5,6]. Clinically, despite the generally superior prognosis of GCB-DLBCLs, HGBL-DH/TH-BCL2 patients have poor outcomes[7-12], prompting treatment of such tumors with dose intensive immunochemotherapy. Genomic studies in DLBCL have identified recurrent mutations and revealed the association of many with COO[13-16]. Genomic landscape studies have defined genetic subgroups based on somatic mutation and structural variants[17-19].

SUMMARY OF THE INVENTION

In one aspect, the present invention provides a method for selecting a therapy for a subject with an aggressive B-cell lymphoma by determining the molecular subgroup of the aggressive B-cell lymphoma, where the molecular subgroup is a positive DHIT signature (DHITsig-pos) or a negative DHIT signature (DHITsig-neg) lymphoma, and where therapy is selected based on the molecular subgroup determination.

In an alternative aspect, the present invention provides a method for identifying a subject with an aggressive B-cell lymphoma as a candidate for a therapy by determining the molecular subgroup of the aggressive B-cell lymphoma, where the molecular subgroup is a positive DHIT signature (DHITsig-pos) or a negative DHIT signature (DHITsig-neg) lymphoma, and where the subject is identified as a candidate for the therapy based on the molecular subgroup determination.

In some embodiments, the molecular subgroup may be DHITsig-neg and the therapy may be rituximab, cyclophosphamide, doxorubicin hydrochloride, vincristine sulfate and prednisone (R-CHOP). In some embodiments, the molecular subgroup may be DHITsig-pos and the therapy may be an alternate therapy.

In some embodiments, the aggressive B-cell lymphoma may be a germinal centre B-cell-like diffuse large B-cell lymphoma (GCB-DLBCL). In some embodiments, the aggressive B-cell lymphoma may be a high-grade B-cell lymphoma with BCL2 translocations (HGBL-DH/TH-BCL2).

In some embodiments, determining the molecular subgroup of the aggressive B-cell lymphoma may include preparing a gene expression profile for one or more genes listed in Table 1 from a test sample from the subject.

In an alternative aspect, the present invention provides a method for determining the prognosis of a subject with an aggressive B-cell lymphoma by providing a gene expression profile for two or more genes listed in Table 1 from a test sample from the subject; and classifying the test sample into an aggressive B-cell lymphoma subgroup having a positive DHIT signature (DHITsig-pos) or an aggressive B-cell lymphoma subgroup having a negative DHIT signature (DHITsig-neg) based on the gene expression profile, where DHITsig-pos is predictive of a poor prognosis and DHITsig-neg is predictive of a good prognosis.

In an alternative aspect, the present invention provides a method of classifying an aggressive B-cell lymphoma by providing a test sample; preparing a gene expression profile for two or more genes listed in Table 1 from the test sample; and classifying the test sample into an aggressive B-cell lymphoma having a positive DHIT signature (DHITsig-pos) or an aggressive B-cell lymphoma having a negative DHIT signature (DHITsig-neg) based on the gene expression profile.

In some embodiments, the genes may include five or more of the genes listed in Table 1. In some embodiments, the genes may be listed in Table 2. In some embodiments, the genes may include all the genes listed in Table 2. In some embodiments, the genes may include five or more of the genes listed in Table 2. In some embodiments, the genes may further include one or more of the Lymph3x genes (Table 6). In some embodiments, the genes may further include one or more of BCL2, FCGR2B and PVT1 (Table 5).

In some embodiments, the test sample may be a biopsy.

In some embodiments, the aggressive B-cell lymphoma may be a diffuse large B-cell lymphoma (DLBCL) or high-grade B-cell lymphoma (HGBL).

In some embodiments, the subject may be a human.

In an alternative aspect, the present invention provides a kit including reagents sufficient for the detection of one or more of the genes listed in Table 1.

This summary of the invention does not necessarily describe all features of the invention.

BRIEF DESCRIPTION OF THE DRAWINGS

These and other features of the invention will become more apparent from the following description in which reference is made to the appended drawings as follows.

FIG. 6A shows the prognostic association of DHIT signature in DLBCL patients treated with R-CHOP. Kaplan Meier curves of the DHITsig-pos GCB-DLBCL (black) vs DHITsig-neg GCB-DLBCL (light grey) vs ABC-DLBCL (dark grey) for TTP in British Columbia Cancer cohort. HR; hazard ratio.

FIG. 6B shows the prognostic association of DHIT signature in DLBCL patients treated with R-CHOP. Kaplan Meier curves of the DHITsig-pos GCB-DLBCL (black) vs DHITsig-neg GCB-DLBCL (light grey) vs ABC-DLBCL (dark grey) for DSS in British Columbia Cancer cohort. HR; hazard ratio.

FIG. 6C shows the prognostic association of DHIT signature in DLBCL patients treated with R-CHOP. Kaplan Meier curves of the DHITsig-pos GCB-DLBCL (black) vs DHITsig-neg GCB-DLBCL (light grey) vs ABC-DLBCL (dark grey) OS in British Columbia Cancer cohort. HR; hazard ratio.

FIG. 6D shows the prognostic association of DHIT signature in DLBCL patients treated with R-CHOP. Kaplan Meier curves of the DHITsig-pos GCB-DLBCL (black) vs DHITsig-neg GCB-DLBCL (light grey) vs ABC-DLBCL (dark grey) for OS in the Reddy et al. validation cohort. HR; hazard ratio.

FIG. 7A shows Kaplan Meier curves of the cases with HGBL-DH/TH-BCL2 (black) vs non-HGBL-DH/TH-BCL2 (grey) within DHITsig-pos GCB-DLBCL for TTP.

FIG. 7B shows Kaplan Meier curves of the cases with HGBL-DH/TH-BCL2 (black) vs non-HGBL-DH/TH-BCL2 (grey) within DHITsig-pos GCB-DLBCL for DSS.

FIG. 8A shows Kaplan Meier curves of cases stratified by DHIT signature combined with DPE status in GCB-DLBCL for TTP.

FIG. 8B shows Kaplan Meier curves of cases stratified by DHIT signature combined with DPE status in GCB-DLBCL for DSS.

FIG. 11A shows the genetic, molecular and phenotypic features of DHIT signature comparing fraction of tumor-infiltrating T-cells (CD3 (left), CD4 (center) and CD8 (right) positive T-cells) measured by flow cytometry between DHITsig-pos, DHITsig-neg GCB-DLBCL and ABC-DLBCL.

FIG. 11B shows the genetic, molecular and phenotypic features of DHIT signature comparing frequencies of MHC-I and -II double negative (black), isolated MHC-II negative, isolated MHC-I negative and MHC-I and -II double positive cases in DHITsig-pos (left) and DHITsig-neg cases (right).

FIG. 15A shows the prognostic association of DLBCL90 in DLBCL patients treated with R-CHOP by Kaplan Meier curves of the GCB-DLBCL (light grey) vs DHITsig-pos and -ind (black) vs Unclassified (medium grey) vs ABC-DLBCL (dark grey) for TTP in 322 patients with de novo tumors of DLBCL morphology treated with R-CHOP.

FIG. 15B shows the prognostic association of DLBCL90 in DLBCL patients treated with R-CHOP by Kaplan Meier curves of the GCB-DLBCL (light grey) vs DHITsig-pos and -ind (black) vs Unclassified (medium grey) vs ABC-DLBCL (dark grey) for DSS in 322 patients with de novo tumors of DLBCL morphology treated with R-CHOP.

FIG. 15C shows the prognostic association of DLBCL90 in DLBCL patients treated with R-CHOP by Kaplan Meier curves of the GCB-DLBCL (light grey) vs DHITsig-pos and -ind (black) vs Unclassified (medium grey) vs ABC-DLBCL (dark grey) for PFS in 322 patients with de novo tumors of DLBCL morphology treated with R-CHOP.

FIG. 15D shows the prognostic association of DLBCL90 in DLBCL patients treated with R-CHOP by Kaplan Meier curves of the GCB-DLBCL (light grey) vs DHITsig-pos and -ind (black) vs Unclassified (medium grey) vs ABC-DLBCL (dark grey) for OS in 322 patients with de novo tumors of DLBCL morphology treated with R-CHOP.

DETAILED DESCRIPTION

Figure 1:
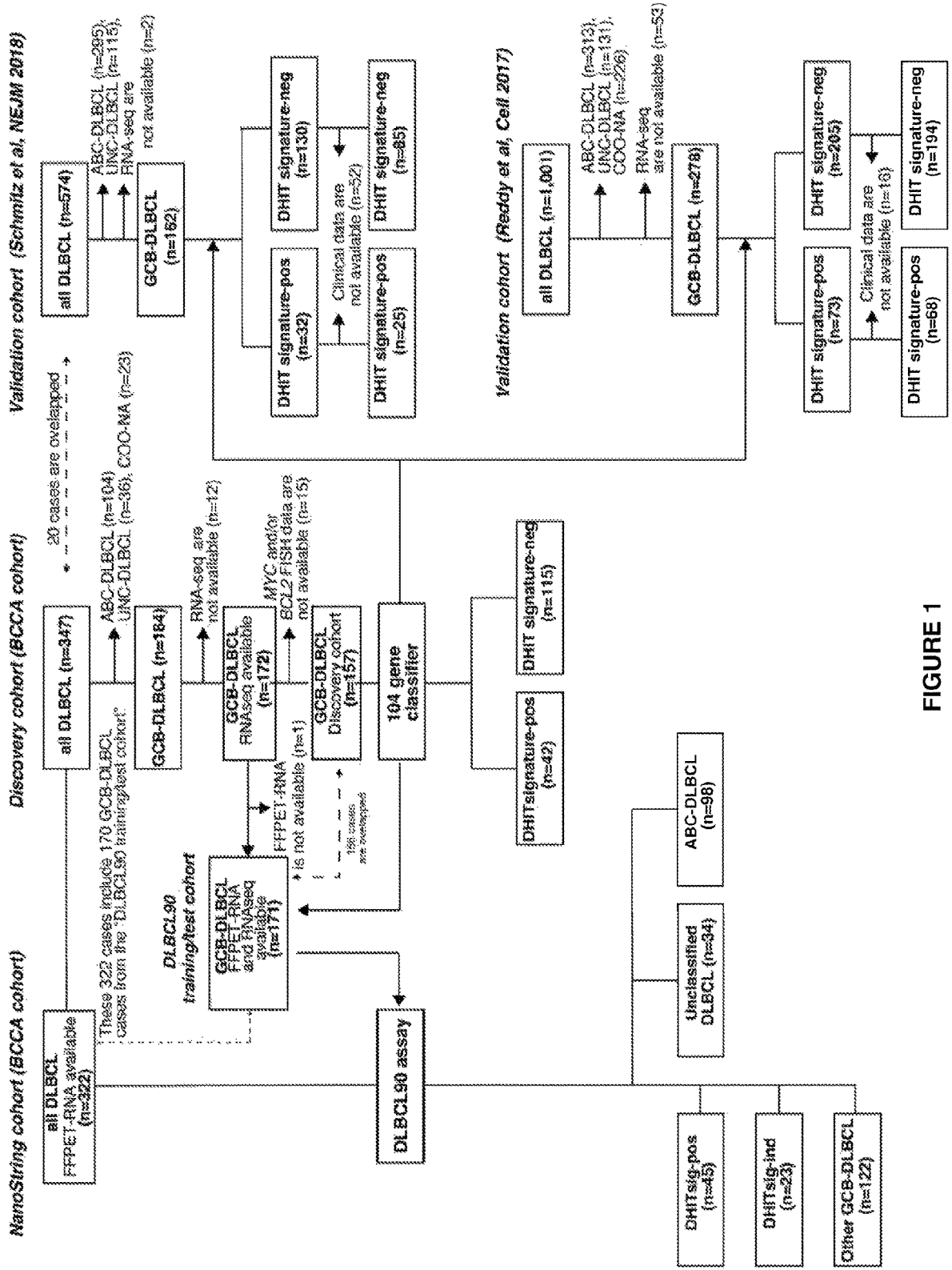
FIG. 1 shows the patient flow for the discovery cohort, two independent validation cohorts and NanoString cohort. ABC, activated B-cell-like subtype; GCB, germinal center B-cell-like subtypes; UNC, unclassified; DHIT, double-hit.

The present disclosure provides, in part, methods and reagents for classifying and identifying aggressive B-cell lymphomas. In alternative aspects, the present disclosure provides methods and reagents for selecting therapies and/or identifying candidates for therapies for aggressive B-cell lymphomas.

B-cell lymphomas can be diagnostically classified into Hodgkin and non-Hodgkin lymphomas. Most B-cell lymphomas are non-Hodgkin lymphomas and include Burkitt lymphoma, chronic lymphocytic leukemia/small lymphocytic lymphoma (CLL/SLL), diffuse large B-cell lymphoma, follicular lymphoma, mantle cell lymphoma, etc. Diffuse large B-cell lymphoma (DLBCL) is biologically heterogeneous. The WHO classification divides tumors with DLBCL morphology into cell-of-origin (COO) molecular subtypes: activated B-cell-like (ABC) and germinal center B-cell-like (GCB) subtypes and recognizes high-grade B-cell lymphoma with MYC and BCL2 and/or BCL6 rearrangements (HGBL-DH/TH) as including tumors with either DLBCL or high-grade morphology. Approximately 8% of tumors with DLBCL morphology are HGBL-DH/TH and all HGBL-DH/TH with BCL2 translocations (HGBL-DH/TH-BCL2) of DLBCL morphology belong to the GCB molecular subgroup. High grade B cell lymphoma (HGBL) is a heterogeneous entity with morphologic and genetic features intermediate between DLBCL and Burkitt lymphoma (BL) or blastoid morphology. Many patients with HGBL also have concurrent MYC, BCL2 and/or BCL6 rearrangements documented by FISH. HGBL without MYC and BCL2 and/or BCL6 have been termed HGBL-NOS. An "aggressive" B-cell lymphoma, as used herein, is a fast-growing non-Hodgkin lymphoma that is derived from a B lymphocyte.

In one aspect, the present disclosure provides a method of classifying an aggressive B-cell lymphoma by preparing a gene expression profile for two or more genes listed in any of Tables 1 to 4 from a test sample and classifying the test sample into two molecular subgroups: an aggressive B-cell lymphoma having a positive DHIT signature (DHITsig-pos) or an aggressive B-cell lymphoma having a negative DHIT signature (DHITsig-neg), based on the gene expression profile.

TABLE 1

|    | Gene Name    | ensembl_gene_id* |
|----|--------------|------------------|
| 1  | AC104699.1   | ENSG00000224220  |
| 2  | ACPP         | ENSG00000014257  |
| 3  | ADTRP        | ENSG00000111863  |
| 4  | AFMID        | ENSG00000183077  |
| 5  | ALOX5        | ENSG00000012779  |
| 6  | ALS2         | ENSG00000003393  |
| 7  | ANKRD33B     | ENSG00000164236  |
| 8  | ARHGAP25     | ENSG00000163219  |
| 9  | ARID3B       | ENSG00000179361  |
| 10 | ARPC2        | ENSG00000163466  |
| 11 | ASS1P1       | ENSG00000220517  |
| 12 | ATF4         | ENSG00000128272  |
| 13 | BATF         | ENSG00000156127  |
| 14 | BCL2A1       | ENSG00000140379  |
| 15 | CAB39        | ENSG00000135932  |
| 16 | CCDC78       | ENSG00000162004  |
| 17 | CCL17        | ENSG00000102970  |
| 18 | CCL22        | ENSG00000102962  |
| 19 | CD24         | ENSG00000272398  |
| 20 | CD80         | ENSG00000121594  |
| 21 | CDK5R1       | ENSG00000176749  |
| 22 | CFLAR        | ENSG00000003402  |
| 23 | COBLL1       | ENSG00000082438  |
| 24 | CPEB4        | ENSG00000113742  |
| 25 | CR2          | ENSG00000117322  |
| 26 | CTD-3074O7.5 | ENSG00000255517  |
| 27 | DANCR        | ENSG00000226950  |
| 28 | DGKG         | ENSG00000058866  |
| 29 | DOCK10       | ENSG00000135905  |
| 30 | EBI3         | ENSG00000105246  |
| 31 | EIF4EBP3     | ENSG00000243056  |
| 32 | ETV5         | ENSG00000244405  |
| 33 | FAM216A      | ENSG00000204856  |

TABLE 1-continued

| | Gene Name | ensembl_gene_id* |
|---|---|---|
| 34 | FCRL5 | ENSG00000143297 |
| 35 | FHIT | ENSG00000189283 |
| 36 | GALNT6 | ENSG00000139629 |
| 37 | GAMT | ENSG00000130005 |
| 38 | GNG2 | ENSG00000186469 |
| 39 | GPR137B | ENSG00000077585 |
| 40 | HAGHL | ENSG00000103253 |
| 41 | HIVEP1 | ENSG00000095951 |
| 42 | HMSD | ENSG00000221887 |
| 43 | HRK | ENSG00000135116 |
| 44 | IL10RA | ENSG00000110324 |
| 45 | IL21R | ENSG00000103522 |
| 46 | IRF4 | ENSG00000137265 |
| 47 | JCHAIN | ENSG00000132465 |
| 48 | LINC00957 | ENSG00000235314 |
| 49 | LRRC75A-AS1 | ENSG00000175061 |
| 50 | LTA | ENSG00000226979 |
| 51 | LY75 | ENSG00000054219 |
| 52 | MACROD1 | ENSG00000133315 |
| 53 | MIR155HG | ENSG00000234883 |
| 54 | MREG | ENSG00000118242 |
| 55 | MVP | ENSG00000013364 |
| 56 | MYC | ENSG00000136997 |
| 57 | MYEOV | ENSG00000172927 |
| 58 | NCOA1 | ENSG00000084676 |
| 59 | NMRAL1 | ENSG00000153406 |
| 60 | OR13A1 | ENSG00000256574 |
| 61 | PARP15 | ENSG00000173200 |
| 62 | PEG10 | ENSG00000242265 |
| 63 | PIK3CD-AS2 | ENSG00000231789 |
| 64 | POU3F1 | ENSG00000185668 |
| 65 | PPP1R14B | ENSG00000173457 |
| 66 | PTPRJ | ENSG00000149177 |
| 67 | QRSL1 | ENSG00000130348 |
| 68 | RASGRF1 | ENSG00000058335 |
| 69 | RFFL | ENSG00000092871 |
| 70 | RGCC | ENSG00000102760 |
| 71 | RPL13 | ENSG00000167526 |
| 72 | RPL35 | ENSG00000136942 |
| 73 | RPL6 | ENSG00000089009 |
| 74 | RPL7 | ENSG00000147604 |
| 75 | RPS8 | ENSG00000142937 |
| 76 | SEMA7A | ENSG00000138623 |
| 77 | SFXN4 | ENSG00000183605 |
| 78 | SGCE | ENSG00000127990 |
| 79 | SGPP2 | ENSG00000163082 |
| 80 | SIAH2 | ENSG00000181788 |
| 81 | SIGLEC14 | ENSG00000254415 |
| 82 | SLC25A27 | ENSG00000153291 |
| 83 | SLC29A2 | ENSG00000174669 |
| 84 | SMARCB1 | ENSG00000099956 |
| 85 | SMIM14 | ENSG00000163683 |
| 86 | SNHG11 | ENSG00000174365 |
| 87 | SNHG17 | ENSG00000196756 |
| 88 | SNHG19 | ENSG00000260260 |
| 89 | SNHG7 | ENSG00000233016 |
| 90 | SOX9 | ENSG00000125398 |
| 91 | SPTBN2 | ENSG00000173898 |
| 92 | ST8SIA4 | ENSG00000113532 |
| 93 | STAT3 | ENSG00000168610 |
| 94 | SUGCT | ENSG00000175600 |
| 95 | SYBU | ENSG00000147642 |
| 96 | TACC1 | ENSG00000147526 |
| 97 | TERT | ENSG00000164362 |
| 98 | TLE4 | ENSG00000106829 |
| 99 | TNFSF8 | ENSG00000106952 |
| 100 | UQCRH | ENSG00000173660 |
| 101 | VASP | ENSG00000125753 |
| 102 | VOPP1 | ENSG00000154978 |
| 103 | WDFY1 | ENSG00000085449 |
| 104 | WNK2 | ENSG00000165238 |

*Zerbino et al. Ensembl 2018. Nucleic Acids Res. 2018 Jan. 4; 46(D1): D754-D761. Gene annotations used by featureCounts for extracting read counts are from Ensembl gene build 87.

In an alternative aspect, an aggressive B-cell lymphoma can be classified by preparing or obtaining a gene expression product e.g., a molecule produced as a result of gene transcription, such as a nucleic acid or a protein, from a test sample, preparing or obtaining a gene expression profile for two or more genes listed in any of Tables 1 to 4 from the gene expression product and classifying the test sample into two molecular subgroups: an aggressive B-cell lymphoma having a positive DHIT signature (DHITsig-pos) or an aggressive B-cell lymphoma having a negative DHIT signature (DHITsig-neg), based on the gene expression profile.

In some embodiments, an aggressive B-cell lymphoma can be classified by determining the expression of two or more genes ("gene expression") listed in any of Tables 1 to 4 from a test sample, such as a cryosection of a fresh frozen biopsy or a formalin-fixed paraffin-embedded tissue (FFPET) biopsy prepared using standard techniques (see, e.g., Keirnan, J. (ed.), Histological and Histochemical Methods: Theory and Practice, 4th edition, Cold Spring Harbor Laboratory Press (2008)). Gene expression can be determined by isolating or otherwise analyzing a nucleic acid (such as RNA or DNA) from the test sample using standard techniques and commercially available reagents such as, without limitation, QIAamp DNA FFPE Tissue Kit, RNAEASY™ FFPE Kit, AllPREP FFPE Kit (Qiagen, Venlo, Netherlands); and MAGMAX™ FFPE DNA Isolation Kit (Life Technologies, Carlsbad, Calif.)).

In some embodiments, gene expression can be determined by isolating or otherwise analyzing a protein or polypeptide from the test sample using standard techniques and commercially available reagents such as, without limitation, immunohistochemistry techniques, ELISA, western blotting and mass spectrometry.

By "gene expression profile" or "signature" as used herein, is meant data generated from one or more genes listed in any of Tables 1 to 4 that make up a particular gene expression pattern that may be reflective of level of expression, cell lineage, stage of differentiation, or a particular phenotype or mutation. In some embodiments, a gene expression profile or signature includes data generated from two or more of the genes listed in Table 1 or 3, e.g., 2, 5, 10, 15, 20, 25, 30, 35, 40, 45, 50, 55, 60, 65, 60, 75, 80, 85, 90, 95, 100, or 104 of the genes listed in Tables 1 or 3. In some embodiments, a gene expression profile or signature includes data generated from two or more of the genes listed in Tables 2 or 4, e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the genes listed in Table 2 or 4. In some embodiments, a gene expression profile or signature includes data generated from all of the genes listed in Table 2 or 4. In some embodiments, a gene expression profile or signature includes data generated from substantially all of the genes listed in Table 2 or 4 e.g. 16, 17, 18, 19, 20, 21, 22, 23, 24, 25, 26, 27, 28, 29 or 30 of the genes listed in Table 2 or 4. In some embodiments, a gene expression profile or signature is "balanced" i.e. includes data generated from similar numbers of genes that are overexpressed and underexpressed as listed in any of Tables 1 to 4.

TABLE 2

| | Gene Name | Accession No. |
|---|---|---|
| 1 | AFMID | NM_001010982.4 |
| 2 | ALOX5 | NM_000698.2 |
| 3 | BATF | NM_006399.3 |
| 4 | CD24 | NM_013230.2 |
| 5 | CD80 | NM_005191.3 |
| 6 | CDK5R1 | NM_003885.2 |
| 7 | EBI3 | NM_005755.2 |
| 8 | GAMT | NM_138924.1 |

TABLE 2-continued

| | Gene Name | Accession No. |
|---|---|---|
| 9 | GPR137B | NM_003272.3 |
| 10 | IL21R | NM_021798.2 |
| 11 | IRF4 | NM_002460.1 |
| 12 | JCHAIN | NM_144646.3 |
| 13 | LY75 | NM_002349.2 |
| 14 | MIR155HG | NR_001458.3 |
| 15 | MYC | NM_002467.3 |
| 16 | OR13A1 | NM_001004297.2 |
| 17 | PEG10 | NM_001040152.1 |
| 18 | QRSL1 | NM_018292.2 |
| 19 | RFFL | NM_001017368.1 |
| 20 | RGCC | XM_011535051.1 |
| 21 | SEMA7A | NM_001146029.1 |
| 22 | SGPP2 | NM_152386.2 |
| 23 | SLC25A27 | NM_004277.4 |
| 24 | SMIM14 | NM_174921.1 |
| 25 | SNHG19 | NR_132114.1 |
| 26 | STAT3 | NM_003150.3 |
| 27 | SYBU | NM_001099744.1 |
| 28 | TNFSF8 | NM_001244.3 |
| 29 | VASP | NM_003370.3 |
| 30 | VOPP1 | NM_030796.3 |

A "gene expression profile" or "signature" can be prepared by generating data relating to the level of expression of two or more genes listed in in any of Tables 1 to 4, whether absolute or relative to a synthetic control or standard, in a sample, such as a biopsy sample. In some embodiments, the sample may be obtained from a subject prior to, during, or following diagnosis or treatment for an aggressive B-cell lymphoma, or to monitor the progression of an aggressive B-cell lymphoma, or to assess risk for development of an aggressive B-cell lymphoma, or to calculate risk of relapse. In some embodiments, a gene expression profile or signature can be prepared relative to a synthetic control to, for example, standardize lot-to-lot variation. The level of expression of a gene may be determined based on the level of a nucleic acid e.g., RNA, such as mRNA, encoded by the gene. Alternatively, level of expression of a gene may be determined based on the level of a protein or polypeptide or fragment encoded by the gene. In some embodiments, the gene expression data may be "digital," for example, based on the generation of sequence tags. In alternative embodiments, the gene expression data may be "analog," for example, based on hybridization of nucleic acids. Any suitable quantification method as described herein or known in the art can be used, such as without limitation, PCR, quantitative RT-PCR, real-time PCR, digital PCR, RNA amplification, in situ hybridization, immunohistochemistry, immunocytochemistry, FACS, SAGE, RNAseq, etc. In some embodiments, a gene expression profile can be prepared using microarrays, for example, nucleic acid or antibody microarrays. In some embodiments, a gene expression profile can be prepared with RNA gene expression data using the nCounter® gene expression assay available from NanoString Technologies, Inc. (Kulkami, M. M., "Digital Multiplexed Gene Expression Analysis Using the NANOSTRING™ NCOUNTER™ System," Current Protocols in Molecular Biology. 94: 25B.10.1-25B.10.17 (2011); Geiss et al., Nature Biotechnology, 26: 317-325 (2008); or U.S. Pat. No. 7,919,237).

In some embodiments, a gene expression profile can be prepared by generating data relating to the level of expression of Lymph3x genes, as set forth in Table 6 and described in PCT publication WO/2018/231589, Staudt et al., published Dec. 20, 2018, in addition to the two or more genes listed in in any of Tables 1 to 4. In some embodiments, a gene expression profile" can be prepared by generating data relating to the level of expression of BCL2, FCGR2B and/or PVT1, in addition to the two or more genes listed in in any of Tables 1 to 4 and/or Table 6.

In some embodiments, a gene expression profile can be prepared and classified as follows. Gene expression levels of two or more of the genes listed in Table 1 or 2 would be obtained from a sample using a suitable technology (for example, RNAseq or the NanoString platform). In one embodiment, using gene expression from RNAseq, the expression of the 104 genes from Table 1 can be inputted into an algorithm, for example:

$$DHITsig\ Score = \sum_{i=1}^{m} |Importance\ Score| * \left(\log_{10}\left(\frac{p_1}{p_2}\right)\right)$$

where m is the total number of 104 genes that can be matched in a given RNAseq data,
p1 is the p value based on t test of a given sample's gene expression value against a normal distribution with mean and standard deviation from DHITsig-pos group,
p2 is the p value based on t test of a given sample's gene expression value against a normal distribution with mean and standard deviation from DHITsig-neg group, and
the Importance Score are the values in Table 3,
to produce a score with an assignment made into the DHIT signature subgroups based on the score obtained, as described herein.

In another embodiment, using gene expression from the NanoString platform, the gene expression for the genes in Table 2, would be inputted into an algorithm, for example:

$$DHITsig\ Score = \sum_{i=1}^{m} Importance\ Score * gene\ expression$$

where m is the total number of genes (in this example, 30), the Importance Score are the values in Table 3, and gene expression is the gene expression of gene m, after the gene expression has been divided by the geometric mean of one or more (or all) of the house keeping genes (DNAJB12, GIT2, GSK3B, IK, ISY1, OPA1, PHF23, R3HDM1, TRIM56, UBXN4, VRK3, WAC and/or WDR55 listed in Table 6), multiplied by 1000 and $\log_2$ transformed,
to produce a score with an assignment made into the DHIT signature subgroups based on the score obtained, as described herein.

A "sample" can be a "test sample" and may be any organ, tissue, cell, or cell extract isolated from a subject, such as a sample isolated from a mammal having an aggressive B-cell lymphoma, or a subgroup or subtype of an aggressive B-cell lymphoma, such as a DLBCL, ABC-DLBCL, GCB-DLBCL, HGBL-DH/TH, HGBL-DH/TH-BCL2, HGBL-NOS, etc. For example, a sample can include, without limitation, cells or tissue (e.g., from a biopsy) or any other specimen, or any extract thereof, obtained from a patient (human or animal), test subject, or experimental animal. In some embodiments, it may be desirable to separate cancerous cells from non-cancerous cells in a sample. A sample may be from a cell or tissue known to be cancerous or suspected of being cancerous. Accordingly, a sample can include without limitation a cryosection of a fresh frozen biopsy, a formalin-fixed paraffin-embedded tissue (FFPET) biopsy, a cryopreserved diagnostic cell suspension, or peripheral blood.

As used herein, a "subject" may be a human, non-human primate, rat, mouse, cow, horse, pig, sheep, goat, dog, cat, etc. The subject may be a clinical patient, a clinical trial volunteer, an experimental animal, etc. The subject may be suspected of having or at risk for having an aggressive B-cell lymphoma or be diagnosed with an aggressive B-cell lymphoma. In some cases, the subject may have relapsed after treatment for a B-cell lymphoma, for example, treatment with rituximab, cyclophosphamide, doxorubicin hydrochloride, vincristine sulfate and prednisone (R-CHOP).

Gene expression profiles, prepared as described herein, can be used to classify an aggressive B-cell lymphoma into two molecular subgroups: an aggressive B-cell lymphoma having a positive DHIT signature (DHITsig-pos) or an aggressive B-cell lymphoma having a negative DHIT signature (DHITsig-neg). These molecular subgroups can be used for prognosis and/or to determine treatment options.

Accordingly, in an alternative aspect, the present disclosure provides a method for determining the prognosis of a subject diagnosed with an aggressive B-cell lymphoma by providing a gene expression profile for two or more genes listed in in any of Tables 1 to 4 from a test sample from the subject and classifying the test sample into an aggressive B-cell lymphoma subgroup having a positive DHIT signature (DHITsig-pos) or an aggressive B-cell lymphoma subgroup having a negative DHIT signature (DHITsig-neg) based on said gene expression profile, as described herein, where DHITsig-pos is predictive of a poor prognosis and DHITsig-neg is predictive of a good prognosis.

In some embodiments, prognosis or outcome may refer to overall or disease-specific survival, event-free survival, progression-free survival or outcome in response to a particular treatment or therapy. In some embodiments, the prognostic methods described herein may be used to predict the likelihood of long-term, disease-free survival i.e., that the subject will not suffer a relapse of the underlying aggressive B-cell lymphoma within a period of at least one year, or at least two years, or at least three years, or at least four years, or at least five years, or at least ten or more years, following initial diagnosis or treatment and/or will survive at least one year, or at least two years, or at least three years, or at least four years, or at least five years, or at least ten or more years, following initial diagnosis or treatment.

In some embodiments, the methods described herein can be used to screen tumors with DLBCL morphology for FISH testing, for example, for FISH testing for rearrangements involving MYC, BCL2 and/or BCL6.

In another aspect, the present disclosure provides a method for selecting a therapy, or for predicting a response to a therapy, for an aggressive B-cell lymphoma by determining whether the aggressive B-cell lymphoma has a positive DHIT signature (DHITsig-pos) or a negative DHIT signature (DHITsig-neg) as described herein; and selecting a therapy effective to treat the molecular subgroup thus determined.

In another aspect, the present disclosure provides a method for identifying a subject with an aggressive B-cell lymphoma for a therapy, or for predicting the response of a subject with an aggressive B-cell lymphoma to a therapy, by determining whether the aggressive B-cell lymphoma has a positive DHIT signature (DHITsig-pos) or a negative DHIT signature (DHITsig-neg) as described herein; and determining whether the candidate is likely to respond to a therapy effective to treat the molecular subgroup thus determined.

By "predicting the response of a subject with an aggressive B-cell lymphoma to a therapy" is meant assessing the likelihood that a subject will experience a positive or negative outcome with a particular treatment. As used herein, "indicative of a positive treatment outcome" refers to an increased likelihood that the subject will experience beneficial results from the selected treatment (e.g., complete or partial remission). "Indicative of a negative treatment outcome" is intended to mean an increased likelihood that the patient will not benefit from the selected treatment with respect to the progression and/or relapse of the underlying aggressive B-cell lymphoma.

Therapies for B-cell lymphoma include, without limitation, rituximab, cyclophosphamide, doxorubicin hydrochloride, vincristine sulfate and prednisone (R-CHOP), as well as alternate therapies, such as a dose intensive immunochemotherapy, a cell-based therapy such as CAR T-cell therapy, a BCL2 inhibitor, an enhancer of zeste homolog 2 (EZH2) inhibitor, a histone deacetylase inhibitor, arachidonate 5-lipoxygenase inhibitor, a Bruton's tyrosine kinase inhibitor (such as ibrutinib), a PIM kinase inhibitor (such as SGI-1776), a histone deacetylase inhibitor (such as belinostat or vorinostat), a PI3K inhibitor (such as copanlisib or buparlisib), a protein kinase C inhibitor (such as sotrastaurin), immunomodulatory drugs (IMiD—such as lenalidomide) newer generation anti-CD20 antibodies, etc.

In some embodiments, when the molecular subgroup is determined to be DHITsig-neg, the therapy can be rituximab, cyclophosphamide, doxorubicin hydrochloride, vincristine sulfate and prednisone (R-CHOP).

In some embodiments, when the molecular subgroup is determined to be DHITsig-pos, a therapy other than R-CHOP (an alternate therapy) may be selected.

In another aspect, the present disclosure provides a kit comprising reagents sufficient for the detection of two or more of the genes listed in any of Tables 1 to 4. In some embodiments, the kits may further include reagents sufficient for the detection or two or more of the genes listed in Tables 5 or 6. The kit may be used for classification of an aggressive B-cell lymphoma and/or for providing prognostic information and/or for providing information to assist in selection of a therapy.

The kit may include probes and/or primers specific to two or more of the genes listed in any of Tables 1 to 4 as well as reagents sufficient to facilitate detection and/or quantification of the gene expression products. In some embodiments, the kits may further include probes and/or primers specific to one or more of the genes listed in Tables 5 or 6. The kit may further include a computer readable medium.

The present invention will be further illustrated in the following examples.

EXAMPLES

Methods

Patient Cohort Description

We analyzed RNAseq data from 157 de novo GCB DLBCLs, including 25 HGBL-DH/TH-BCL2, to define gene expression differences between HGBL-DH/TH-BCL2 and other GCB-DLBCLs (discovery cohort). These are GCB-DLBCLs with available MYC and BCL2 FISH results from a cohort of 347 diagnostic biopsies of de novo DLBCL patients treated with R-CHOP who were selected from the BC Cancer population-based registry[6] (FIG. 1). This study was reviewed and approved by the University of British Columbia-BC Cancer Research Ethics Board, in accordance with the Declaration of Helsinki.

We utilized two external cohorts with RNAseq data available (Reddy et al; n=278 GCB-DLBCL cases, Schmitz et al; n=162 GCB-DLBCL cases) to explore the prognostic significance and molecular features associated with DHITsig DLBCL[18, 19] FFPE biopsies of 322 of the 347 DLBCLs plus 88 transformed follicular lymphomas (tFL)[20] with DLBCL morphology and 26 high-grade B-cell lymphomas (HGBL) from patients treated in BC were analyzed for the validation of the NanoString assay.

Gene Expression Profiling and Mutational Analysis

RNAseq was applied to RNA extracted from fresh frozen biopsies. We compiled mutations from targeted sequencing of the discovery cohort and existing exome data from two validation cohorts, each with matched RNAseq[18, 19]. Sample processing of RNA and DNA, library construction and detailed analytic procedures for RNAseq, targeted resequencing and mutational analysis of exome data were either previously described[6, 21-23], or are described herein.

Phenotypic Analysis

Sample Processing of Fresh Frozen Biopsies

For genetic analyses performed at BC Cancer, genomic DNA and RNA were extracted using the AllPrep DNA/RNA Mini kit (QIAGEN, Germany) according to the manufacturer's instructions from cryosections of fresh frozen biopsies or from cryopreserved diagnostic cell suspensions. For constitutional DNA, we extracted genomic DNA from peripheral blood using the Gentra Puregene Blood Kit (QIAGEN).

IHC and FISH Analyses on Tissue Microarray

Immunohistochemistry (IHC) and fluorescent in situ hybridization (FISH) was performed on formalin-fixed paraffin-embedded tissue (FFPET) biopsies of 341 DLBCL cases within the cohort as described previously[6, 24]. Briefly, FISH was performed using commercially available dual-color break-apart probes for MYC, BCL2 and BCL6 as previously described[6, 24]. IHC staining on the 4 µm slides of TMAs was performed for MYC, BCL2, CD10 (MME), BCL6, MUM1 (IRF4) and Ki67 on the Benchmark XT platform (Ventana, Ariz.) according to the previously described method[6, 24]. For CD10, BCL6 and MUM1 (IRF4), tumor cells with >30% positive cells were called as positive. The cut-off points previously described were used for MYC (≥40% positive tumor cells) and BCL2 (≥50% positive tumor cells)[9].

Lymph2Cx Assay

For the determination of COO subtype of BC-Cancer cohort, digital GEP was performed using the Lymph2Cx 20-genes GEP assay on the NanoString platform (NanoString Technologies, WA)[24, 32]. RNA was extracted from 10 µm scrolls using the QIAGEN AllPrep DNA/RNA FFPE kit (Catalogue #80234, QIAGEN GmbH, Germany) with QIAGEN deparaffinization solution (Catalogue #19093, QIAGEN GmbH, Germany). Two hundred nanograms of RNA were used to quantitate the 20 genes that contribute to the Lymph2Cx assay. The reactions were processed on an nCounter™ Prep Station. The COO score was calculated based on the model previously described[32] and assigned to ABC, GCB and Unclassified categories.

Flow Cytometry Analysis

We performed flow cytometric immunophenotyping on cell suspensions from freshly disaggregated lymph node biopsies using a routine diagnostic panel and stained according to the manufacturer's recommendations with CD3, CD4 and CD8 monoclonal antibodies (Beckman Coulter, USA). Analysis was performed on a Cytomics FC 500 flow cytometer (samples processed between 1985-2009; Beckman Coulter, USA) or BD FACS Canto (samples processed between 2009-2011; BD Biosciences, USA).

Gene Expression Analysis

Library Preparation and Data Processing of RNAseq

RNA-seq data were generated from 322 BC-Cancer DLBCL samples to quantify the gene expression levels. Polyadenylated (polyA+) messenger RNA (mRNA) was purified using the 96-well MultiMACS mRNA isolation kit on the MultiMACS 96 separator (Miltenyi Biotec, Germany) then ethanol-precipitated, and used to synthesize cDNA using the Maxima H Minus First Strand cDNA Synthesis kit (Thermo-Fisher, USA) and random hexamer primers at a concentration of 5 µM along with a final concentration of 1 µg/uL Actinomycin D, followed by Ampure XP SPRI bead purification on a Biomek FX robot (Beckman-Coulter, USA). cDNA was fragmented by sonication using a Covaris LE220 (Covaris, USA). Plate-based libraries were prepared using the Biomek FX robot (Beckman-Coulter, USA) according to the British Columbia Cancer, Genome Science Centre paired-end protocol, previously described[33]. The purified libraries with a desired size range were purified and diluted to 8 nM, and then pooled at five per lane and sequenced as paired-end 75-bp on the Hiseq 2500 platform. This yielded, on average, 71 million reads per patient (range: 6.5-163.7 million reads).

Paired end RNA-seq FASTQ files were used as input to our gene expression analyses starting with alignment using the STAR aligner (STAR_2.5.1b_modified). The non-default parameters were chosen as recommended by the STAR-Fusion guidelines as follows: --outReadsUnmapped None, --twopassMode Basic, --outSAMunmapped Within. Detailed data analysis was as previously described[21-23].

104 Gene DHIT Signature

In order to produce a stable significant gene list, RNAseq count data were normalized in two different ways: voom function in R package limma and vst function in R package DESeq2. DESeq2 was used to normalize the data using variant stabilization. We generated spearman correlation coefficients and Importance Gini Index from a random forest analysis for both data formats to identify genes that discriminated HGBL-DH/TH-BCL2 from other GCB-DLBCLs. For each gene, we derived four "importance scores", namely two correlation coefficients and two Importance Gini Indexes with signs of correlation coefficients. The mean of the four numbers became final Importance Score for each gene. We kept the top 0.1% and down 0.1% genes with the largest absolute Importance Score, removing any genes where the 95% confidence intervals, based on these four importance scores, crossed 0. Additionally, genes with BAC-based names (RP1 and RP11) were removed. This process resulted in identifying the 104 genes (Table 3).

TABLE 3

DHITsignature Importance Score

| No. | Gene Name | DHITsignature Importance Score |
| --- | --- | --- |
| 1* | OR13A1 | 0.674218428 |
| 2 | FAM216A | 0.666273573 |
| 3* | MYC | 0.618096768 |
| 4* | SLC25A27 | 0.597328882 |
| 5* | ALOX5 | 0.58228409 |
| 6 | UQCRH | 0.554550411 |
| 7 | SUGCT | 0.544791009 |
| 8 | SNHG7 | 0.533131106 |
| 9* | TNFSF8 | 0.486553751 |
| 10 | LINC00957 | 0.477482138 |

TABLE 3-continued

DHITsignature Importance Score

| No. | Gene Name | DHITsignature Importance Score |
|---|---|---|
| 11* | PEG10 | 0.47567559 |
| 12 | PIK3CD-AS2 | 0.471364846 |
| 13* | GAMT | 0.460818809 |
| 14 | RPL6 | 0.450222225 |
| 15 | EIF4EBP3 | 0.44958096 |
| 16* | SNHG19 | 0.43230419 |
| 17* | QRSL1 | 0.428096281 |
| 18 | FHIT | 0.427190221 |
| 19 | SLC29A2 | 0.426164929 |
| 20 | TERT | 0.425033659 |
| 21 | SMARCB1 | 0.425002411 |
| 22* | RGCC | 0.420393779 |
| 23 | SNHG17 | 0.415383434 |
| 24* | JCHAIN | 0.411205299 |
| 25 | SPTBN2 | 0.405165754 |
| 26 | ATF4 | 0.404262821 |
| 27* | CD24 | 0.402431294 |
| 28 | RPL35 | 0.401009226 |
| 29 | HAGHL | 0.394797818 |
| 30 | CTD-3074O7.5 | 0.394296803 |
| 31 | WNK2 | 0.388330521 |
| 32* | AFMID | 0.387741681 |
| 33 | CCDC78 | 0.385406868 |
| 34 | RPL13 | 0.380647502 |
| 35 | RPL7 | 0.379759418 |
| 36 | SFXN4 | 0.378277224 |
| 37 | SGCE | 0.377273747 |
| 38* | SMIM14 | 0.376756114 |
| 39 | LRRC75A-AS1 | 0.374634245 |
| 40 | HRK | 0.37333362 |
| 41 | DANCR | 0.369704472 |
| 42* | SYBU | 0.368491881 |
| 43 | RPS8 | 0.366455454 |
| 44 | SNHG11 | 0.361898633 |
| 45 | NMRAL1 | 0.361333845 |
| 46 | PPP1R14B | 0.361300092 |
| 47 | MACROD1 | 0.358735977 |
| 48 | SOX9 | 0.357910791 |
| 49 | MYEOV | −0.433195192 |
| 50 | IL10RA | −0.434099608 |
| 51* | GPR137B | −0.436646932 |
| 52 | TLE4 | −0.438088957 |
| 53 | PARP15 | −0.439442144 |
| 54 | CCL17 | −0.44087649 |
| 55 | HMSD | −0.442821817 |
| 56 | DOCK10 | −0.442933644 |
| 57 | MVP | −0.444564212 |
| 58 | ASS1P1 | −0.446234544 |
| 59 | GNG2 | −0.446254755 |
| 60* | CDK5R1 | −0.450417206 |
| 61 | ETV5 | −0.452152489 |
| 62 | RASGRF1 | −0.452864227 |
| 63 | ACPP | −0.453427316 |
| 64 | COBLL1 | −0.463624343 |
| 65* | LY75 | −0.465397796 |
| 66 | ARPC2 | −0.465449467 |
| 67 | CFLAR | −0.46969468 |
| 68 | AC104699.1 | −0.470363948 |
| 69 | GALNT6 | −0.476351522 |
| 70* | VASP | −0.478206272 |
| 71 | ARHGAP25 | −0.483174276 |
| 72 | SIGLEC14 | −0.485514467 |
| 73 | PTPRJ | −0.490756177 |
| 74 | CR2 | −0.492801851 |
| 75 | CAB39 | −0.493964596 |
| 76 | HIVEP1 | −0.503485196 |
| 77* | RFFL | −0.509848773 |
| 78 | ADTRP | −0.515183922 |
| 79* | MIR155HG | −0.515576659 |
| 80 | POU3F1 | −0.517296363 |
| 81* | VOPP1 | −0.51791333 |
| 82* | BATF | −0.518200838 |
| 83 | MREG | −0.520592143 |
| 84* | STAT3 | −0.52803111 |
| 85 | TACC1 | −0.530782224 |
| 86* | IRF4 | −0.53144132 |
| 87 | ST8SIA4 | −0.53144637 |
| 88 | WDFY1 | −0.532489998 |
| 89 | ARID3B | −0.533035852 |
| 90 | CCL22 | −0.536215245 |
| 91 | SIAH2 | −0.537210723 |
| 92* | SGPP2 | −0.578055021 |
| 93 | CPEB4 | −0.582615014 |
| 94* | CD80 | −0.591988047 |
| 95* | SEMA7A | −0.597132928 |
| 96 | ANKRD33B | −0.601972432 |
| 97 | NCOA1 | −0.602464735 |
| 98 | BCL2A1 | −0.623793977 |
| 99 | DGKG | −0.633290788 |
| 100 | ALS2 | −0.657454773 |
| 101 | LTA | −0.673264157 |
| 102 | FCRL5 | −0.750221729 |
| 103* | EBI3 | −0.776792921 |
| 104* | IL21R | −0.778158195 |

*selected for DLCBL90 assay

To calculate the 104 gene DHITsig score for RNAseq data, we used the following model:

$$DHITsig\ Score = \sum_{i=1}^{m} |Importance\ Score| * \left(\log_{10}\left(\frac{p_1}{p_2}\right)\right)$$

where m is the total number of 104 genes that we can match in a given RNAseq data, p1 is the p value based on t test of a given sample's gene expression value against a normal distribution with mean and standard deviation from DHITsig-pos group, and p2 is the p value based on t test of a given sample's gene expression value against a normal distribution with mean and standard deviation from DHITsig-neg group, When training data with DHITsig information was not available, such as testing on an independent cohort, we used a prior of proportion of DHITsig-pos cases for a given gene to calculate the mean and standard deviation for DHITsig-pos group, with the remaining values used to calculate mean and standard deviation for the DHITsig-negative group.

GSEA

Differentially expressed genes between DHITsig-pos and DHITsig-neg were determined using DESeq2 v.1.20.0[34]. The DESeq pipeline was run using the default parameters, aside from the results, during which the following parameters were set, lfcThreshold=0.5, and alpha=0.1. The resulting differentially expressed genes and their combined test statistics were then used as input for Fast Gene Set Enrichment Analysis v.1.6.0 (FGSEA)[35]. The hallmark gene sets, gene symbols (h.all.v6.2.symbols.gmt) used for FGSEA analysis were obtained from MSigDB/GSEA. FGSEA was then run using 1000 permutations, with the aforementioned gene list, test statistics, and hallmark gene set as input.

Based on DZ/IZ/LZ gene lists[26], we selected top 20 genes for each of these lists and extra RNAseq data for these 60 genes for the discovery DLC GCB cohort with 157 samples. For each gene, we calculated z score across all 157 samples. For each sample, we further calculated mean z scores for 20 DZ genes, 20 IZ genes, and 20 LZ genes separately. Then, we separated 157 samples into DHITsig-pos and DHITsig-neg, and compare their median sample mean z score differences between DHITsig POS vs NEG for DZ, IZ and LZ separately based on Wilcoxon rank sum test (also called Mann-Whitney' test for two group comparison). Boxplot showed DZ, IZ, LZ separately with DHITsig-pos and -neg. P values on the boxplot were from Wilcoxon rank sum test.

Mutation Analysis

We analyzed the data of targeted re-sequencing, which has been performed using BC Cancer cohort. A gene panel comprising known DLBCL-related genes and novel candidates was sequenced in tumor DNA extracted from FF biopsies in 347 de novo DLBCL patients using a TruSeq Custom Amplicon and custom hybridisation-capture strategy as described previously[6, 21-23].

Statistical Analysis

The Kaplan-Meier method was used to estimate the time-to-progression (TTP; progression/relapse or death from lymphoma or acute treatment toxicity), progression-free survival (PFS; progression/relapse or death from any cause), disease-specific survival (DSS; death from lymphoma or acute treatment toxicity) and overall survival (OS; death from any cause), with log-rank test performed to compare groups. Univariate and multivariate Cox proportional hazard models were used to evaluate proposed prognostic factors.

Fisher's exact test was used when comparing two categorical data. For the comparison of two continuous variables, data were tested by Wilcoxon rank-sum test, except where noted. Multiple testing correction was performed, where necessary, using the Benjamini-Hochberg procedure. All P values result from two-sided tests and a threshold of 0.05 was used for significance, except where noted. All analyses were performed using R v3.4.1.

Digital Gene Expression Profiling

To translate the signature into an assay applicable to FFPE, we performed digital expression profiling on RNA derived from FFPE biopsies using the NanoString Technology (Seattle, Wash.) as described herein.

Development and Testing of the DLBCL90 Digital Gene Expression

RNA was extracted from formalin-fixed paraffin-embedded (FFPE) biopsies using the Qiagen AllPrep DNA/RNA FFPE Kit (Qiagen, Hilden, Germany). Digital gene expression was performed on the NanoString technology platform at the highest resolution (555 fields of view).

Data was normalized for loading and RNA integrity by dividing by the geometric mean of the housekeeping genes for that sample and then multiplying by 1000. The housekeeping genes were the 13 genes used in the Lymph3Cx assay and includes all 5 genes from the Lymph2Cx[27]. The normalized data was then $\log_2$ transformed prior to analysis.

Model Building

Gene Selection

Figure 2:
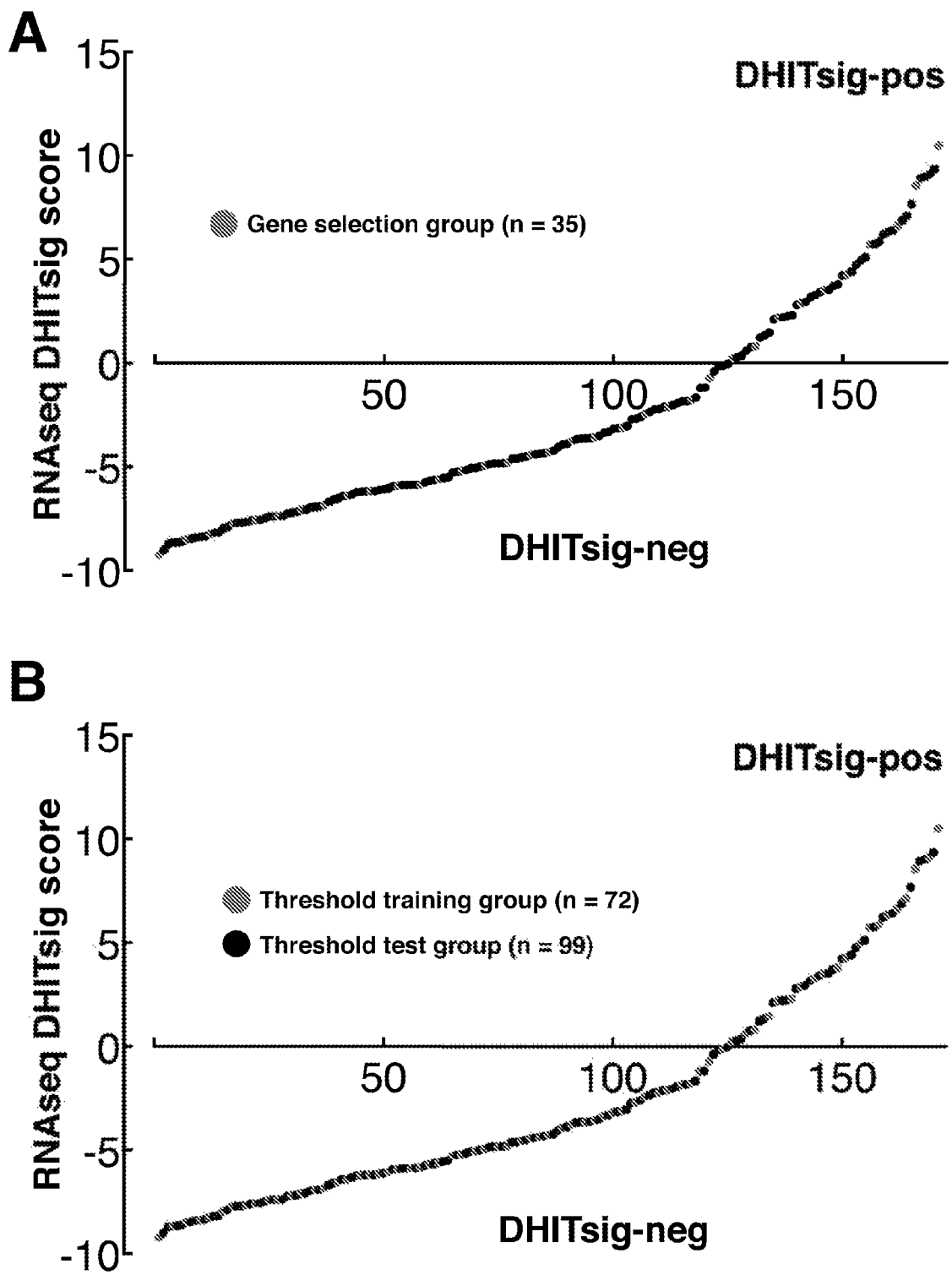
FIG. 2A shows the RNAseq DHITsig scores from 171 GCB-DLBCL used to train and test the DLBCL90 assay. The tumors are arrayed from left to right with increasing DHITsig scores with tumors with a score below 0 being designated DHITsig-neg and above 0 being DHITsig-pos. Selected tumors had digital expression performed using a codeset that contained all 104 genes in the RNAseq model.
FIG. 2B shows the RNAseq DHITsig scores from 171 GCB-DLBCL used to train and test the DLBCL90 assay. The tumors are arrayed from left to right with increasing DHITsig scores with tumors with a score below 0 being designated DHITsig-neg and above 0 being DHITsig-pos. Selected tumors were used to "train" the threshold for the DLBCL90 assay.

In order to translate the DHITsig from RNAseq to the NanoString platform, digital gene expression was first performed using a code set that included all 104 gene of the RNAseq DHITsig. This was applied to 35 samples that were selected to be representative of the range of scores observed with the RNAseq model (FIG. 2A). In the first step, the correlation between gene expression by RNAseq and NanoString in these 35 samples was examined. Genes with $R^2$ less than 0.6 were excluded leaving 67 genes of interest. These 67 genes were then ranked into two lists ordered according to their Importance Score: A) genes over-expressed in DHITsig-pos tumors and B) genes under-expressed in DHITsig-pos. In order to produce a "balanced" model, that would be less vulnerable to any variability in normalization, the 15 top ranked genes from both lists were selected for the final model (see Table 2 or 4).

Model Building

A NanoString codeset was developed that included the 30 selected genes alongside the genes in the Lymph3Cx—this represented an additional of 29 genes as IRF4 was already included in the Lymph3Cx. The Lymph3Cx included the 20 genes from the Lymph2Cx in addition to 8 further housekeeper genes and 30 genes that discriminate DLBCL from primary mediastinal B-cell lymphoma[12]. The Lymph3Cx genes are listed, for example, in PCT publication WO/2018/231589, Staudt et al., published Dec. 20, 2018. In addition, BCL2, FCGR2B and PVT1 were added for a total of 90 genes, with the assay named "DLBCL90". The probes targeting the 30 selected genes were used in the NanoString assay (Table 4). The probes targeting BCL2, FCGR2B and PVT1, used in the NanoString assay, are shown in Table 5.

TABLE 4

| | Gene Name | Accession | Position | Target Sequence |
|---|---|---|---|---|
| 1 | AFMID | NM_001010982.4 | 851-950 | AGTGGAAAGCCTCATTTGAAGAG CTCCACGATGTGGACCACTTTGAA GACAACGTGCTCACCCAGATTATC TTGAA (SEQ ID NO: 1) |
| 2 | ALOX5 | NM_000698.2 | 736-835 | GTCAAGATCAGCAACACTATTTCT GAGCGGGTCATGAATCACTGGCA GGAAGACCTGATGTTTGGCTACC AGTTCCTGAATGGCTGCAACCCT GTGTTGA (SEQ ID NO: 2) |
| 3 | BATF | NM_006399.3 | 826-925 | CACTGTGGGTTGCAGGCCCAATG CAGAAGAGTATTAAGAAAGATGCT CAAGTCCCATGGCACAGAGCAAG GCGGGCAGGGAACGGTTATTTTT CTAAATA (SEQ ID NO: 3) |
| 4 | CD24 | NM_013230.2 | 1860-1959 | ATAGACACTCCCCGAAGTCTTTTG TTCGCATGGTCACACACTGATGCT TAGATGTTCCAGTAATCTAATATG GCCACAGTAGTCTTGATGACCAAA GTCC (SEQ ID NO: 4) |

TABLE 4-continued

| | Gene Name | Accession | Position | Target Sequence |
|---|---|---|---|---|
| 5 | CD80 | NM_005191.3 | 675-774 | GATATCACTAATAACCTCTCCATTGTGATCCTGGCTCTGCGCCCATCTGACGAGGGCACATACGAGTGTGTTGTTCTGAAGTATGAAAAAGACGCTTTCA (SEQ ID NO: 5) |
| 6 | CDK5R1 | NM_003885.2 | 1211-1310 | TTTGTGTACAGTATGTGTCTAGCAAAGCCACCAAGGGCCTCACCTTTCCCACAGTCTCTCCCTGGGGTTTTTTTCATCCCTGCCAAGAACTCTGGGCACT (SEQ ID NO: 6) |
| 7 | EBI3 | NM_005755.2 | 827-926 | CCGGGCAACCTCAGATGACCGACTTTTCCCTTTGAGCCTCAGTTTCTCTAGCTGAGAAATGGAGATGTACTACTCTCTCCTTTACCTTTACCTTTACCAC (SEQ ID NO: 7) |
| 8 | GAMT | NM_138924.1 | 291-390 | GCCATCGCAGCGTCAAAGGTGCAGGAGGCGCCCATTGATGAGCATTGGATCATCGAGTGCAATGACGGCGTCTTCCAGCGGCTCCGGGACTGGGCCCCAC (SEQ ID NO: 8) |
| 9 | GPR137B | NM_003272.3 | 682-781 | TAATGACACGCTCTTCGTGCTGTGTGCCGTCTCTCTCTCCATCTGTCTCTACAAAATCTCTAAGATGTCCTTAGCCAACATTTACTTGGAGTCCAAGGGC (SEQ ID NO: 9) |
| 10 | IL21R | NM_021798.2 | 2081-2180 | CGTGTTTGTGGTCAACAGATGACAACAGCCGTCCTCCCTCCTAGGGTCTTGTGTTGCAAGTTGGTCCACAGCATCTCCGGGGCTTTGTGGGATCAGGGCA (SEQ ID NO: 10) |
| 11 | IRF4 | NM_002460.1 | 326-425 | GGGCACTGTTTAAAGGAAAGTTCCGAGAAGGCATCGACAAGCCGGACCCTCCCACCTGGAAGACGCGCCTGCGGTGCGCTTTGAACAAGAGCAATGACTT (SEQ ID NO: 11) |
| 12 | JCHAIN | NM_144646.3 | 436-535 | GTGGAGCTGGATAATCAGATAGTTACTGCTACCCAGAGCAATATCTGTGATGAAGACAGTGCTACAGAGACCTGCTACACTTATGACAGAAACAAGTGCT (SEQ ID NO: 12) |
| 13 | LY75 | NM_002349.2 | 5362-5461 | GATCTTAGGCATGTGCTGGTATCCACAGTTAATTCCCTGCTAAATGCCATGTTTATCACCCTAATTAATAGAATGGAGGGGACTCCAAAGCTGGAACTGA (SEQ ID NO: 13) |
| 14 | MIR155HG | NR_001458.3 | 361-460 | CTGTTACTAGCATTCACATGGAACAAATTGCTGCCGTGGGAGGATGACAAAGAAGCATGAGTCACCCTGCTGGATAAACTTAGACTTCAGGCTTTATCAT (SEQ ID NO: 14) |
| 15 | MYC | NM_002467.3 | 1611-1710 | TCGGACACCGAGGAGAATGTCAAGAGGCGAACACACAACGTCTTGGAGCGCCAGAGGAGGAACGAGCTAAAACGGAGCTTTTTTGCCCTGCGTGACCAGA (SEQ ID NO: 15) |
| 16 | OR13A1 | NM_001004297.2 | 917-1016 | TGCTTCTCTCCTGCAGCTCCACCTACGTCAACGGTGTCATGATTGTCCTGGCGGATGCTTTCTACGGCATAGTGAACTTCCTGATGACCATCGCGTCCTA (SEQ ID NO: 16) |

TABLE 4-continued

| | Gene Name | Accession | Position | Target Sequence |
|---|---|---|---|---|
| 17 | PEG10 | NM_001040152.1 | 5001-5100 | TTTGCCACCACTGCAAGCAAAAGT CTGGAGAAGTTCACCAACGACAA GAACGATTAGGGAAAATATGCTG CTGTGGGTTAACAACTCAGAAAGT CCCTGA (SEQ ID NO: 17) |
| 18 | QRSL1 | NM_018292.2 | 1131-1230 | GATGGGCTACAATATGGTCACAG ATGTGACATTGATGTGTCCACTGA AGCCATGTATGCTGCAACCAGAC GAGAAGGATTTAATGATGTGGTGA GAGGAA (SEQ ID NO: 18) |
| 19 | RFFL | NM_001017368.1 | 509-608 | TCTCAGCCTCCATGACATCTCTAC CGAAATGTGCCGGGAGAAAGAAG AGCTGGTGCTCTTGGTCCTTGGC CAGCAGCCTGTAATCTCCCAGGA GGACAGG (SEQ ID NO: 19) |
| 20 | RGCC | XM_011535051.1 | 381-480 | GTCGGACGCGCTGTGCGAGTTTG ACGCGGTGCTGGCCGACTTCGCG TCGCCCTTCCACGAGCGCCACTT CCACTACGAGGAGCACCTGGAGC GCATGAAG (SEQ ID NO: 20) |
| 21 | SEMA7A | NM_001146029.1 | 661-760 | CCCACAGTTCATCAAAGCCACCAT CGTGCACCAAGACCAGGCTTACG ATGACAAGATCTACTACTTCTTCC GAGAGGACAATCCTGACAAGAAT CCTGAG (SEQ ID NO: 21) |
| 22 | SGPP2 | NM_152386.2 | 851-950 | GGGCTGGAGTGACCATAGGATTC TGGATCAACCATTTCTTCCAGCTT GTATCCAAGCCCGCTGAATCTCTC CCTGTTATTCAGAACATCCCACCA CTCAC (SEQ ID NO: 22) |
| 23 | SLC25A27 | NM_004277.4 | 1481-1580 | CCGCACAGCATTTTCTAAAGAAGA ATCGAAGCCTGACCACTTTCACCT TGGGCAAGAAGGTTTGGCCTTTG AGTTGCTATTCTATGCTGAAGAGC CTGCT (SEQ ID NO: 23) |
| 24 | SMIM14 | NM_174921.1 | 371-470 | ACCTCCTAATCTAAGAGGATCCAG CCTACCTGGAAAGCCAACCAGTC CTCATAATGGACAAGATCCACCAG CTCCTCCTGTGGACTAACTTTGTG ATATG (SEQ ID NO: 24) |
| 25 | SNHG19 | NR_132114.1 | 235-334 | TGCAAGTTTTGAACCTAAGTAAAC CTCAATCCGGAGGGCCTAGCGGT AAGGTGGGCGCTGTGTCTATTGA AGTGCTTAGCAATAAAGAAAGGTA GTGAGT (SEQ ID NO: 25) |
| 26 | STAT3 | NM_003150.3 | 2061-2160 | AAAGAAGGAGGCGTCACTTTCAC TTGGGTGGAGAAGGACATCAGCG GTAAGACCCAGATCCAGTCCGTG GAACCATACACAAAGCAGCAGCT GAACAACA (SEQ ID NO: 26) |
| 27 | SYBU | NM_001099744.1 | 1493-1592 | CACTCAAAGAAGCCAGGAAAGAG ATTAAACAGCTCAAACAGGTCATC GAAACCATGCGGAGCAGCTTGGC TGATAAAGATAAAGGCATTCAGAA ATATTT (SEQ ID NO: 27) |
| 28 | TNFSF8 | NM_001244.3 | 519-618 | CCCTCAAAGGAGGAAATTGCTCA GAAGACCTCTTATGTATCCTGAAA AGGGCTCCATTCAAGAAGTCATG GGCCTACCTCCAAGTGGCAAAGC ATCTAAA (SEQ ID NO: 28) |

TABLE 4-continued

| | Gene Name | Accession | Position | Target Sequence |
|---|---|---|---|---|
| 29 | VASP | NM_003370.3 | 1501-1600 | AGACCCGCTTCTCCTTTCCGCACACCCGGCCTGTCACCCTGCTTTCCCTGCCTCTACTTGACTTGGAATTGGCTGAAGACTACACAGGAATGCATCGTTC (SEQ ID NO: 29) |
| 30 | VOPP1 | NM_030796.3 | 2091-2190 | GAGCCTCTTGAGAAATTGTTACTCATTGAACTGGAGCATCAAGACATCTCATGGAAGTGGATACGGAGTGATTTGGTGTCCATGCTTTTCACTCTGAGGA (SEQ ID NO: 30) |

TABLE 5

| | Gene Name | Accession | Position | Target Sequence |
|---|---|---|---|---|
| 1 | BCL2 | NM_000657.2 | 948-1047 | AGTTCGGTGGGGTCATGTGTGTGGAGAGCGTCAACCGGGAGATGTCGCCCCTGGTGGACAACATCGCCCTGTGGATGACTGAGTACCTGAACCGGCACCT (SEQ ID NO: 31) |
| 2 | FCGR2B | NM_001002273.1 | 871-970 | AGGCTGACAAAGTTGGGGCTGAGAACACAATCACCTATTCACTTCTCATGCACCCGGATGCTCTGGAAGAGCCTGATGACCAGAACCGTATTTAGTCTCC (SEQ ID NO: 32) |
| 3 | PVT1 | NR_003367.1 | 412-511 | GATGGCTGTGCCTGTCAGCTGCATGGAGCTTCGTTCAAGTATTTTCTGAGCCTGATGGATTTACAGTGATCTTCAGTGGTCTGGGGAATAACGCTGGTGG (SEQ ID NO: 33) |

TABLE 6

| | Gene | Accession No. | Position | Target Sequence |
|---|---|---|---|---|
| 1 | ASB13 | NM_024701.3 | 1636-1735 | GGACACGTAGGCGGTACCACTAAGGTTTTGGTAATGAGCCATTCAAACCGACAGCAGTGTGAAGGTGTGTCAAGGTGTATATTCTCGTGGCTCGGCATTC (SEQ ID NO: 34) |
| 2 | AUH | NM_001698.2 | 591-690 | GGTGGTCTTGAACTGGCTTTAGCCTGTGATATACGAGTAGCAGCTTCCTCTGCAAAAATGGGCCTGGTTGAAACAAAATTGGCGATTATTCCTGGTGGAG (SEQ ID NO: 35) |
| 3 | BANK1 | NM_001083907.1 | 1396-1495 | GGCAAATGAAATGGAAGGGGAAGGAAAACAGAATGGATCAGGCATGGAGACCAAACACAGCCCACTAGAGGTTGGCAGTGAGAGTTCTGAAGACCAGTAT (SEQ ID NO: 36) |
| 4 | BATF3 | NM_018664.2 | 870-969 | CTGCTGTTATGCAGAGCCATTTCCTCTAGAATTTGGATAATAAAGATGCTTATTGTCTCTCCCTTCTCCAGTTCTGGGAATTTACAGGCACAATACACTT (SEQ ID NO: 37) |

TABLE 6-continued

| | Gene | Accession No. | Position | Target Sequence |
|---|---|---|---|---|
| 5 | BTG2 | NM_006763.2 | 1701-1800 | TGCTCTCCTTGGGATGATGGCTGGCT AGTCAGCCTTGCATGTATTCCTTGGC TGAATGGGAGAGTGCCCCATGTTCTG CAAGACTACTTGGTATTCTTGT (SEQ ID NO: 38) |
| 6 | CARD11 | NM_032415.2 | 1076-1175 | TTGAAAATCGGCCCAAGAAGGAGCAG GTTCTGGAACTGGAGCGGGAGAATGA AATGCTGAAGACCAAAAACCAGGAGC TGCAGTCCATCATCCAGGCCGG (SEQ ID NO: 39) |
| 7 | CCDC50 | NM_174908.3 | 975-1074 | AAACACTTTCCAGAGTTCCCTGCAAC CCGTGCTTATGCAGATAGTTACTATTA TGAAGATGGAGGAATGAAGCCAAGAG TGATGAAAGAAGCTGTATCTA (SEQ ID NO: 40) |
| 8 | CCL17 | NM_002987.2 | 230-329 | GCCTGGAGTACTTCAAGGGAGCCATT CCCCTTAGAAAGCTGAAGACGTGGTA CCAGACATCTGAGGACTGCTCCAGGG ATGCCATCGTTTTTGTAACTGT (SEQ ID NO: 41) |
| 9 | CREB3L2 | NM_194071.2 | 2556-2655 | ATGCCTGAGGGGATCAGGCTTTTCTA CTCCAGGCAAACCTGCCCCATCTTGT CGCTTTTAGGACCTCCCACAACCTGG TTCCCCACACATCCATAGTTCT (SEQ ID NO: 42) |
| 10 | CYB5R2 | NM_016229.3 | 367-466 | CCATGTCTTAGGGCTTCCTGTAGGTA ACTATGTCCAGCTCTTGGCAAAAATC GATAATGAATTGGTGGTCAGGGCTTA CACCCCTGTCTCCAGTGATGAT (SEQ ID NO: 43) |
| 11 | DNAJB12 | NM_017626.4 | 1961-2060 | TTTCTTCCATGTTTTAGAAAATGAGGC CTGTTTGGGAAGGTACCCTGGTGAT GTTTTTGCTAGACATTAGCTGTAGCTG ACAGCATAAGGAGAGTCGCA (SEQ ID NO: 44) |
| 12 | FAM159A | NM_001042693.2 | 334-433 | ATTGGCGCTCTCATAGGCCTGTCCGT AGCAGCAGTGGTTCTTCTCGCCTTCA TTGTTACCGCCTGTGTGCTCTGCTAC CTGTTCATCAGCTCTAAGCCCC (SEQ ID NO: 45) |
| 13 | FSCN1 | NM_003088.2 | 1844-1943 | CCCTGCCCTCTTGTCTGCCACGGGGC GAGTCTGGCACCTCTTTCTTCTGACC TCAGACGGCTCTGAGCCTTATTTCTCT GGAAGCGGCTAAGGGACGGTT (SEQ ID NO: 46) |
| 14 | GIT2 | NM_057169.2 | 606-705 | CAGATTTTACAGGCTGAATTATTGGCA GTATATGGAGCAGACCCAGGCACACA GGATTCTAGTGGGAAAACTCCCGTTG ATTATGCAAGGCAAGGAGGGC (SEQ ID NO: 47) |
| 15 | GSK3B | NM_002093.2 | 926-1025 | ACTGATTATACCTCTAGTATAGATGTA TGGTCTGCTGGCTGTGTGTTGGCTGA GCTGTTACTAGGACAACCAATATTTCC AGGGGATAGTGGTGTGGATC (SEQ ID NO: 48) |
| 16 | HOMER2 | NM_004839.2 | 1055-1154 | TGGAAGACAAAGTGCGTTCCTTAAAG ACAGACATTGAGGAGAGCAAATACCG ACAGCGCCACCTGAAGGTGGAGTTGA AGAGCTTCCTGGAGGTGCTGGA (SEQ ID NO: 49) |
| 17 | IF1H1 | NM_022168.2 | 186-285 | GCTTGGGAGAACCCTCTCCCTTCTCT GAGAAAGAAAGATGTCGAATGGGTAT TCCACAGACGAGAATTTCCGCTATCT CATCTCGTGCTTCAGGGCCAGG (SEQ ID NO: 50) |

TABLE 6-continued

| | Gene | Accession No. | Position | Target Sequence |
|---|---|---|---|---|
| 18 | IK | NM_006083.3 | 557-656 | GTCCAAATTCTTGGGTGGTGACATGGAACACACCCATTTGGTGAAAGGCTTGGATTTTGCTCTGCTTCAAAAGGTACGAGCTGAGATTGCCAGCAAAGAG (SEQ ID NO: 51) |
| 19 | IL13RA1 | NM_001560.2 | 1231-1330 | TCTGCACTGGAAGAAGTACGACATCTATGAGAAGCAAACCAAGGAGGAAACCGACTCTGTAGTGCTGATAGAAAACCTGAAGAAAGCCTCTCAGTGATGG (SEQ ID NO: 52) |
| 20 | IRF4 | NM_002460.1 | 326-425 | GGGCACTGTTTAAAGGAAAGTTCCGAGAAGGCATCGACAAGCCGGACCCTCCCACCTGGAAGACGCGCCTGCGGTGCGCTTTGAACAAGAGCAATGACTT (SEQ ID NO: 11) |
| 21 | ISY1 | NM_020701.2 | 87-186 | GGCAAAACATCAGTGTCTGTGGGTAGTTGGAATCTTCAGTTCCTGTGAGCGTCGGCGTCTTCTGGGCCTGTGGAGTTTCTTGGACAGGGGCCGCGGGGCT (SEQ ID NO: 53) |
| 22 | ITPKB | NM_002221.3 | 4201-4300 | GTGGCCTCCTGGCATCATTTGTTATTGCCTCTGAAACAAGCCTTACTGCCTGGAGGGCTTAGATTCCTGCTTCTCCAATGTAGTGTGGGTATCTTGTAGG (SEQ ID NO: 54) |
| 23 | LIMA1 | NM_001113547.1 | 2916-3015 | AACTACATCCTGAACTCGACGTCCTGAGGTATAATACAACAGAGCACTTTTTGAGGCAATTGAAAAACCAACCTACACTCTTCGGTGCTTAGAGAGATCT (SEQ ID NO: 55) |
| 24 | LIMD1 | NM_014240.2 | 2926-3025 | AAGGCAAGTCTCAGGAACCCATGCAGGTACATCGCTTGCACCTGTTTTTAGCTTATTTAATGACGGGCTTTTGGGAAGAGCTGCCCGCATACTGAGAGAC (SEQ ID NO: 56) |
| 25 | MAL | NM_002371.2 | 706-805 | GCCTTCGCGTCCGGGTTGGGAGCTTGCTGTGTCTAACCTCCAACTGCTGTGCTGTCTGCTAGGGTCACCTCCTGTTTGTGAAAGGGGACCTTCTTGTTCG (SEQ ID NO: 57) |
| 26 | MAML3 | NM_0187174 | 1351-1450 | TGGAAGCCATCAACAATTTGCCCAGTAACATGCCACTGCCTTCAGCTTCTCCTCTTCACCAACTTGACCTGAAACCTTCTTTGCCCTTGCAGAACAGTGG (SEQ ID NO: 58) |
| 27 | MME | NM_000902.2 | 5060-5159 | GGATTGTAGGTGCAAGCTGTCCAGAGAAAAGAGTCCTTGTTCCAGCCCTATTCTGCCACTCCTGACAGGGTGACCTTGGGTATTTGCAATATTCCTTTGG (SEQ ID NO: 59) |
| 28 | MOBKL2C | NM_145279.4 | 1631-1730 | TTCTCTTACCCAGAGATGCCCATGAGCTGACATTTTACTCATCCCTCTGCCTCCAAGAAGGCCTGTATTATACGTGTCCTCCTGGGGGTTGGAGATGATC (SEQ ID NO: 60) |
| 29 | MST1R | NM_002447.1 | 3301-3400 | CCACTTTGGAGTTGTCTACCACGGAGAATACATAGACCAGGCCCAGAATCGAATCCAATGTGCCATCAAGTCACTAAGTCGCATCACAGAGATGCAGCAG (SEQ ID NO: 61) |
| 30 | MYBL1 | XM_034274.14 | 1441-1540 | GGCAAACGCTGTGTTATCCTCTTTGCAGACCATCCCAGAATTTGCAGAGACTCTAGAACTTATTGAATCTGATCCTGTAGCATGGAGTGACGTTACCAGT (SEQ ID NO: 62) |

TABLE 6-continued

| | Gene | Accession No. | Position | Target Sequence |
|---|---|---|---|---|
| 31 | NECAP2 | NM_018090.4 | 991-1090 | CTCTCCTCTCCTCCTTGTCTGGCTCT GTTGACAAACCGGGCATGTTTGGCAG TAAATTGGCACCGTGTCACACTGTTTC CTGGGATTCAAGTATGCAACC (SEQ ID NO: 63) |
| 32 | NFIL3 | NM_005384.2 | 186-285 | CCTTTCTTTCTCCTCGCCGGCCCGAG AGCAGGAACACGATAACGAAGGAGG CCCAACTTCATTCAATAAGGAGCCTG ACGGATTTATCCCAGACGGTAGA (SEQ ID NO: 64) |
| 33 | OPA1 | NM_130837.1 | 1356-1455 | CTGAGACCATATCCTTAAATGTAAAAG GCCCTGGACTACAGAGGATGGTGCTT GTTGACTTACCAGGTGTGATTAATACT GTGACATCAGGCATGGCTCC (SEQ ID NO: 65) |
| 34 | PDCD1LG2 | NM_025239.3 | 643-742 | AGGAAAATAAACACTCACATCCTAAAG GTTCCAGAAACAGATGAGGTAGAGCT CACCTGCCAGGCTACAGGTTATCCTC TGGCAGAAGTATCCTGGCCAA (SEQ ID NO: 66) |
| 35 | PHF23 | NM_024297.2 | 1661-1760 | CTGTCTGTGTCCCGACACATAATCTCT GTCTCTTGGACCTGCCACCATCACTT TCTGGGTCAGGATTGGAATTGGGATG GAATGGGACAGTTGTCTATAA (SEQ ID NO: 67) |
| 36 | PIM2 | NM_006875.2 | 621-720 | GCCATCCAGCACTGCCATTCCCGTGG AGTTGTCCATCGTGACATCAAGGATG AGAACATCCTGATAGACCTACGCCGT GGCTGTGCCAAACTCATTGATT (SEQ ID NO: 68) |
| 37 | PRDX2 | NM_005809.4 | 651-750 | GCATGGGGAAGTTTGTCCCGCTGGCT GGAAGCCTGGCAGTGACACGATTAAG CCCAACGTGGATGACAGCAAGGAATA TTTCTCCAAACACAATTAGGCT (SEQ ID NO: 69) |
| 38 | PRKCB | NM_212535.1 | 1751-1850 | GCATTTGGAGTCCTGCTGTATGAAAT GTTGGCTGGGCAGGCACCCTTTGAAG GGGAGGATGAAGATGAACTCTTCCAA TCCATCATGGAACACAACGTAG (SEQ ID NO: 70) |
| 39 | PRR6 | NM_181716.2 | 606-705 | TTCATTGTTCCAGCTTCTCGCTTCAAG CTCCTGAAGGGAGCTGAGCACATAAC GACTTACACGTTCAATACTCACAAAGC CCAGCATACCTTCTGTAAGA (SEQ ID NO: 71) |
| 40 | PTGIR | NM_000960.3 | 1271-1370 | CTGACATTTCAAGCTGACCCTGTGAT CTCTGCCCTGTCTTCGGGCGACAGGA GCCAGAAAATCAGGGACATGGCTGAT GGCTGCGGATGCTGGAACCTTG (SEQ ID NO: 72) |
| 41 | QSOX1 | NM_002826.4 | 2566-2665 | TAGGGCAGCTCAGTCCCTGGCCTCTT AGCACCACATTCCTGTTTTTCAGCTTA TTTGAAGTCCTGCCTCATTCTCACTGG AGCCTCAGTCTCCTGCTT (SEQ ID NO: 73) |
| 42 | R3HDM1 | NM_015361.2 | 1276-1375 | CCTGTGTTCCCAAGAGAATTACATTAT TGACAAAAGACTCCAAGACGAGGATG CCAGTAGTACCCAGCAGAGGCGCCA GATATTTAGAGTTAATAAAGAT (SEQ ID NO: 74) |
| 43 | RAB7L1 | NM_001135664.1 | 786-885 | CATTTGAATTGTCTCCTGACTACTGTC CAGTAAGGAGGCCCATTGTCACTTAG AAAAGACACCTGGAACCCATGTGCAT TTCTGCATCTCCTGGATTAGC (SEQ ID NO: 75) |

TABLE 6-continued

| | Gene | Accession No. | Position | Target Sequence |
|---|---|---|---|---|
| 44 | RCL1 | NM_005772.3 | 696-795 | TGGTGAATCATTTGAACTGAAGATTGT GCGACGGGGAATGCCTCCCGGAGGA GGAGGCGAAGTGGTTTTCTCATGTCC TGTGAGGAAGGTCTTGAAGCCC (SEQ ID NO: 76) |
| 45 | RHOF | NM_019034.2 | 142-241 | CTGCGGCAAGACCTCGCTGCTCATGG TGTACAGCCAGGGCTCCTTCCCCGAG CACTACGCCCCATCGGTGTTCGAGAA GTACACGGCCAGCGTGACCGTT (SEQ ID NO: 77) |
| 46 | S1PR2 | NM_004230.2 | 186-285 | TCCCGCCAGGTGGCCTCGGCCTTCAT CGTCATCCTCTGTTGCGCCATTGTGG TGGAAAACCTTCTGGTGCTCATTGCG GTGGCCCGAAACAGCAAGTTCC (SEQ ID NO: 78) |
| 47 | SERPINA9 | NM_001042518.1 | 1156-1255 | CCACTAAATCCTAGGTGGGAAATGGC CTGTTAACTGATGGCACATTGCTAATG CACAAGAAATAACAAACCACATCCCT CTTTCTGTTCTGAGGGTGCAT (SEQ ID NO: 79) |
| 48 | SLAMF1 | NM_003037.2 | 581-680 | GTGTCTCTTGATCCATCCGAAGCAGG CCCTCCACGTTATCTAGGAGATCGCT ACAAGTTTTATCTGGAGAATCTCACCC TGGGGATACGGGAAAGCAGGA (SEQ ID NO: 80) |
| 49 | SNX11 | NM_013323.2 | 1361-1460 | TCATTTGTATGTAGGACCAGGAGTAT CTCCTCAGGTGACCAGTTTTGGGGAC CCGTATGTGGCAAATTCTAAGCTGCC ATATTGAACATCATCCCACTGG (SEQ ID NO: 81) |
| 50 | TFPI2 | NM_006528.2 | 601-700 | TTTAATCCAAGATACAGAACCTGTGAT GCTTTCACCTATACTGGCTGTGGAGG GAATGACAATAACTTTGTTAGCAGGG AGGATTGCAAACGTGCATGTG (SEQ ID NO: 82) |
| 51 | TMOD1 | NM_003275.2 | 771-870 | AGATGCTCAAGGAGAACAAGGTGTTG AAGACACTGAATGTGGAATCCAACTT CATTTCTGGAGCTGGGATTCTGCGCC TGGTAGAAGCCCTCCCATACAA (SEQ ID NO: 83) |
| 52 | TNFRSF13B | NM_012452.2 | 161-260 | TGCAAAACCATTTGCAACCATCAGAG CCAGCGCACCTGTGCAGCCTTCTGCA GGTCACTCAGCTGCCGCAAGGAGCA AGGCAAGTTCTATGACCATCTCC (SEQ ID NO: 84) |
| 53 | TRAF1 | NM_005658.3 | 3736-3835 | CGAGTGATGGGTCTAGGCCCTGAAAC TGATGTCCTAGCAATAACCTCTTGATC CCTACTCACCGAGTGTTGAGCCCAAG GGGGGATTTGTAGAACAAGCC (SEQ ID NO: 85) |
| 54 | TRIM56 | NM_030961.1 | 2571-2670 | GTGGAGGCCGAGGACATTTTCCTGAA GGGCAGGGGTTGGCAACTTTTCAACA TGGAGTGCCAAACTGCTAACCCGTCT TCTAGTGTGTGAGAATAGGGAC (SEQ ID NO: 86) |
| 55 | UBXN4 | NM_014607.3 | 344-443 | CATCGCGACGGCCAAAAGGAGCGGC GCGGTCTTCGTGGTGTTCGTGGCAG GTGATGATGAACAGTCTACACAGATG GCTGCAAGTTGGGAAGATGATAAA (SEQ ID NO: 87) |
| 56 | VRK3 | NM_016440.3 | 821-920 | ACAGACAAGAGTGGGCGACAGTGGA AGCTGAAGTCCTTCCAGACCAGGGAC AACCAGGGCATTCTCTATGAAGCTGC ACCCACCTCCACCCTCACCTGTG (SEQ ID NO: 88) |

TABLE 6-continued

| | Gene | Accession No. | Position | Target Sequence |
|---|---|---|---|---|
| 57 | WAC | NM_100486.2 | 756-855 | CCTCTGGACTGAACCCCACATCTGCA CCTCCAACATCTGCTTCAGCGGTCCC TGTTTCTCCTGTTCCACAGTCGCCAAT ACCTCCCTTACTTCAGGACCC (SEQ ID NO: 89) |
| 58 | WDR55 | NM_017706.4 | 816-915 | CTACCTCTTCAATTGGAATGGCTTTGG GGCCACAAGTGACCGCTTTGCCCTGA GAGCTGAATCTATCGACTGCATGGTT CCAGTCACCGAGAGTCTGCTG (SEQ ID NO: 90) |

The DLBCL90 was applied to 171 GCB-DLBCL including 156/157 of the samples whose RNAseq were used define the DHITsig. All 171 GCB-DLBCL were selected from the 347 patient BC Cancer cohort and had RNAseq data available, such that the RNAseq DHITsig score could be calculated and DHITsig categories assigned. Importantly, the 15 additional samples that were not part of the "discovery cohort" had been excluded from that cohort on the basis that they did not have both MYC and BCL2 FISH results available. The QC threshold of the geometric mean of the 13 housekeeping genes being greater than 60 was carried over from the Lymph3Cx.

To prevent over-fitting, the gene coefficients from the RNAseq model, which were the Importance Score for that gene, were carried over to the DLBCL90 model unaltered. The DLBCL90 DHITsig score was calculated as the sum of the gene coefficient (Importance Score) multiplied by the $\log_2$ transformed normalized gene expression. In order to determine the appropriate thresholds for the DLBCL90 score, 72 of the 171 samples were selected on the basis of being equally distributed across the scores for the population (FIG. 2B). To avoid circularity, this cohort included the 35 samples used for gene selection to leave a cohort of samples that had not contributed to gene selection and threshold training. The thresholds were selected according to Bayes rule with 20% and 80% used as the threshold probabilities. This level was used, as opposed to 90%, as it resulted in 10% of the population in an "indeterminate" group where assignment could not be made with sufficient confidence. With these thresholds, 3 (4%) tumors were misclassified with 2 RNAseq DHITsig-neg being called DHITsig-pos by the DLBCL90 (including 1 case that was HGBL-DH/TH-BCL2) and 1 RNAseq DHITsig-pos being called DHITsig-neg by the DLBCL90. Seven (10%) were deemed DHITsig-ind.

Figure 3:
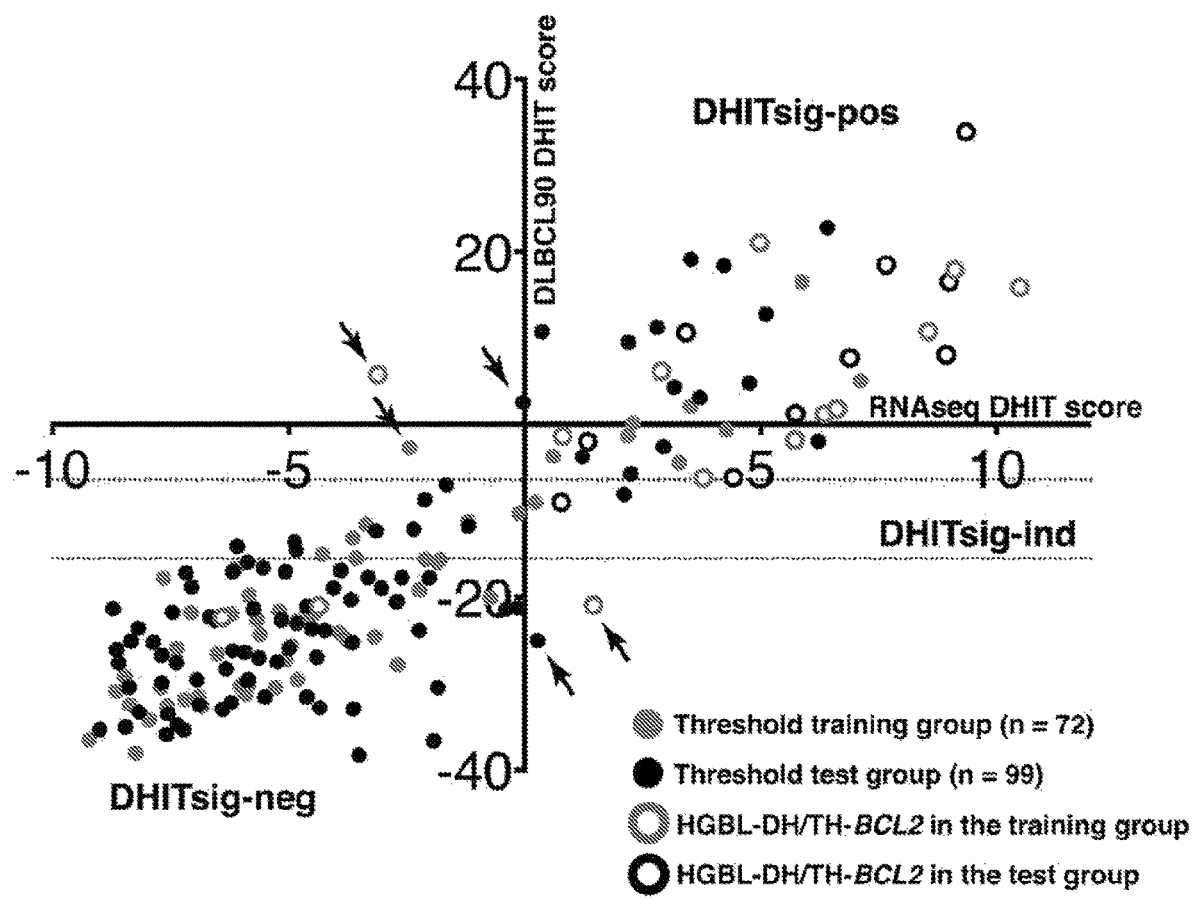
FIG. 3 shows the DHITsig score from the RNAseq model (X-axis) against the DHITscore from the DLBCL90 assay in 171 GCB-DLBCL. The 72 biopsies were used to establish the thresholds for the assay. Arrows highlight the 5 (3%) tumors that were frankly misclassified.

These thresholds were locked and the model was then applied to the remaining 99 samples (blinded to outcome and the DHITsig result from RNAseq) to test the final model, including the thresholds. Nine cases (9%) were assigned to DHITsig-ind. Two cases (2%) were misclassified with one being DHITsig-pos by RNAseq but DHITsig-neg by DLBCL90 and one vice versa. Taken as a total group, the misclassification rate was 3% (5/171) (FIG. 3).

Applying the DLBCL90 to a Population Registry-Based Cohort

On review of the 347-patient cohort, one tumor from the training cohort (DLC0224) was removed due to a tumor content of <10%. As the thresholds had been "locked" prior to the removal of this sample, the thresholding was not repeated on the data set after removal of the sample. The DLBCL90 was applied to an additional 152 biopsies to complete a total of 322 eligible cases from the 347 patient BC Cancer cohort—RNA was not available for the remaining 24 patients. Note that inclusion of DLC0224 would have strengthened the outcome correlation of the DHITsig-pos group, as the patient was DHITsig-pos and had a poor outcome (death at 0.6 years).

Performance of the Lymph2Cx Component

Figure 4:
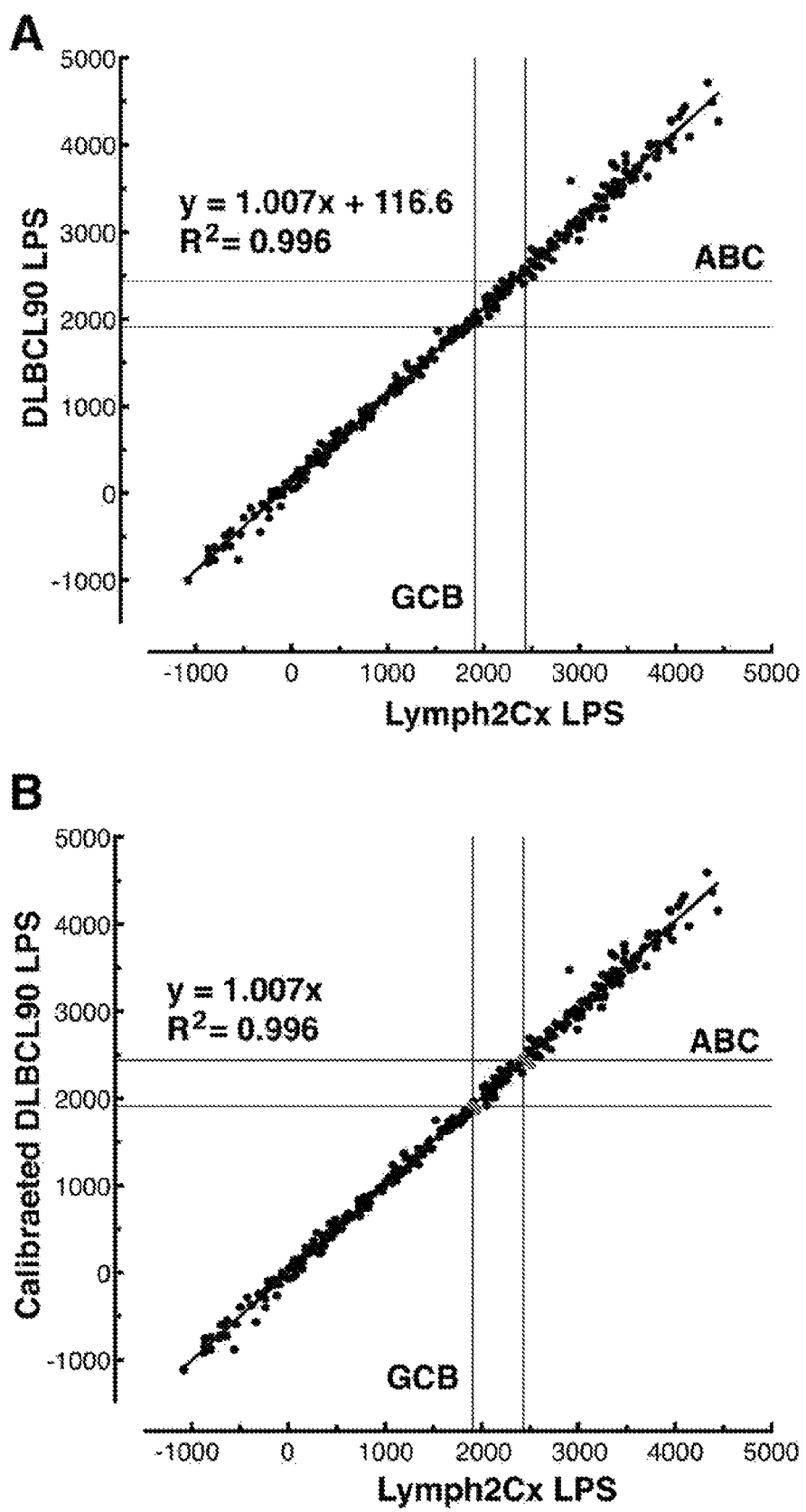
FIG. 4A shows comparisons between the linear predictor score (LPS) from the Lymph2Cx (Scott, Mottok et al J Clin Oncol 2015) and the DLBCL90 assay. The figure shows the uncalibrated DLBCL90 LPS scores. Six (6) tumors (2%) were moved from a definitive category to Unclassified (or vice versa).
FIG. 4B shows comparisons between the linear predictor score (LPS) from the Lymph2Cx (Scott, Mottok et al J Clin Oncol 2015) and the DLBCL90 assay. The figures shows the calibrated DLBCL90 LPS scores, where 116.6 points were removed from the uncalibrated scores. Six (6) tumors (2%) were moved from a definitive category to Unclassified (or vice versa).

Linear predictor scores (LPS) were available for 320 samples from both the Lymph2Cx assay[2] and the DLBCL90. The correlation between the scores was very high ($R^2$=0.996) and the slope was 1.007. The bias (the Y-intercept was +116.6 points (FIG. 4A). Therefore, to calibrate the DLBCL90 LPS to the original Lymph2Cx score, 116.6 points were removed from the DLBCL90 LPS (FIG. 4B). In total, six tumors (2%) changed COO, going from definitive COO categories to Unclassified or vice versa—there were no cases that changed from ABC to GCB or vice versa. Thus, the addition of the DHITsig 30 gene module did not impact the performance of the Lymph2Cx component of the assay.

The DHITsig Across the Population Registry-Based Cohort

The results in the GCB-DLBCL and Unclassified-DLBCL (with COO determined using the DLBCL90 LPS) are shown in FIG. 4A. Results in the ABC-DLBCL are not shown. In GCB-DLBCL, 23% were classified as DHITsig-pos, 10% were DHITsig-ind and 66% DHITsig-neg, while in Unclassified-DLBCL, these figures were 6% DHITsig-pos and 94% DHITsig-neg and in ABC-DLBCL 4% were DHITsig-ind and 96% DHITsig-neg. Over the entire cohort, 45/322 (14%) were DHITsig-pos, 23/322 (7%) were DHITsig-ind and 254/322 (79%) were DHITsig-neg.

Figure 14:
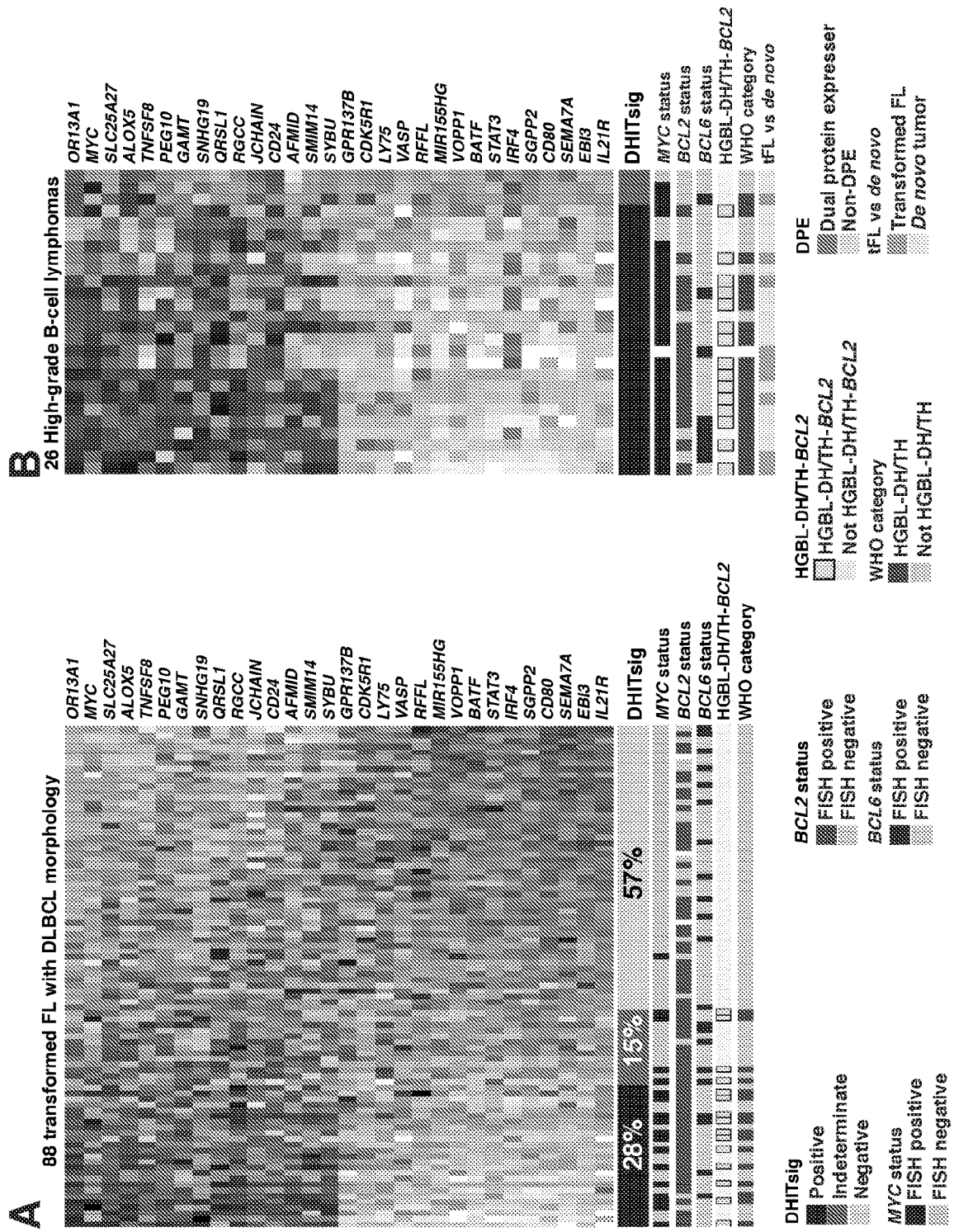
FIG. 14A shows the gene expression-based model for the DHIT signature in which the DLBCL90 assay is shown in the form of a heatmap, with the 88 transformed follicular lymphoma (tFL) with DLBCL morphology. The tumors are arrayed from highest DHIT sig score on the left to lowest DHITsig score on the right. DHITsig groups identified by the signature are shown below the heat map.
FIG. 14B shows the gene expression-based model for the DHIT signature in which the DLBCL90 assay is shown in the form of a heatmap, with the 26 high-grade B-cell lymphomas. The tumors are arrayed from highest DHIT sig score on the left to lowest DHITsig score on the right. DHITsig groups identified by the signature are shown below the heat map. The status of MYC, BCL2 and BCL6 genetic alterations, HGBL-DH/TH-BCL2 status and WHO categories are also shown.

Applying the DLBCL90 to Transformed Follicular Lymphoma and High-Grade B-Cell Lymphomas Transformed Follicular Lymphoma with DLBCL Morphology The DLBCL90 was applied to the 88 tFL with DLBCL morphology, previously described in Kridel et al[20] to validate the association between the DHITsig assignment by the DLBCL90 and HGBL-DH/TH-BCL2. The results are shown in FIG. 14A, with all HGBL-DH/TH-BCL2 falling with the DHITsig-pos and DHITsig-ind groups.

High-Grade B-Cell Lymphoma

The DLBCL90 was applied to 26 high-grade B-cell lymphomas drawn from the BC Cancer Centre for Lymphoid Cancer Database. These tumors would be categorized as high-grade B-cell lymphoma (n=4) or HGBL-DH/TH with high-grade morphology (n=18) with 4 lymphomas having insufficient FISH results to place them in the correct category. The morphology of the tFL cases within this cohort had already been centrally reviewed. The morphology of the remaining 17 cases were reviewed by a panel of expert hematopathologists (PF, GWS, JC and TT) and confirmed to be high-grade as opposed to DLBCL. The results are shown in FIG. 14B, with 23/26 (88%) being DHITsig-pos and the remaining tumors being DHITsig-ind.

Following the REMARK guidelines, the assay parameters were locked prior to application to the "validation" cohorts. On review of the assembled data, it would appear that the DHITsig-pos and DHITsig-ind share similar quite outcomes and if considered together they would have detected all HGBL-DH/TH-BCL2 cases within the tFL with DLBCL morphology. For this reason, depending on the application, DHITsig-ind may be considered a positive result, which would maximize specificity thereby enriching for patients with very good outcomes (i.e. DHITsig-neg).

Results

Development of the DHIT Gene Expression Signature

Figure 5A:
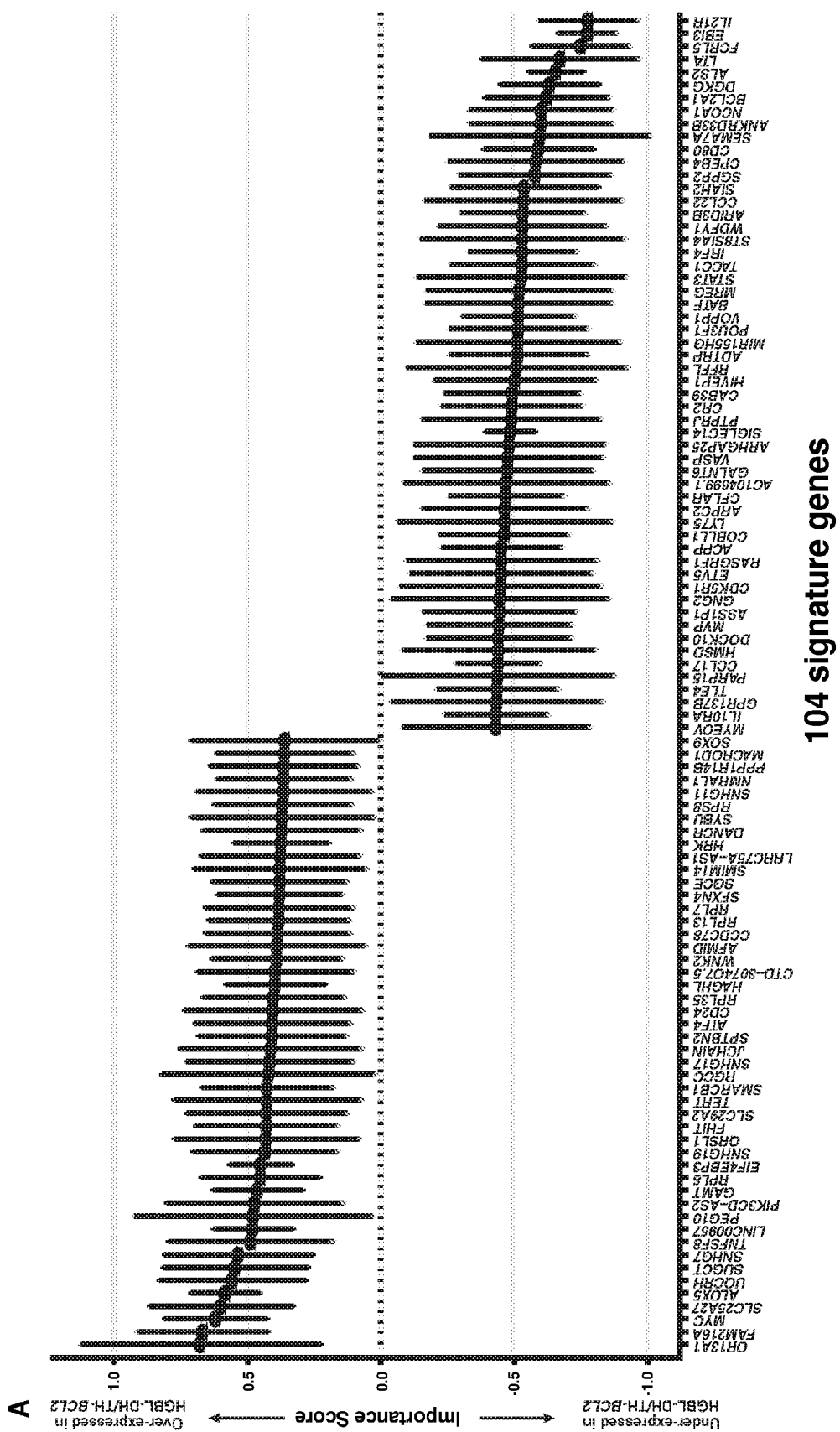
FIG. 5A shows the gene expression-based model of 104 genes based on HGBL-DH/TH-BCL2 status showing the importance score with 95% confidence interval of the 104 most significantly differentially expressed genes between HGBL-DH/TH-BCL2 and GCB-DLBCL. Genes with dark grey and light grey bars are over- and under-expressed in HGBL-DH/TH-BCL2, respectively.
Figure 5B:
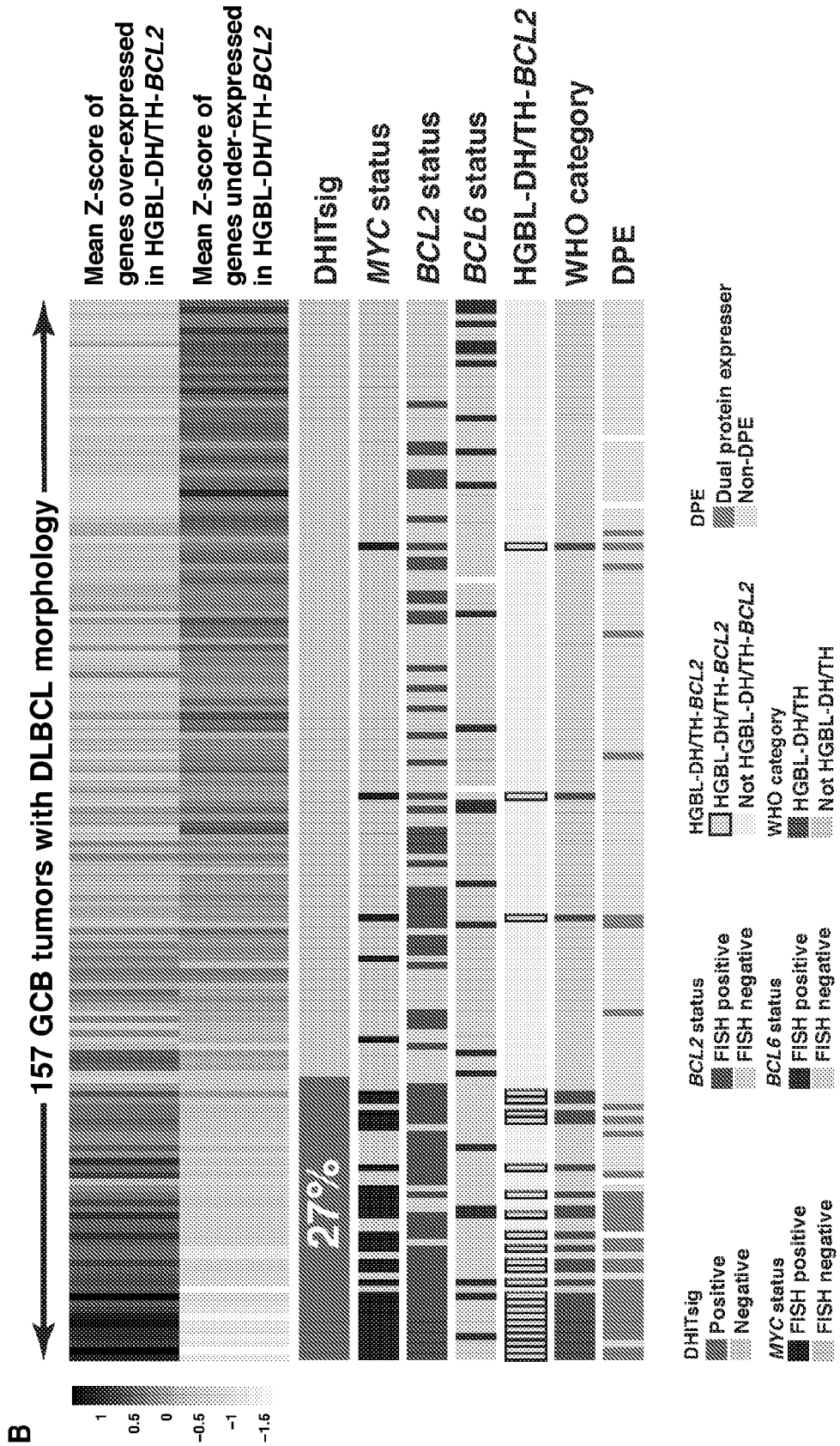
FIG. 5B shows the mean Z-score of genes over- or under-expressed in HGBL-DH/TH-BCL2 is shown in the form of a heatmap, with the 157 patient biopsies shown as columns. DHITsig groups identified by the signature are shown below the heat map. The status of MYC, BCL2 and BCL6 genetic alterations, HGBL-DH/TH-BCL2, WHO categories and MYC/BCL2 dual protein expresser (DPE) status are displayed beneath the heatmap.

We identified 104 genes that were most significantly differentially expressed between HGBL-DH/TH-BCL2 and other GCB-DLBCLs (FIG. 5A). We devised a model score using the expression of these 104 genes that separates GCB-DLBCL into two groups. The smaller group, comprising 42 tumors (27%), was termed "double-hit signature"-positive (DHITsig-pos) and included 22 of the 25 HGBL-DH/TH-BCL2 tumors, as determined by FISH. The remaining 115 GCB cases (73%) were considered DHITsig-negative (DHITsig-neg), including 3 HGBL-DH/TH-BCL2 tumors (FIG. 5B).

Prognostic Value of the DHIT Signature

Having developed the DHITsig blinded to patient outcomes, we then explored the prognostic impact of the DHITsig within the 157 uniformly R-CHOP treated cohort of de novo GCB-DLBCL[6, 24] using assignments from the locked RNAseq model. DHITsig was not associated with clinical variables, including the factors of International Prognostic Index (IPI), IPI subgroups, B-symptoms or tumor volume. As expected, MYC and BCL2 translocations and protein expression of MYC and BCL2 were significantly more frequent in DHITsig-pos cases (all, P<0.001; Table 10).

TABLE 10

Difference of patient characteristics according to DHIT signature in GCB-DLBCL

| | | DHIT Signature-pos (n = 42) n (%) | DHIT signature-neg (n = 118) n (%) | p |
|---|---|---|---|---|
| Age | Median (range) | 62 (35-79) | 52 (19-92) | .97 |
| | ≤60 years | 18 (43) | 47 (41) | |
| | >60 years | 24 (57) | 68 (59) | |
| Gender | Female | 14 (33) | 48 (42) | .44 |
| | Male | 28 (67) | 67 (58) | |
| Stage | I, II | 18 (44) | 66 (58) | .17 |
| | III, IV | 23 (56) | 48 (42) | |
| | N/A | 1 | 1 | |
| LDH | Normal | 16 (42) | 60 (58) | |
| | >ULN | 22 (58) | 44 (42) | .14 |
| | N/A | 4 | 11 | |
| ECOG PS | 0-1 | 28 (68) | 89 (78) | |
| | 2 or more | 13 (32) | 25 (22) | .30 |
| | N/A | 1 | 1 | |
| Extranodal sites | 0-1 | 38 (93) | 100 (88) | |
| | 2 or more | 3 (7) | 14 (12) | .56 |
| | N/A | 1 | 1 | |
| B-symptom | No | 26 (63) | 74 (65) | |
| | Yes | 15 (37) | 40 (35) | 1.0 |
| | N/A | 1 | 1 | |

TABLE 10-continued

Difference of patient characteristics according to DHIT signature in GCB-DLBCL

| | | DHIT Signature-pos (n = 42) n (%) | DHIT signature-neg (n = 118) n (%) | p |
|---|---|---|---|---|
| Tumor mass >10 cm | No | 27 (71) | 87 (78) | .48 |
| | Yes | 11 (29) | 24 (22) | |
| | N/A | 4 | 4 | |
| IPI score | Low (0-1) | 14 (35) | 47 (42) | |
| | Intermediate (2-3) | 19 (48) | 51 (46) | .56 |
| | High (4-5) | 7 (17) | 13 (12) | |
| Ki-67 IHC | N/A | 2 | 4 | .48 |
| | <80% | 26 (65) | 77 (73) | |
| | ≥80% | 14 (35) | 29 (27) | |
| | N/A | 2 | 9 | |
| MYC-TR | No | 15 (36) | 111 (97) | |
| | Yes | 27 (64) | 4 (3) | <.001 |
| | N/A | 0 | 0 | |
| BCL2-TR | No | 6 (15) | 75 (65) | <.001 |
| | Yes | 36 (85) | 40 (35) | |
| | N/A | 0 | 0 | |
| MCY/BCL2-TR (HGBL-DH/TH-BCL2) | No | 20 (48) | 112 (98) | |
| | Yes | 22 (52) | 3 (2) | <.001 |
| | N/A | 0 | 0 | |
| MYC-IHC | Negative | 10 (25) | 91 (80) | |
| | Positive | 30 (75) | 23 (20) | <.001 |
| | N/A | 2 | 1 | <.001 |
| BCL2-IHC | Negative | 5 (12) | 58 (51) | |
| | Positive | 36 (88) | 55 (49) | |
| | N/A | 1 | 2 | |
| MYC/BCL2-IHC (DPE) | No | 15 (37) | 106 (93) | <.001 |
| | Yes | 25 (63) | 8 (7) | |
| | N/A | 2 | 1 | |

Figure 7C:
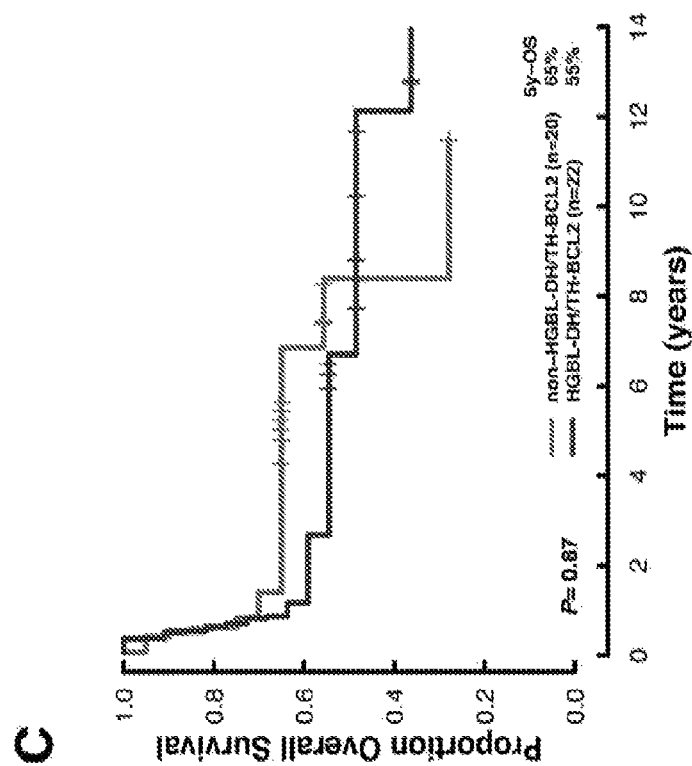
FIG. 7C shows Kaplan Meier curves of the cases with HGBL-DH/TH-BCL2 (black) vs non-HGBL-DH/TH-BCL2 (grey) within DHITsig-pos GCB-DLBCL for OS.

Bold indicates significance.
Abbreviations:
DHITsig, double-hit signature;
DPE, double protein expression;
ECOG PS, Eastern Cooperative Oncology Group performance status;
IHC, immunohistochemistry;

DHITsig-pos cases had significantly shorter TTP, DSS and OS when compared with the DHITsig-neg GCB group (log-lank P<0.001, P<0.001 and P=0.012, respectively) exhibiting outcomes comparable to those of ABC-DLBCL from the cohort of 347 patients (FIG. 6A-C). Importantly, the non-HGBL-DH/TH-BCL2 cases with the DHITsig-pos group showed comparably poor prognosis to HGBL-DH/TH-BCL2 cases (FIGS. 7A-C). Although IPI and dual protein expression of MYC and BCL2 (DPE) were also associated with survival in GCB-DLBCL (Table 7), DHITsig remained prognostic of TTP and DSS in multivariate analysis (HR=3.1 [95% CI 1.5-6.4]; P=0.002, HR=3.1 [95% CI 1.3-7.1]; P=0.008, respectively) independent of these factors (Table 8).

TABLE 7

Univariate analysis of DHIT signature, IPI and DPE

| | Time to Progression | |
|---|---|---|
| Variables | HR (95% CI) | p-value |
| DHIT signature (pos vs neg) | 2.83 (1.57-5.10) | <.001 |
| HGBL-DH/TH-BCL2 (pos vs neg) | 2.22 (1.14-4.30) | .02 |
| DPE (pos. vs neg.) | 1.52 (0.78-2.95) | .22 |
| IPI (high: 3-5 vs low: 0-2) | 3.57 (1.94-6.56) | <.001 |

TABLE 7-continued

Univariate analysis of DHIT signature, IPI and DPE

| | Disease specific survival | | |
|---|---|---|---|
| Variables | HR (95% CI) | p-value | |
| DHIT signature (pos vs neg) | 3.47 (1.77-6.82) | <.001 | |
| HGBL-DH/TH-BCL2 (pos vs neg) | 2.47 (1.18-5.18) | .02 | |
| DPE (pos. vs neg.) | 2.09 (1.01-4.31) | .05 | |
| IPI (high: 3-5 vs low: 0-2) | 5.03 (2.48-10.18) | <.001 | |

| | Overall Survival | | |
|---|---|---|---|
| Variables | HR (95% CI) | p-value | |
| DHIT signature (pos vs neg) | 1.96 (1.16-3.32) | .01 | |
| HGBL-DH/TH-BCL2 (pos vs neg) | 1.66 (.92-3.01) | .09 | |
| DPE (pos. vs neg.) | 1.68 (.97-2.91) | .06 | |
| IPI (high: 3-5 vs low: 0-2) | 3.21 (1.90-5.42) | <.001 | |

TABLE 8

Multivariate analysis including DHIT signature, HGBL-DH/TH-BCL2, DPE and IPI

| | | Time to Progression | |
|---|---|---|---|
| Model | Variables | HR (95% CI) | p-value |
| Model1- all variables | DHIT signature (pos vs neg) | 3.49 (1.49-8.16) | .004 |
| | HGBL-DH/TH-BC12 (pos vs neg) | 0.83 (0.33-2.09) | .69 |
| | DPE (pos. vs neg.) | 0.91 (0.40-2.08) | .83 |
| | IPI (high: 3-5 vs low: 0-2) | 3.22 (1.71-6.08) | <.001 |
| Model2- results of feature selection | DHITsig (pos vs neg) | 3.04 (1.62-5.68) | <.001 |
| | IPI (high: 3-5 vs low: 0-2) | 3.27 (1.74-6.15) | <.001 |

| | | Disease specific survival | |
|---|---|---|---|
| Model | Variables | HR (95% CI) | p-value |
| Model1- all variables | DHIT signature (pos vs neg) | 2.97 (1.11-7.94) | .03 |
| | HGBL-DH/TH-BCL2 (pos vs neg) | 1.03 (0.37-2.84) | .96 |
| | DPE (pos. vs neg.) | 1.26 (0.51-3.07) | .62 |
| | IPI (high: 3-5 vs low: 0-2) | 4.39 (2.12-9.10) | <.001 |
| Model2- results of feature selection | DHITsig (pos vs neg) | 3.36 (1.65-6.83) | <.001 |
| | IPI (high: 3-5 vs low: 0-2) | 4.29 (2.09-8.79) | <.001 |

| | | Overall Survival | |
|---|---|---|---|
| Model | Variables | HR (95% CI) | p-value |
| Model1- all variables | DHIT signature (pos vs neg) | 1.76 (0.78-3.98) | .18 |
| | HGBL-DH/TH-BCL2 (pos vs neg) | 0.93 (0.38-2.29) | .88 |
| | DPE (pos. vs neg.) | 1.39 (0.69-2.83) | .36 |
| | IPI (high: 3-5 vs low: 0-2) | 2.97 (1.72-5.13) | <.001 |
| Model2- results of feature selection | DHITsig (pos vs neg) | 1.97 (1.12-3.49) | .02 |
| | IPI (high: 3-5 vs low: 0-2) | 2.88 (1.68-4.93) | <.001 |

Figure 8C:
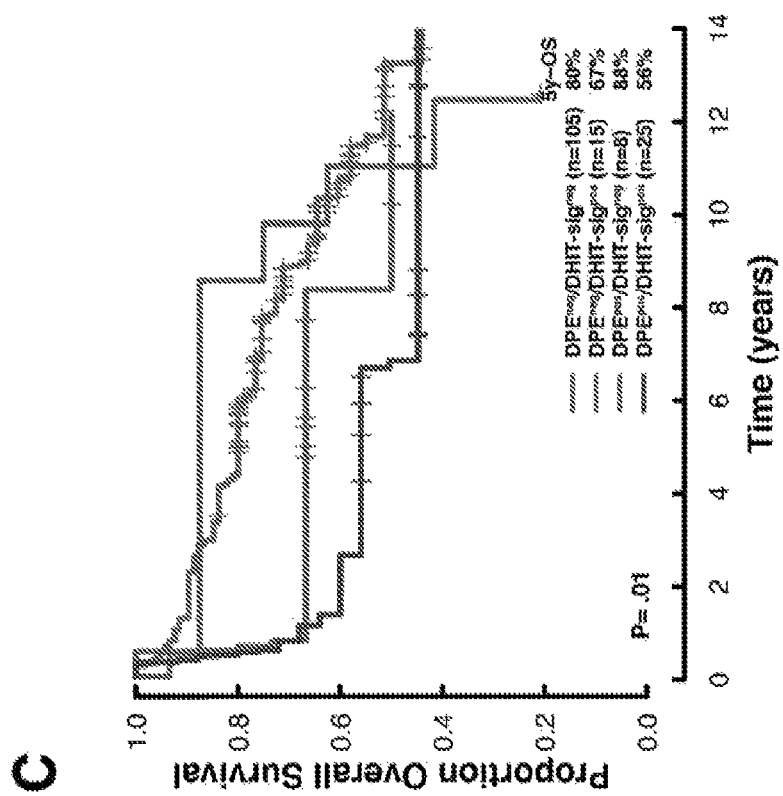
FIG. 8C shows Kaplan Meier curves of cases stratified by DHIT signature combined with DPE status in GCB-DLBCL for OS.

In particular, DPE did not provide statistically significant risk stratification within either the DHITsig-pos or -neg groups (FIGS. 8A-C), indicating that the DHITsig designation subsumes the prognostic impact of DPE within GCB-DLBCL. We then applied this gene expression model to GCB-DLBCL from an independent dataset (Reddy et al; n=262 GCB-DLBCLs), in which the DHIT sig-pos group also had significantly inferior OS compared with other GCB-DLBCLs (p<0.001) (FIG. 6D).

Double Hit Signature Defines a Biologically Distinct Subgroup within GCB-DLBCL

Figure 9:
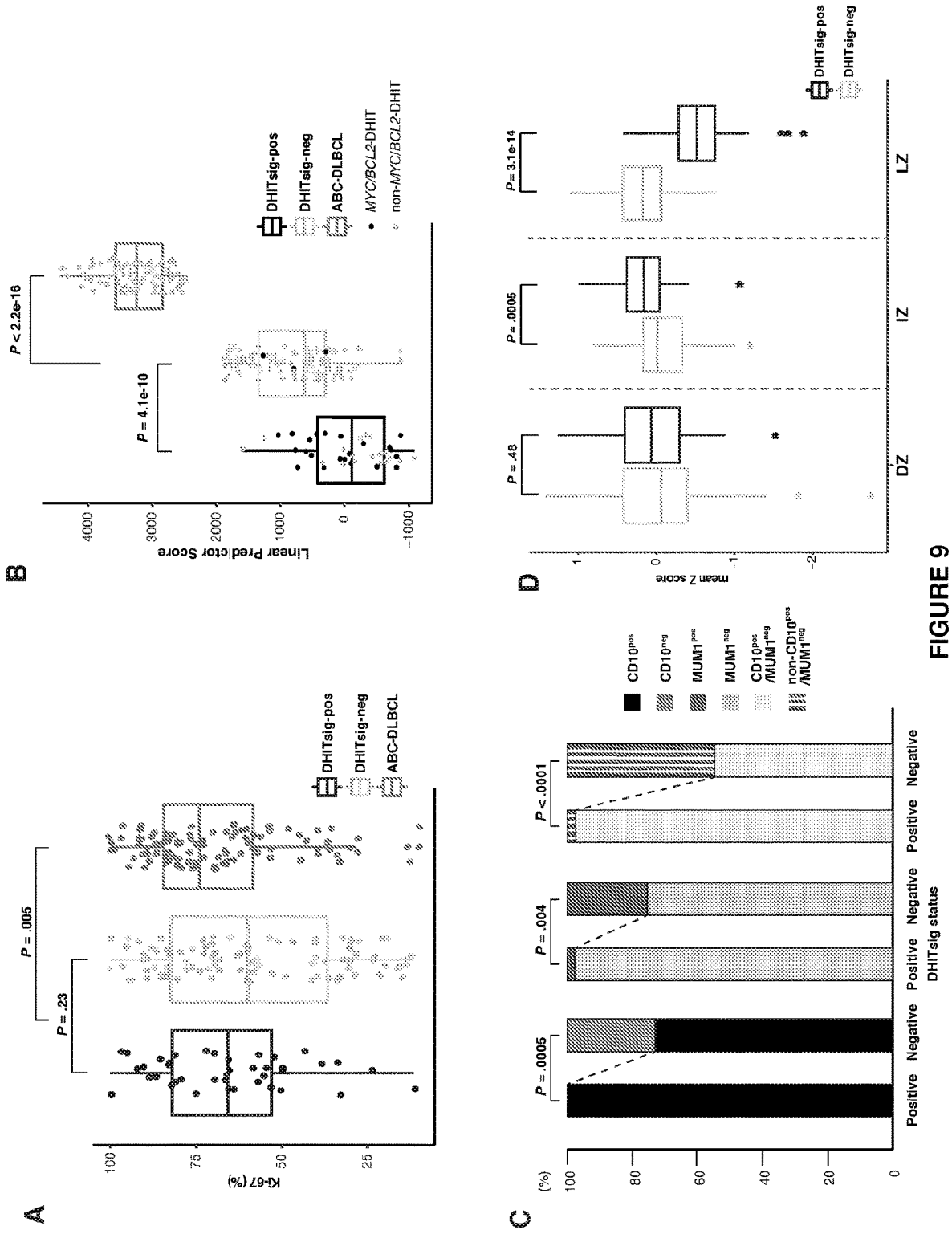
FIG. 9A shows the genetic, molecular and phenotypic features of DHIT signature comparing Ki67 staining by IHC between DHITsig-pos, DHITsig-neg GCB-DLBCL and ABC-DLBCL.
FIG. 9B shows the genetic, molecular and phenotypic features of DHIT signature comparing linear predictor score (LPS), provided by Lymph2Cx assay, between DHITsig-pos, DHITsig-neg GCB-DLBCL and ABC-DLBCL. Black dots represent the HGBL-DH/TH-BCL2 tumors.
FIG. 9C shows the genetic, molecular and phenotypic features of DHIT signature comparing IHC staining pattern of CD10 (MME) and MUM1 (IRF4) between DHITsig-pos and DHITsig-neg GCB-DLBCL cases.
FIG. 9D shows the genetic, molecular and phenotypic features of DHIT signature comparing mean Z scores of DZ, IZ and LZ signature gens (20 genes each) between DHITsig-pos and -neg groups. DZ; dark-zone, IZ; intermediate-zone, LZ; light-zone.

Exploration of the pathology and gene expression patterns demonstrated that DHITsig-pos tumors form a distinct biological subgroup of GCB-DLBCL characterized by a cell-of-origin from the intermediate-/dark-zone of the germinal center. In a first step, a pathology re-review of the entire 347DLBCL cases from the BC Cancer cohort was performed by a panel of expert hematopathologists, confirming that DHITsig-pos tumors were indeed of DLBCL morphology. There were no morphological features that distinguished these tumors from DHITsig-neg tumors nor was the proliferation index (Ki67) significantly different between DHITsig groups (FIG. 9A).

In the Lymph2Cx assay, low linear predictor scores (LPS) provide an assignment to the GCB group while high scores result in an ABC assignment. Among the GCB DLBCLs, DHITsig-pos cases had significantly lower LPSs than DHITisg-neg (P<0.001, FIG. 9B). Moreover, DHITsig-pos tumors were universally positive for CD10 (MME) staining and the vast majority were MUM1 (IRF4) negative. CD10+/MUM1-cases were significantly more frequent in DHITsig-pos tumors (P<0.001; FIG. 9C). It has been previously demonstrated that most GCB-DLBCLs have a COO consistent with B-lymphocytes from the light zone (LZ) of the germinal center[25]. Given that the gene features in the Lymph2Cx and these IHC markers are associated with B-cell differentiation states, we considered whether the two DHITsig groups had gene expression patterns implying distinct putative COOs. Gene signatures associated with DZ, LZ and the more recently described intermediate zone (IZ), representing transition stage between these, were explored within the GCB-DLBCLs[26]. Strikingly, DHITsig-pos cases showed significantly lower expression of LZ genes compared to DHITsig-neg tumors (P<0.001) (FIG. 9D). The expression of genes in the DZ cluster were not statistically different between the two groups, while genes associated with the IZ had higher expression within the DHITsig-pos tumors. Furthermore, genes characteristic of the IZ are part of the 104-gene DHITsig model. Collectively, these findings demonstrate that while DHITsig-neg tumors have a LZ COO, we postulate that the COO for DHITsig-pos tumors are IZ B-cells transitioning from the LZ to the DZ.

Figure 10:
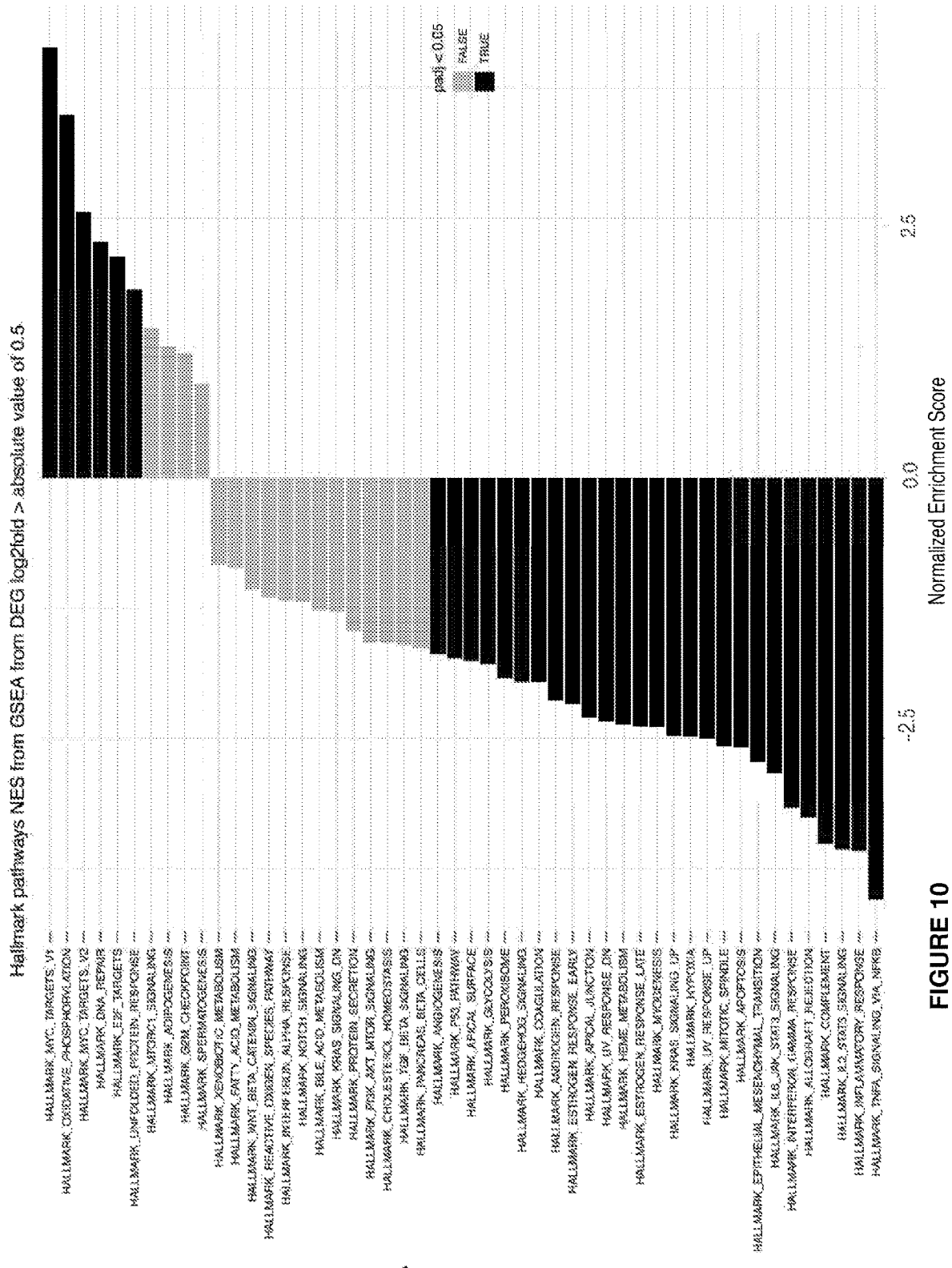
FIG. 10 shows the bar plot of the gene set enrichment analysis (GSEA). This analysis include differential expression genes between DHITsig-pos and -neg groups with FDR<0.1, and log 2 Fold Change>abs(0.5).

Gene set enrichment analysis was then used to further uncover additional biological differences between DHITsig-pos and -neg tumors. We found that DHITsig-pos cases demonstrated overexpression of MYC and E2F targets and genes associated with oxidative phosphorylation and MTORC1 signaling (FIG. 10). Conversely, DHITsig-pos tumors exhibit lower expression of genes associated with apoptosis, TNF-alpha signaling via NF-kB and decreased IL6/JAK/STAT3—processes up-regulated in centrocytes. DHITsig-pos cases also exhibited lower expression of immune and inflammation signatures. Consistently, tumor-infiltrating lymphocytes, especially CD4-positive T-cells, had significantly lower representation in DHITsig-pos cases relative to other GCBs (FIG. 11A). Loss of surface MHC class I and class II protein expression was also more frequent in DHITsig-pos cases (Fisher's exact test for MHC-I and MHC-II; 61% vs 40%; P=0.020, 44% vs 14%; P<0.001, respectively; FIG. 11B) with 68% of DHITsig-pos tumors having loss of either MHC class I or class II expression. Finally, we identified that all representative GCB-DLBCL cell lines tested belonged to the DHITsig-pos subgroup (FIG. 12), consistent with the notion that DHITsig-pos tumors harbor strong cell-autonomous survival and proliferation signals and reduced dependence on the microenvironment.

Figure 12:
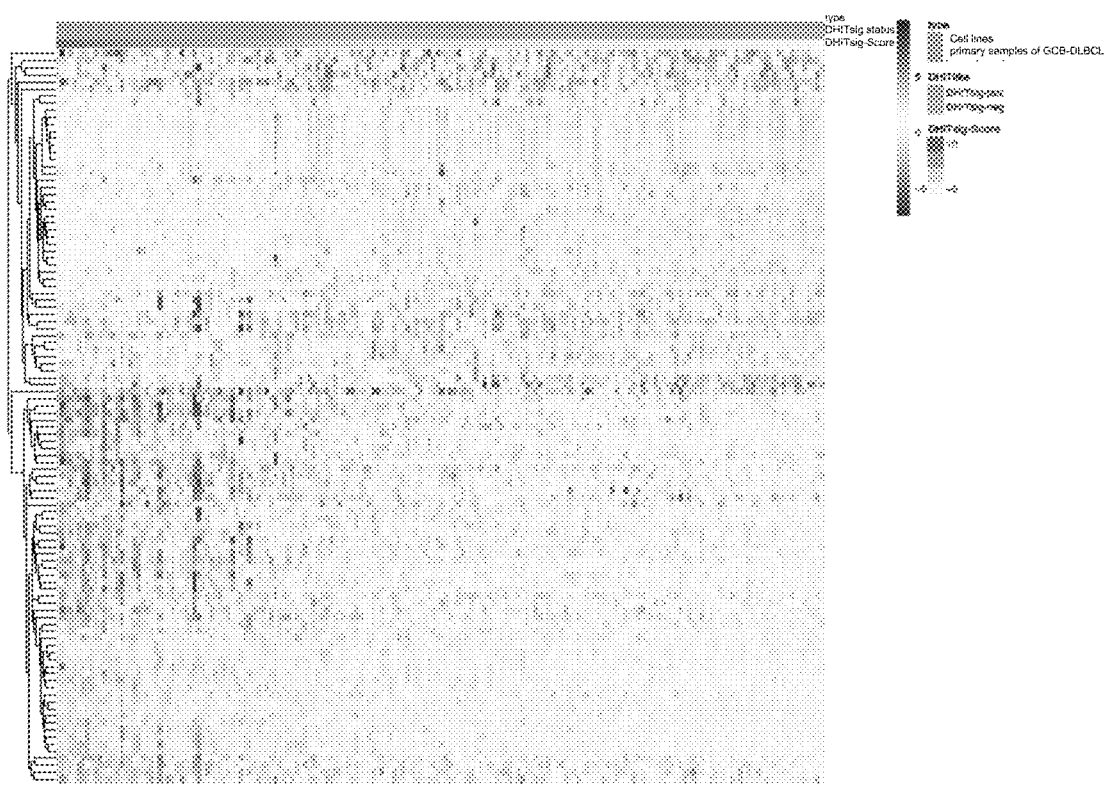
FIG. 12 shows a heatmap of the result of clustering of primary samples with GCB-DLBCL along with 8 GCB-DLBCL cell lines (Pfeiffer, Toledo, SU-DHL-8, WSU-NHL, HT, SU-DHL-5, SU-DHL-4, SU-DHL-10) by DHIT signature.

The genes associated with the relative gene expression profiles shown in FIG. 12 are, in order from top to bottom: HRK, NK2, JCHAIN, CD24, SUGCT, SOX9, EIF4EBP3, SGCE, DANCR, LRRC75A-AS1, UQCRH, RPL35, RPS8, RPL13, RPL6, RPL7, PIK3CD-AS2, SNHG19, FHIT, MYC, SMARCB1, CTD-3074O7.5, AFMID, FAM216A, SNHG17, SNHG11, SNHG7, ATF4, NMRAL1, SFXN4, PPP1R14B, GAMT, LINC00957, QRSL1, SYBU, TNFSF8, RGCC, SMIM14, OR13A1, ALOX5, SPTBN2, HAGHL, CCDC78, TERT, SLC29A2, MACROD1, SLC25A27, PEG10, CCL17, IRF4, BCL2A1, EBI3, CR2, LTA, CD80, GNG2, SIAH2, CDK5R1, SEMA7A, DGKG, MIR155HG, FCRL5, SIGLEC14, CCL22, COBLL1, IL10RA, PTPRJ, PARP15, ASS1P1, GPR137B, MREG, ADTRP, SGPP2, IL21R, BATF, DOCK10, LY75, HMSD, ETV5, ANKRD33B, POU3F1, GALNT6, CPEB4, TLE4, CAB39, ARPC2, VASP, ARHGAP25, VOPP1, RFFL, ST8SIA4, ARID3B, WDFY1, ALS2, HIVEP1, TACC1, CFLAR, NCOA1, MVP, STAT3, RASGRF1, ACPP, MYEOV, and AC104699.1.

The Mutational Landscape of DHITsig-Pos GCB-DLBCL

Figure 11C:
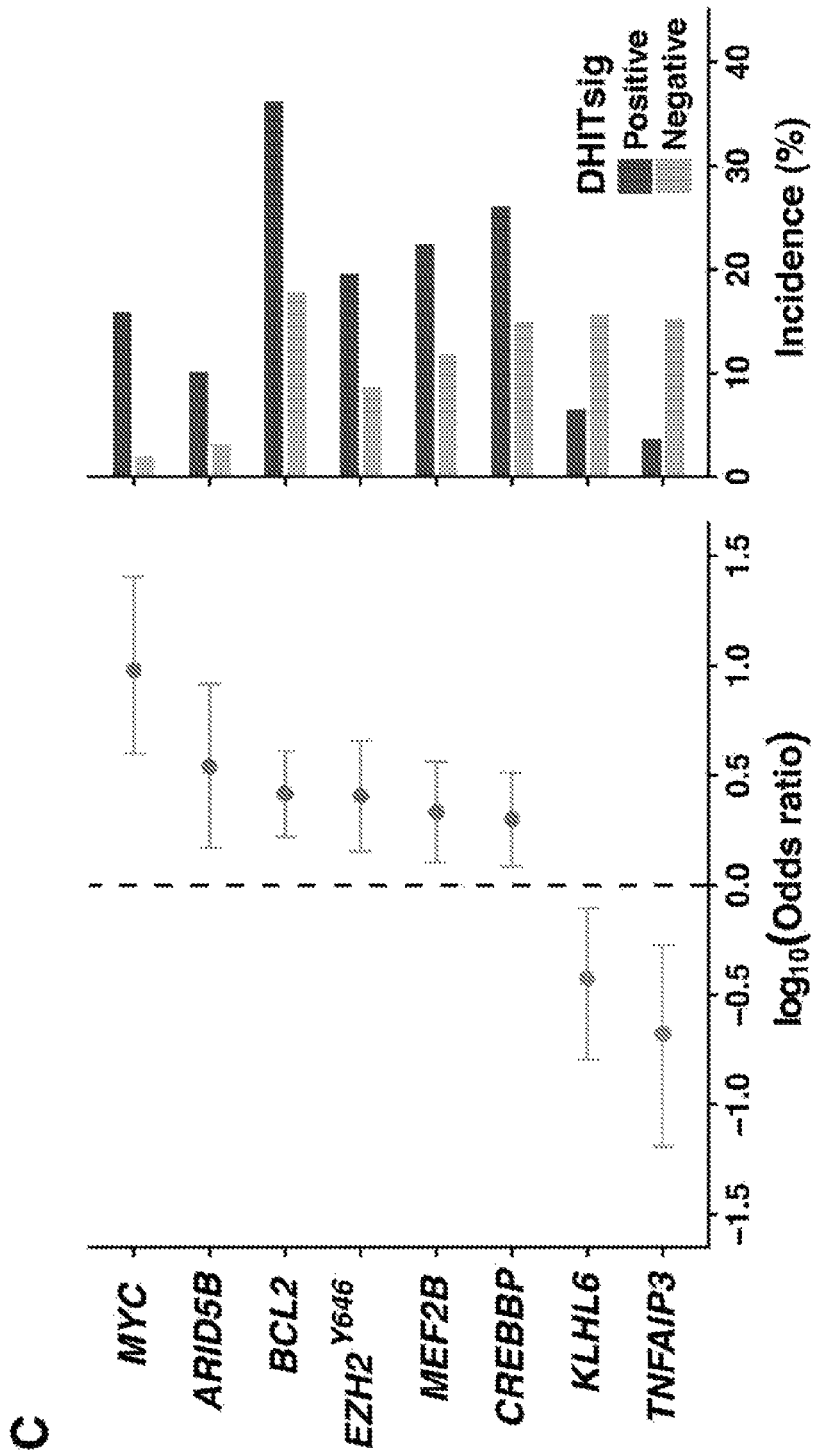
FIG. 11C shows the genetic, molecular and phenotypic features of DHIT signature by Forest plots summarizing the results of Fisher's exact tests comparing the frequency of mutations affecting individual genes in DHITsig-neg (left) and DHITsig-pos (right) GCB-DLBCL tumors. Significantly enriched genes in either DHITsig-pos or DHITsig-neg cases (FDR<0.10) are represented. Log 10 odds ratios and 95% confidence intervals are shown (left panel). Bar plots representing the frequency of mutations in either DHITsig-pos or -neg groups (right panel).

We next sought genetic features associated with DHITsig status within GCB-DLBCL. For this, we used the combined mutation data derived from 569 unique GCB-DLBCL cases in 3 cohorts (BC Cancer, Reddy et al and Schmitz et al). Along with the expected enrichment of mutations in MYC and BCL2 (FDR<0.001), mutations affecting CREBBP, EZH2$^{Y646}$, MEF2B and ARID5B were more frequent in DHITsig-pos tumors (all FDR<0.10). In contrast, the mutations of TNFAIP3 and NFKBIE were more common among DHITsig-neg GCB tumors (FDR<0.01, <0.14, respectively; FIG. 11C, Table 9).

TABLE 9

The association between mutation and DHIT signature

| Gene | Unmutated DHITsig-neg | Mutated DHIT sig-neg | Unmutated DHITsig-pos | Mutated DHIT sig-pos | p. value | Odds Ratio | 95% CI lower bound | 95% CI upper bound | FDR |
|---|---|---|---|---|---|---|---|---|---|
| MYC_Nonsyn | 419 | 13 | 111 | 34 | 1.25E-12 | 9.820825484 | 4.857358277 | 21.00268828 | 1.49E-10 |
| BCL2_Nonsyn | 343 | 89 | 80 | 65 | 3.75E-08 | 3.124344249 | 2.049307836 | 4.767677893 | 1.88E-06 |
| CREBBP_Nonsyn | 347 | 85 | 82 | 63 | 4.70E-08 | 3.12927341 | 2.045104801 | 4.7918902 | 1.88E-06 |
| EZH2_Codon646 | 368 | 64 | 98 | 47 | 8.95E-06 | 2.752017052 | 1.73204953 | 4.360818696 | 0.000268613 |
| CD58_Nonsyn | 391 | 41 | 144 | 1 | 6.98E-05 | 0.066378949 | 0.001630367 | 0.398974003 | 0.00167485 |
| DDX3X_Nonsyn | 411 | 21 | 123 | 22 | 0.00015669 | 3.491062439 | 1.766157157 | 6.924000984 | 0.003133805 |
| TNFAIP3_Nonsyn | 370 | 62 | 139 | 6 | 0.000531404 | 0.258050835 | 0.089175894 | 0.612963701 | 0.009109782 |
| BCL7A_Nonsyn | 387 | 45 | 113 | 32 | 0.000643524 | 2.431052987 | 1.423674832 | 4.119645271 | 0.009652867 |
| TP53_Nonsyn | 365 | 67 | 106 | 39 | 0.002917017 | 2.001711691 | 1.238786855 | 3.208568744 | 0.038893564 |
| KMT2D_Nonsyn | 289 | 143 | 77 | 68 | 0.003768831 | 1.782941592 | 1.193360985 | 2.662760747 | 0.045225971 |
| KLHL6_Nonsyn | 367 | 65 | 136 | 9 | 0.005945417 | 0.374162835 | 0.159334315 | 0.782255435 | 0.064859099 |
| STAT3_Nonsyn | 390 | 42 | 141 | 4 | 0.007011691 | 0.263892808 | 0.067531259 | 0.746770973 | 0.065908505 |
| NFKBIE_Nonsyn | 395 | 37 | 142 | 3 | 0.007140088 | 0.225923653 | 0.043892844 | 0.731089884 | 0.065908505 |
| TET2_Nonsyn | 377 | 55 | 138 | 7 | 0.007820615 | 0.348197908 | 0.13059391 | 0.791670495 | 0.067033847 |
| BCR_Nonsyn | 406 | 26 | 127 | 18 | 0.017745663 | 2.209703941 | 1.102546986 | 4.345119508 | 0.139684815 |
| RB1_Nonsyn | 418 | 14 | 133 | 12 | 0.018624642 | 2.688358479 | 1.106239126 | 6.436492655 | 0.139684815 |
| MEF2B_Codon83 | 413 | 19 | 131 | 14 | 0.023334282 | 2.319071146 | 1.044607487 | 5.03365839 | 0.164712575 |
| PRDM1_Nonsyn | 418 | 14 | 145 | 0 | 0.026275113 | 0 | 0 | 0.883348807 | 0.175167421 |
| C10orf12_Nonsyn | 400 | 32 | 125 | 20 | 0.028280352 | 1.997331452 | 1.043017581 | 3.748163799 | 0.17649257 |
| NFKBIA_Nonsyn | 393 | 39 | 140 | 5 | 0.029415428 | 0.360389281 | 0.108698959 | 0.940814323 | 0.17649257 |
| TMSB4X_Nonsyn | 385 | 47 | 138 | 7 | 0.031785276 | 0.416028585 | 0.154919013 | 0.955753342 | 0.18163015 |
| P2RY8_Nonsyn | 211 | 26 | 72 | 2 | 0.034357898 | 0.226151464 | 0.025394888 | 0.941649624 | 0.181806676 |
| UBE2A_Nonsyn | 413 | 19 | 144 | 1 | 0.03484628 | 0.151239991 | 0.0036122 | 0.968547714 | 0.181806676 |
| CD70_Nonsyn | 402 | 30 | 142 | 3 | 0.036369695 | 0.283520641 | 0.054546692 | 0.933474198 | 0.181848475 |
| GNA13Nonsyn | 340 | 92 | 102 | 43 | 0.04203929 | 1.556702613 | 0.991214374 | 2.424407578 | 0.20178859 |
| EZH2_Nonsyn | 423 | 9 | 137 | 8 | 0.045781736 | 2.738774498 | 0.900426274 | 8.172288332 | 0.211300318 |
| CARD11_Nonsyn | 365 | 67 | 132 | 13 | 0.052042055 | 0.537035302 | 0.263038883 | 1.022251258 | 0.231298024 |
| BCL10_Nonsyn | 414 | 18 | 144 | 1 | 0.055765107 | 0.160023725 | 0.003811414 | 1.031628593 | 0.234999339 |
| FOXO1_Nonsyn | 394 | 38 | 124 | 21 | 0.057636007 | 1.753985397 | 0.940542369 | 3.199216193 | 0.234999339 |
| SGK1_Nonsyn | 333 | 99 | 123 | 22 | 0.058749835 | 0.602171398 | 0.345051049 | 1.015074574 | 0.234999339 |
| BTK_Nonsyn | 410 | 22 | 131 | 14 | 0.071632053 | 1.989031052 | 0.9131556 | 4.200862101 | 0.272306504 |
| HLA.B_Nonsyn | 113 | 14 | 31 | 0 | 0.07354995 | 0 | 0 | 1.17910625 | 0.272306504 |
| MYD88_Nonsyn | 406 | 26 | 142 | 3 | 0.076833952 | 0.330407269 | 0.063053309 | 1.103096629 | 0.272306504 |
| SOCS1_Nonsyn | 332 | 100 | 122 | 23 | 0.078319318 | 0.626376351 | 0.362505801 | 1.048042871 | 0.272306504 |
| ACTB_Nonsyn | 383 | 49 | 136 | 9 | 0.080439873 | 0.517769156 | 0.217666536 | 1.10209368 | 0.272306504 |
| IRF4_Nonsyn | 411 | 21 | 143 | 2 | 0.083647979 | 0.274143563 | 0.030792862 | 1.144723108 | 0.272306504 |
| CIITA_Nonsyn | 399 | 33 | 140 | 5 | 0.083961172 | 0.432330894 | 0.129202044 | 1.144999992 | 0.272306504 |
| SPEN_Nonsyn | 384 | 48 | 136 | 9 | 0.107059476 | 0.529920005 | 0.222534245 | 1.129667007 | 0.338082619 |
| BTG2_Nonsyn | 379 | 53 | 134 | 11 | 0.129053211 | 0.587503021 | 0.268570406 | 1.180703819 | 0.394585993 |
| CD274_Nonsyn | 418 | 14 | 144 | 1 | 0.131528664 | 0.20769927 | 0.004874128 | 1.388311231 | 0.394585993 |
| HVCN1_Nonsyn | 418 | 14 | 136 | 9 | 0.139221598 | 1.973257888 | 0.735911732 | 5.021991976 | 0.407477847 |
| NOTCH1_Nonsyn | 286 | 19 | 102 | 12 | 0.144771416 | 1.768169455 | 0.754453053 | 3.994560464 | 0.413632616 |
| BCL6_Nonsyn | 383 | 49 | 135 | 10 | 0.153919376 | 0.579475317 | 0.254390456 | 1.199525646 | 0.429542444 |
| NLRC5_Nonsyn | 410 | 22 | 142 | 3 | 0.157991837 | 0.394245455 | 0.074430072 | 1.341809701 | 0.430886828 |
| CD36_Nonsyn | 409 | 23 | 142 | 3 | 0.161933297 | 0.376205857 | 0.071237241 | 1.273479248 | 0.431822125 |
| SETD2_Nonsyn | 407 | 25 | 132 | 13 | 0.180500896 | 1.601893088 | 0.730571913 | 3.361629506 | 0.460200289 |
| NFKBIZ_3UTR | 100 | 10 | 42 | 1 | 0.182862723 | 0.239721557 | 0.005364879 | 1.78144891 | 0.460200289 |
| MEF2B_Nonsyn | 397 | 35 | 128 | 17 | 0.184360895 | 1.505316251 | 0.763584089 | 2.869737693 | 0.460200289 |
| RFXAP_Nonsyn | 425 | 7 | 140 | 5 | 0.187915118 | 2.165025109 | 0.532967533 | 8.067929531 | 0.460200289 |
| CD79B_Nonsyn | 294 | 11 | 113 | 1 | 0.193405243 | 0.237067057 | 0.005451488 | 1.665450035 | 0.464172583 |
| B2M_Nonsyn | 331 | 101 | 119 | 26 | 0.20254707 | 0.716428569 | 0.425013183 | 1.176267474 | 0.476581341 |

TABLE 9-continued

The association between mutation and DHIT signature

| Gene | Unmutated DHITsig-neg | Mutated DHIT sig-neg | Unmutated DHITsig-pos | Mutated DHIT sig-pos | p. value | Odds Ratio | 95% CI lower bound | 95% CI upper bound | FDR |
|---|---|---|---|---|---|---|---|---|---|
| BLNK__Nonsyn | 235 | 2 | 72 | 2 | 0.240770976 | 3.248465571 | 0.231684442 | 45.54764416 | 0.555625329 |
| HIST1H1C__Nonsyn | 380 | 52 | 122 | 23 | 0.254075374 | 1.376870091 | 0.77073945 | 2.400736948 | 0.562334348 |
| KLHL14__Nonsyn | 311 | 11 | 96 | 6 | 0.258317165 | 1.764347461 | 0.521488772 | 5.368358423 | 0.562334348 |
| NOTCH2__Nonsyn | 311 | 11 | 96 | 6 | 0.258317165 | 1.764347461 | 0.521488772 | 5.368358423 | 0.562334348 |
| MKI67__Nonsyn | 398 | 34 | 138 | 7 | 0.264502417 | 0.594251852 | 0.217230569 | 1.403006867 | 0.562334348 |
| ZC3H12A__Nonsyn | 416 | 16 | 143 | 2 | 0.267108815 | 0.364094012 | 0.040137141 | 1.578997815 | 0.562334348 |
| OSBPL10__Nonsyn | 309 | 13 | 95 | 7 | 0.282232514 | 1.748797596 | 0.573550056 | 4.878632169 | 0.583929339 |
| UNC5D__Nonsyn | 295 | 10 | 113 | 1 | 0.302101413 | 0.261631875 | 0.005967491 | 1.876829452 | 0.6079871 |
| ETV6__Nonsyn | 311 | 11 | 101 | 1 | 0.30836978 | 0.280503969 | 0.006444381 | 1.97355432 | 0.6079871 |
| MYD88__Codon273 | 421 | 11 | 144 | 1 | 0.311232734 | 0.266193279 | 0.006136629 | 1.860777735 | 0.6079871 |
| TNFSF9__Nonsyn | 108 | 2 | 41 | 2 | 0.314126668 | 2.614939619 | 0.183962354 | 37.17594104 | 0.6079871 |
| CCND3__Nonsyn | 407 | 25 | 133 | 12 | 0.326880684 | 1.467814193 | 0.652884897 | 3.131819356 | 0.621734785 |
| PPP1R9B__Nonsyn | 316 | 6 | 102 | 0 | 0.343031492 | 0 | 0 | 2.679140066 | 0.621734785 |
| TMEM30A__Nonsyn | 399 | 33 | 138 | 7 | 0.344143153 | 0.613764232 | 0.223918294 | 1.45339806 | 0.621734785 |
| GRHPR__Nonsyn | 426 | 6 | 145 | 0 | 0.345056931 | 0 | 0 | 2.527764273 | 0.621734785 |
| BRAF__Nonsyn | 411 | 21 | 141 | 4 | 0.351785889 | 0.555694768 | 0.136328341 | 1.68636074 | 0.621734785 |
| XP01__Nonsyn | 423 | 9 | 140 | 5 | 0.356688373 | 1.676890513 | 0.433971345 | 5.68203085 | 0.621734785 |
| PIM1__Nonsyn | 360 | 72 | 126 | 19 | 0.357497501 | 0.754308181 | 0.412518837 | 1.325177196 | 0.621734785 |
| MY0M2__Nonsyn | 408 | 24 | 134 | 11 | 0.420951286 | 1.394659123 | 0.59999997 | 3.051714373 | 0.711466962 |
| S1PR2__Nonsyn | 408 | 24 | 134 | 11 | 0.420951286 | 1.394659123 | 0.59999997 | 3.051714373 | 0.711466962 |
| STAT6__Nonsyn | 405 | 27 | 133 | 12 | 0.444309778 | 1.352628458 | 0.606393864 | 2.854032727 | 0.740516297 |
| PIM2__Nonsyn | 424 | 8 | 144 | 1 | 0.461652675 | 0.368516801 | 0.008242047 | 2.78857678 | 0.758881109 |
| MPEG1__Nonsyn | 412 | 20 | 141 | 4 | 0.471182323 | 0.584855289 | 0.142920802 | 1.787268978 | 0.76253806 |
| VPS13B__Nonsyn | 304 | 18 | 94 | 8 | 0.476586287 | 1.436023093 | 0.522844379 | 3.607063605 | 0.76253806 |
| HLA.DMB__Nonsyn | 116 | 11 | 27 | 4 | 0.496600381 | 1.557395604 | 0.335806842 | 5.793412636 | 0.784105865 |
| FAS__Nonsyn | 390 | 42 | 134 | 11 | 0.508956012 | 0.762621575 | 0.343869932 | 1.561381931 | 0.7931782 |
| EP300__Nonsyn | 389 | 43 | 128 | 17 | 0.532545988 | 1.201052965 | 0.619521621 | 2.239816217 | 0.807131514 |
| ARID5B__Nonsyn | 309 | 13 | 100 | 2 | 0.538087676 | 0.476048872 | 0.05131109 | 2.158248002 | 0.807131514 |
| TRRAP__Nonsyn | 309 | 13 | 100 | 2 | 0.538087676 | 0.476048872 | 0.05131109 | 2.158248002 | 0.807131514 |
| CPS1__Nonsyn | 422 | 10 | 140 | 5 | 0.545429483 | 1.505972194 | 0.396941415 | 4.935622726 | 0.808043678 |
| MTOR__Nonsyn | 310 | 12 | 97 | 5 | 0.570003625 | 1.330655403 | 0.358130851 | 4.184289473 | 0.834151647 |
| CD83__Nonsyn | 398 | 34 | 136 | 9 | 0.587033133 | 0.77499448 | 0.318498822 | 1.703513521 | 0.8416822 |
| HNF1B__Nonsyn | 319 | 3 | 100 | 2 | 0.597911474 | 2.122283652 | 0.174959242 | 18.79337914 | 0.8416822 |
| IL16__Nonsyn | 319 | 3 | 100 | 2 | 0.597911474 | 2.122283652 | 0.174959242 | 18.79337914 | 0.8416822 |
| IRF8__Nonsyn | 359 | 73 | 124 | 21 | 0.603205577 | 0.833091429 | 0.466578384 | 1.437616347 | 0.8416822 |
| DTX1__Nonsyn | 299 | 23 | 93 | 9 | 0.666850028 | 1.257361612 | 0.494149047 | 2.942532949 | 0.919793142 |
| CD79B__Codon197 | 426 | 6 | 144 | 1 | 0.686010207 | 0.493529717 | 0.01065012 | 4.120613363 | 0.925078858 |
| KLHL21__Nonsyn | 315 | 7 | 101 | 1 | 0.686100153 | 0.44619469 | 0.009794061 | 3.540778479 | 0.925078858 |
| PCLO__Nonsyn | 361 | 71 | 119 | 26 | 0.700730554 | 1.11068686 | 0.648657037 | 1.858574459 | 0.932376878 |
| FAT4__Nonsyn | 355 | 77 | 117 | 28 | 0.709553358 | 1.103143868 | 0.655558751 | 1.818277217 | 0.932376878 |
| BIRC6__Nonsyn | 397 | 35 | 135 | 10 | 0.722971017 | 0.840462642 | 0.361145767 | 1.79267724 | 0.932376878 |
| HIST1H1E__Nonsyn | 342 | 90 | 117 | 28 | 0.722974291 | 0.909539337 | 0.544395605 | 1.486153393 | 0.932376878 |
| BCL11A__Nonsyn | 314 | 8 | 99 | 3 | 0.730361888 | 1.188925832 | 0.199363176 | 5.074784484 | 0.932376878 |
| TRIP12__Nonsyn | 312 | 10 | 98 | 4 | 0.750810457 | 1.272701502 | 0.284974704 | 4.536822423 | 0.941133237 |
| NFKBIZ__Nonsyn | 422 | 10 | 141 | 4 | 0.758277968 | 1.196815081 | 0.269710147 | 4.231057395 | 0.941133237 |
| CXCR4__Nonsyn | 420 | 12 | 142 | 3 | 0.771373034 | 0.739808997 | 0.132122343 | 2.79515557 | 0.941133237 |
| UNC5C__Nonsyn | 419 | 13 | 142 | 3 | 0.77164424 | 0.68136532 | 0.122791064 | 2.52905036 | 0.941133237 |
| SIN3A__Nonsyn | 420 | 12 | 140 | 5 | 0.776434921 | 1.249509089 | 0.338778814 | 3.893437553 | 0.941133237 |
| SETD1B__Nonsyn | 305 | 17 | 96 | 6 | 0.803936151 | 1.120894388 | 0.351725616 | 3.086725119 | 0.964723381 |
| TNFRSF14__Nonsyn | 324 | 108 | 107 | 38 | 0.825342626 | 1.06530119 | 0.67287932 | 1.665012933 | 0.9806051 |
| POU2F2Nonsyn | 408 | 24 | 136 | 9 | 0.836304238 | 1.124750348 | 0.448697378 | 2.582121298 | 0.982198827 |
| IL4R__Nonsyn | 404 | 28 | 137 | 8 | 0.843053993 | 0.842790642 | 0.324039409 | 1.955348964 | 0.982198827 |
| ZFP36L1__Nonsyn | 387 | 45 | 131 | 14 | 0.875010431 | 0.919217387 | 0.450848136 | 1.772420513 | 1 |
| BTG1__Nonsyn | 383 | 49 | 130 | 15 | 0.878624406 | 0.90204441 | 0.453902373 | 1.702525447 | 1 |
| CHST2__Nonsyn | 319 | 3 | 102 | 0 | 1 | 0 | 0 | 7.663469221 | 1 |
| USP7__Nonsyn | 413 | 19 | 139 | 6 | 1 | 0.938383367 | 0.300559109 | 2.507040029 | 1 |
| ARID1A__Nonsyn | 387 | 45 | 130 | 15 | 1 | 0.992319378 | 0.496540314 | 1.886750942 | 1 |
| C1orf186__Nonsyn | 126 | 1 | 31 | 0 | 1 | 0 | 0 | 159.3787992 | 1 |
| ETS1__Nonsyn | 425 | 7 | 143 | 2 | 1 | 0.849384896 | 0.085164353 | 4.529215376 | 1 |
| FOXC1__Nonsyn | 316 | 6 | 100 | 2 | 1 | 1.053207342 | 0.102405294 | 6.009937868 | 1 |
| HIST1H2BK__Nonsyn | 308 | 14 | 98 | 4 | 1 | 0.898182387 | 0.210376895 | 2.94839291 | 1 |
| HIST1H3B__Nonsyn | 291 | 14 | 109 | 5 | 1 | 0.953591476 | 0.262446793 | 2.886403618 | 1 |
| KRAS__Nonsyn | 420 | 12 | 141 | 4 | 1 | 0.992919129 | 0.229691647 | 3.34434941 | 1 |
| NFKB1__Nonsyn | 423 | 9 | 142 | 3 | 1 | 0.992969032 | 0.170579039 | 4.050482112 | 1 |
| NOL9__Nonsyn | 315 | 7 | 100 | 2 | 1 | 0.90021859 | 0.089861565 | 4.83026798 | 1 |
| PTPN1__Nonsyn | 424 | 8 | 143 | 2 | 1 | 0.741627251 | 0.075877885 | 3.776243543 | 1 |
| TAP1__Nonsyn | 123 | 4 | 31 | 0 | 1 | 0 | 0 | 6.287317334 | 1 |
| TBL1XR1__Nonsyn | 418 | 14 | 140 | 5 | 1 | 1.066212134 | 0.295164001 | 3.204345068 | 1 |
| WEE1__Nonsyn | 313 | 9 | 99 | 3 | 1 | 1.053744689 | 0.180020134 | 4.33020225 | 1 |

Translation of the DHIT Signature into a Clinically Relevant Assay

Figure 13:
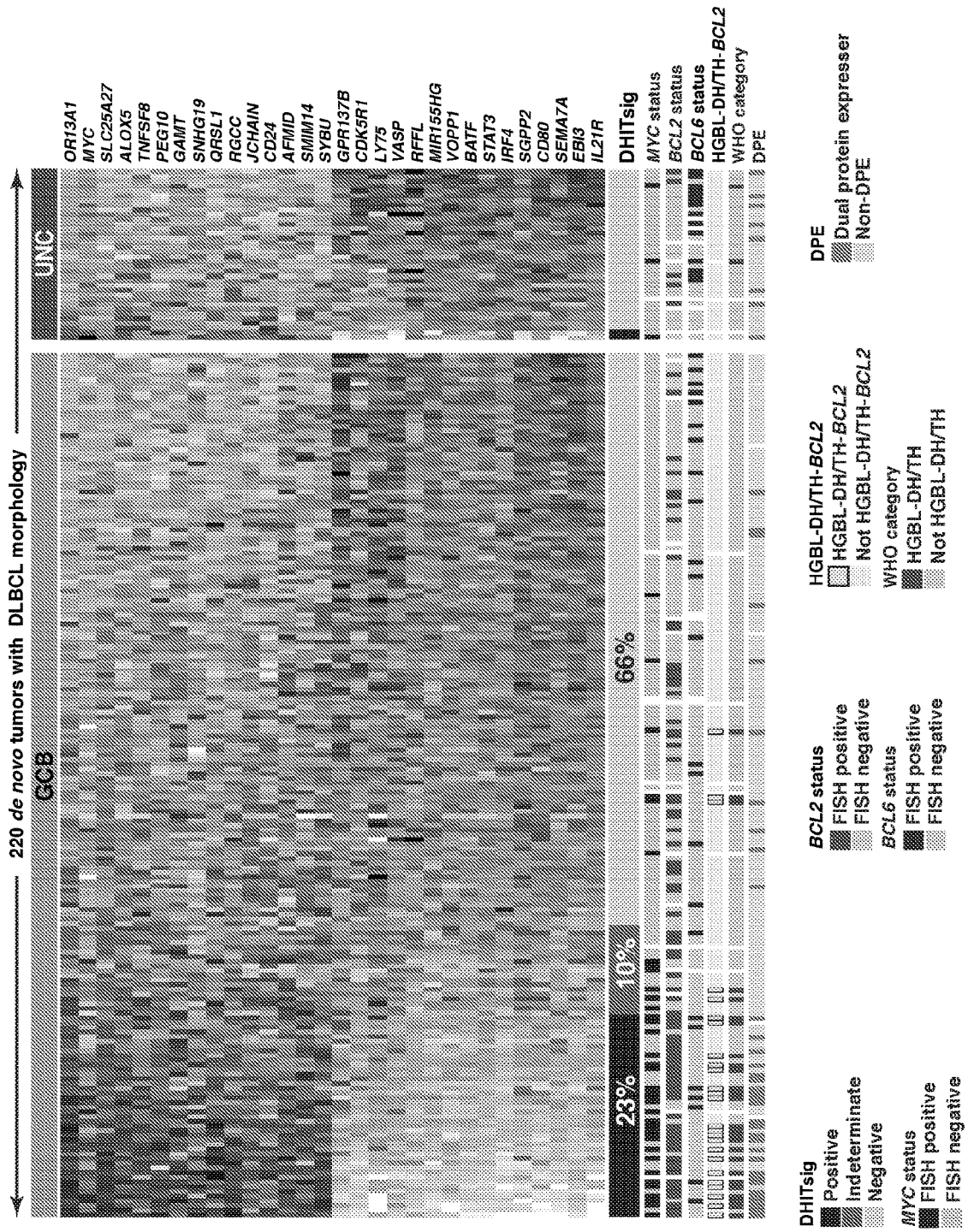
FIG. 13 shows the gene expression-based model for the DHIT signature in which the DLBCL90 assay is shown in the form of a heatmap, with the 30 informative genes shown as rows, and the cases shown as columns, separated into 220 GCB- and Unclassified DLBCLs. The tumors are arrayed from highest DHIT sig score on the left to lowest DHITsig score on the right. DHITsig groups identified by the signature are shown below the heat map.

To provide an assay applicable to routinely available biopsies, the 104-gene RNAseq model was reduced to a 30-gene module. This module was added to the Lymph3Cx[27], which in turn is an extension of Lymph2Cx containing a module to distinguish primary mediastinal B-cell lymphomas. This NanoString-based assay, named DLBCL90, assigns tumors into DHITsig-pos and DHITsig-neg groups using a Bayes rule with 20% and 80% probability thresholds, with an "Indeterminate" group (DHITsig-ind) where the tumor could not be assigned with sufficient confidence. This was applied to 171 GCB-DLBCL tumors from the 347-patient cohort (including 156 from the discovery cohort), giving 26% DHITsig-pos, 64% DHITsig-neg and 10% DHITsig-ind, with a frank misclassification rate of 3% against the RNAseq comparator (FIG. 3). The integrity of the Lymph2Cx assay was maintained (FIGS. 8A-B). The assay was then applied to the remaining available 322 FFPE biopsies from the 347 de novo DLBCL cohort, showing that the DHITsig was not seen in ABC-DLBCL with 4/102 (4%) being DHITsig-ind (FIG. 13, ABC-DLBCL results not shown). The prognostic significance for TTP, DSS, PFS and OS of DHITsig was maintained (all, $P<0.001$). As the DHITsig-ind group had similar outcomes to DHITsig-pos, these two groups are shown together in FIG. 15A-D. Importantly, the assay identified a group with very good prognosis with DHITsig-neg GCB-DLBCLs exhibiting a DSS of 90% at five years. Although small numbers preclude a definitive statement, the patients with rare HGBL-DH/TH-BCL2 and DHITsig-neg status experienced good outcomes with all three patients in remission at 9.2 years.

To validate the association between the DHITsig and HGBL-DH/TH-BCL2, DLBCL90 was applied to 88 tFL with DLBCL morphology. Within these 88 tFL cases, 11 of the 25 DHITsig-pos tumors were HGBL-DH/TH-BCL2 compared with 0/50 in the DHITsig-neg group. Within the DHITsig-ind group, 4/13 tumors were HGBL-DH/TH-BCL2 (FIG. 4B). Finally, the DLBCL90 assay was applied to 26 HGBL tumors, including 7 classified as high-grade B-cell lymphoma NOS and 18 classified as HGBL-DH/TH with high-grade morphology—one case could not be assigned due to an unknown MYC rearrangement status. Among these tumors, the vast majority were assigned to the DHITsig-pos group (23 (88%)) with 3 (12%) being DHITsig-ind (FIG. 4C).

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Lenz G, Wright G, Dave S S, et al: Stromal gene signatures in large-B-cell lymphomas. N Engl J Med 359:2313-23, 2008
2. Shipp M A, Ross K N, Tamayo P, et al: Diffuse large B-cell lymphoma outcome prediction by gene-expression profiling and supervised machine learning. Nat Med 8:68-74, 2002
3. Alizadeh A A, Eisen M B, Davis R E, et al: Distinct types of diffuse large B-cell lymphoma identified by gene expression profiling. Nature 403:503-11, 2000
4. Swerdlow S H, Campo E, Pileri S A, et al: The 2016 revision of the World Health Organization (WHO) classification of lymphoid neoplasms. Blood 127:2375-2390, 2016
5. Scott D W, King R L, Staiger A M, et al: High-grade B-cell lymphoma with MYC and BCL2 and/or BCL6 rearrangements with diffuse large B-cell lymphoma morphology. Blood 131:2060-2064, 2018
6. Ennishi D, Mottok A, Ben-Neriah S, et al: Genetic profiling of MYC and BCL2 in diffuse large B-cell lymphoma determines cell-of-origin-specific clinical impact. Blood 129:2760-2770, 2017
7. Ott G, Rosenwald A, Campo E: Understanding MYC-driven aggressive B-cell lymphomas: pathogenesis and classification. Blood 122:575-583, 2015
8. Sarkozy C, Traverse-Glehen A, Coiffier B: Double-hit and double-protein-expression lymphomas: aggressive and refractory lymphomas. Lancet Oncol 16:e555-e567, 2015
9. Johnson N A, Slack G W, Savage K J, et al: Concurrent expression of MYC and BCL2 in diffuse large B-cell lymphoma treated with rituximab plus cyclophosphamide, doxorubicin, vincristine, and prednisone. J Clin Oncol 30:3452-3459, 2012
10. Green T M, Young K H, Visco C, et al: Immunohistochemical double-hit score is a strong predictor of outcome in patients with diffuse large B-cell lymphoma treated with rituximab plus cyclophosphamide, doxorubicin, vincristine, and prednisone. J Clin Oncol 30:3460-3467, 2012
11. Johnson N A, Savage K J, Ludkovski O, et al: Lymphomas with concurrent BCL2 and MYC translocations: the critical factors associated with survival. Blood 114:2273-2279, 2009
12. Savage K J, Johnson N a, Ben-neriah S, et al: MYC gene rearrangements are associated with a poor prognosis in diffuse large B-cell lymphoma patients treated with R-CHOP chemotherapy. Blood 114:3533-3537, 2009
13. Pasqualucci L, Trifonov V, Fabbri G, et al: Analysis of the coding genome of diffuse large B-cell lymphoma. Nat Genet 43:830-7, 2011
14. Morin R D, Mendez-Lago M, Mungall A J, et al: Frequent mutation of histone-modifying genes in non-Hodgkin lymphoma. Nature 476:298-303, 2011
15. Morin R D, Mungall K, Pleasance E, et al: Mutational and structural analysis of diffuse large B-cell lymphoma using whole-genome sequencing. Blood 122:1256-65, 2013
16. Lohr J G, Stojanov P, Lawrence M S, et al: Discovery and prioritization of somatic mutations in diffuse large B-cell lymphoma (DLBCL) by whole-exome sequencing. Proc Natl Acad Sci USA 109:3879-3884, 2012
17. Schmitz R, Wright G W, Huang D W, et al: Genetics and pathogenesis of diffuse large B-cell lymphoma. N Engl J Med 378:1396-1407, 2018
18. Chapuy B, Stewart C, Dunford A J, et al: Molecular subtypes of diffuse large B cell lymphoma are associated with distinct pathogenic mechanisms and outcomes. Nat Med 24:679-690, 2018
19. Reddy A, Zhang J, Davis N S, et al: Genetic and functional drivers of diffuse large B cell lymphoma. Cell 171:481-494.e15, 2017
20. Kridel R, Mottok A, Farinha P, et al: Cell-of-origin of transformed follicular lymphoma. Blood 126:2118-2127, 2015

21. Arthur S, Jiang A, Grande B, et al: Genome-wide discovery of somatic coding and regulatory variants in Diffuse Large B-cell Lymphoma. Nat Commun 9: 4001, 2018.
22. Ortega-Molina A, Boss I W, Canela A, et al: The histone lysine methyltransferase KMT2D sustains a gene expression program that represses B cell lymphoma development. Nat Med 21:1199-1208, 2015
23. Jiang Y, Ortega-Molina A, Geng H, et al: CREBBP Inactivation Promotes the Development of HDAC3-Dependent Lymphomas. Cancer Discov 7:38-53, 2017
24. Scott D W, Mottok A, Ennishi D, et al: Prognostic significance of diffuse large B-cell lymphoma cell of origin determined by digital gene expression in formalin-fixed paraffin-embedded tissue biopsies. J Clin Oncol 33:2848-2856, 2015
25. Victora G D, Dominguez-Sola D, Holmes A B, et al: Identification of human germinal center light and dark zone cells and their relationship to human B-cell lymphomas. Blood 120:2240-8, 2012
26. Milpied P, Cervera-Marzal I, Mollichella M-L, et al: Human germinal center transcriptional programs are desynchronized in B cell lymphoma. Nat Immunol 19:1013-1024, 2018
27. Mottok A, Wright G, Rosenwald A, et al: Molecular classification of primary mediastinal large B-cell lymphoma using routinely available tissue specimens. Blood 132:2401-2405, epub Sep. 26, 2018
28. Dominguez-Sola D, Victora G D, Ying C Y, et al: The proto-oncogene MYC is required for selection in the germinal center and cyclic reentry. Nat Immunol 13:1083-1091, 2012
29. Calado D P, Sasaki Y, Godinho S A, et al: The cell-cycle regulator c-Myc is essential for the formation and maintenance of germinal centers. Nat Immunol 13:1092-1100, 2012
30. Green M R, Kihira S, Liu C L, et al: Mutations in early follicular lymphoma progenitors are associated with suppressed antigen presentation. Proc Natl Acad Sci USA 112:E1116-25, 2015
31. Davids M S, Roberts A W, Seymour J F, et al: Phase i first-in-human study of venetoclax in patients with relapsed or refractory non-Hodgkin lymphoma. J Clin Oncol 35:826-833, 2017
32. Scott D W, Wright G W, Williams P M, et al: Determining cell-of-origin subtypes of diffuse large B-cell lymphoma using gene expression in formalin-fixed paraffin-embedded tissue. Blood 123:1214-1217, 2014
33. Cancer Genome Atlas Research Network: Comprehensive molecular characterization of gastric adenocarcinoma. Nature 513:202-9, 2014
34. Love M I, Huber W, Anders S: Moderated estimation of fold change and dispersion for RNA-seq data with DESeq2. Genome Biol 15:1-21, 2014
35. Sergushichev A: An algorithm for fast preranked gene set enrichment analysis using cumulative statistic calculation. bioRxiv 60012, 2016

What is claimed is:

1. A method for administering a therapy for a subject with an aggressive B-cell lymphoma comprising:
   determining the molecular subgroup of the aggressive B-cell lymphoma by preparing a gene expression profile from a biopsy obtained from the subject, the gene expression profile covering all of the following genes: AFMID, ALOX5, BATF, CD24, CD80, CDK5R1, EBI3, GAMT, GPR137B, IL21R, IRF4, JCHAIN, LY75, MIR155HG, MYC, OR13A1, PEG10, QRSL1, RFFL, RGCC, SEMA7A, SGPP2, SLC25A27, SMIM14, SNHG19, STAT3, SYBU, TNFSF8, VASP, and VOPP1, the gene expression profile being determined based on a level of a nucleic acid encoded by the gene;
   determining that the molecular subgroup of the aggressive B-cell lymphoma is a positive double hit signature (DHITsig-pos) lymphoma based upon detecting that:
      collectively OR13A1, MYC, SLC25A27, ALOX5, TNFSF8, PEG10, GAMT, SNHG19, QRSL1, RGCC, JCHAIN, CD24, AFMID, SMIM14, and SYBU are overexpressed in the biopsy; and
      collectively GPR137B, CDK5R1, LY75, VASP, RFFL, MIR155HG, VOPP1, BATF, STAT3, IRF4, SGPP2, CD80, SEMA7A, EBI3, and IL21R are underexpressed in the biopsy; and
   administering to the subject determined to have the DHITsig-pos lymphoma one or more of: dose intensive immunochemotherapy, a cell-based therapy, CAR T-cell therapy, a BCL2 inhibitor, an enhancer of zeste homolog 2 (EZH2 inhibitor), a histone deacetylase inhibitor, an arachidonate 5-lipoxygenase inhibitor, a Bruton's tyrosine kinase inhibitor, ibrutinib, a PIM kinase inhibitor, SGI-1776, belinostat, vorinostat, a PI3K inhibitor, copanlisib, buparlisib, a protein kinase C inhibitor, sotrastaurin, immunomodulatory drugs, lenalidomide, or an anti-CD20 antibody.

2. A method for administering a therapy for a subject with an aggressive B-cell lymphoma comprising:
   determining the molecular subgroup of the aggressive B-cell lymphoma by preparing a gene expression profile from a biopsy obtained from the subject, the gene expression profile covering all of the following genes: AFMID, ALOX5, BATF, CD24, CD80, CDK5R1, EBI3, GAMT, GPR137B, IL21R, IRF4, JCHAIN, LY75, MIR155HG, MYC, OR13A1, PEG10, QRSL1, RFFL, RGCC, SEMA7A, SGPP2, SLC25A27, SMIM14, SNHG19, STAT3, SYBU, TNFSF8, VASP, and VOPP1, the gene expression profile being determined based on a level of a nucleic acid encoded by the gene;
   determining that the molecular subgroup of the aggressive B-cell lymphoma is a negative double hit signature (DHITsig-neg) lymphoma based upon detecting that:
      collectively OR13A1, MYC, SLC25A27, ALOX5, TNFSF8, PEG10, GAMT, SNHG19, QRSL1, RGCC, JCHAIN, CD24, AFMID, SMIM14, and SYBU are underexpressed in the biopsy; and
      collectively GPR137B, CDK5R1, LY75, VASP, RFFL, MIR155HG, VOPP1, BATF, STAT3, IRF4, SGPP2, CD80, SEMA7A, EBI3, and IL21R are overexpressed in the biopsy; and
   administering to the subject determined to have the DHITsig-neg lymphoma rituximab, cyclophosphamide, doxorubicin hydrochloride, vincristine sulfate and prednisone (R-CHOP).

3. The method of claim 2 wherein the aggressive B-cell lymphoma is a germinal centre B-cell-like diffuse large B-cell lymphoma (GCB-DLBCL).

4. The method of claim 2 wherein the aggressive B-cell lymphoma is a high-grade B-cell lymphoma (HGBL).

5. The method of claim 1 wherein the aggressive B-cell lymphoma is a germinal centre B-cell-like diffuse large B-cell lymphoma (GCB-DLBCL).

6. The method of claim 1 wherein the aggressive B-cell lymphoma is a high-grade B-cell lymphoma (HGBL).

7. The method of claim 1 wherein determining the molecular subgroup of the aggressive B-cell lymphoma further comprises preparing a gene expression profile for one or more of the following genes in the biopsy: AC104699.1, ACPP, ADTRP, ALS2, ANKRD33B, ARHGAP25, ARID3B, ARPC2, ASS1P1, ATF4, BCL2A1, CAB39, CCDC78, CCL17, CCL22, CFLAR, COBLL1, CPEB4, CR2, CTD-3074O7.5, DANCR, DGKG, DOCK10, EI F4EBP3, ETV5, FAM216A, FCRL5, FHIT, GALNT6, GNG2, HAGHL, HIVEP1, HMSD, HRK, IL10RA, LINC00957, LRRC75A-AS1, LTA, MACROD1, MREG, MVP, MYEOV, NCOA1, NMRAL1, PARP15, PIK3CD-AS2, POU3F1, PPP1R14B, PTPRJ, RASGRF1, RPL13, RPL35, RPL6, RPL7, RPS8, SFXN4, SGCE, SIAH2, SIGLEC14, SLC29A2, SMARCB1, SNHG11, SNHG17, SNHG7, SOX9, SPTBN2, ST8SIA4, SUGCT, TACC1, TERT, TLE4, UQCRH, WDFY1, or WNK2.

8. The method of claim 7 wherein determining the molecular subgroup of the aggressive B-cell lymphoma further comprises preparing a gene expression profile for one or more of the following genes in the biopsy: ASB13, AUH, BANK1, BATF3, BTG2, CARD11, CCDC50, CCL17, CREB3L2, CYB5R2, DNAJB12, FAM159A, FSCN1, GIT2, GSK3B, HOMER2, IFIH1, IK, IL13RA1, IRF4, ISY1, ITPKB, LIMA1, LIMD1, MAL, MAML3, MME, MOBKL2C, MST1R, MYBL1, NECAP2, NFIL3, OPA1, PDCD1LG2, PHF23, PIM2, PRDX2, PRKCB, PRR6, PTGIR, QSOX1, R3HDM1, RAB7L1, RCL1, RHOF, S1PR2, SERPINA9, SLAMF1, SNX11, TFPI2, TMOD1, TNFRSF13 B, TRAF1, TRIM56, UBXN4, VRK3, WAC, or WDR55.

9. The method of claim 7 wherein determining the molecular subgroup of the aggressive B-cell lymphoma further comprises preparing a gene expression profile for one or more of the following genes in the biopsy: BCL2, FCGR2B or PVT1.

10. The method of claim 1 wherein the subject is a human.

11. The method of claim 1, wherein in determining that the molecular subgroup is DHITsig-pos, it is further determined that:
one or more of the following genes is overexpressed in the biopsy: FAM216A, UQCRH, SUGCT, SNHG7, LINC00957, PIK3CD-AS2, RPL6, EI F4EBP3, FHIT, SLC29A2, TERT, SMARCB1, SNHG17, SPTBN2, ATF4, RPL35, HAGHL, CTD-3074O7.5, WNK2, CCDC78, RPL13, RPL7, SFXN4, SGCE, LRRC75A-AS1, HRK, DANCR, RPS8, SNHG11, NMRAL1, PPP1R14B, MACROD1, or SOX9; and
one or more of the following genes is underexpressed in the biopsy: MYEOV, IL10RA, TLE4, PARP15, CCL17, HMSD, DOCK10, MVP, ASS1P1, GNG2, ETV5, RASGRF1, ACPP, COBLL1, ARPC2, CFLAR, AC104699.1, GALNT6, ARHGAP25, SIGLEC14, PTPRJ, CR2, CAB39, HIVEP1, ADTRP, POU3F1, MREG, TACC1, ST8SIA4, WDFY1, ARID3B, CCL22, SIAH2, CPEB4, ANKRD33B, NCOA1, BCL2A1, DGKG, ALS2, LTA, or FCRL5.

12. The method of claim 2 wherein determining molecular subgroup of the aggressive B-cell lymphoma further comprises preparing a gene expression profile for one or more of the following genes in the biopsy: AC104699.1, ACPP, ADTRP, ALS2, ANKRD33B, ARHGAP25, ARID3B, ARPC2, ASS1P1, ATF4, BCL2A1, CAB39, CCDC78, CCL17, CCL22, CFLAR, COBLL1, CPEB4, CR2, CTD-3074O7.5, DANCR, DGKG, DOCK10, EI F4EBP3, ETV5, FAM216A, FCRL5, FHIT, GALNT6, GNG2, HAGHL, HIVEP1, HMSD, HRK, IL10RA, LINC00957, LRRC75A-AS1, LTA, MACROD1, MREG, MVP, MYEOV, NCOA1, NMRAL1, PARP15, PIK3CD-AS2, POU3F1, PPP1R14B, PTPRJ, RASGRF1, RPL13, RPL35, RPL6, RPL7, RPS8, SFXN4, SGCE, SIAH2, SIGLEC14, SLC29A2, SMARCB1, SNHG11, SNHG17, SNHG7, SOX9, SPTBN2, ST8SIA4, SUGCT, TACC1, TERT, TLE4, UQCRH, WDFY1, or WNK2.

13. The method of claim 12, wherein determining the molecular subgroup of the aggressive B-cell lymphoma further comprises preparing a gene expression profile for one or more of the following genes in the biopsy: ASB13, AUH, BANK1, BATF3, BTG2, CARD11, CCDC50, CCL17, CREB3L2, CYB5R2, DNAJB12, FAM159A, FSCN1, GIT2, GSK3B, HOMER2, IFIH1, IK, IL13RA1, IRF4, ISY1, ITPKB, LIMA1, LIMD1, MAL, MAML3, MME, MOBKL2C, MST1R, MYBL1, NECAP2, NFIL3, OPA1, PDCD1LG2, PHF23, PIM2, PRDX2, PRKCB, PRR6, PTGIR, QSOX1, R3HDM1, RAB7L1, RCL1, RHOF, S1PR2, SERPINA9, SLAMF1, SNX11, TFPI2, TMOD1, TNFRSF13 B, TRAF1, TRIM56, UBXN4, VRK3, WAC, or WDR55.

14. The method of claim 13 wherein determining the molecular subgroup of the aggressive B-cell lymphoma further comprises preparing a gene expression profile for one or more of the following genes in the biopsy: BCL2, FCGR2B or PVT1.

15. The method of claim 2, wherein in evaluating whether the molecular subgroup is DHITsig-neg, it is further determined whether:
one or more of the following genes is underexpressed in the biopsy: FAM216A, UQCRH, SUGCT, SNHG7, LINC00957, PIK3CD-AS2, RPL6, EI F4EBP3, FHIT, SLC29A2, TERT, SMARCB1, SNHG17, SPTBN2, ATF4, RPL35, HAGHL, CTD-3074O7.5, WNK2, CCDC78, RPL13, RPL7, SFXN4, SGCE, LRRC75A-AS1, HRK, DANCR, RPS8, SNHG11, NMRAL1, PPP1R14B, MACROD1, or SOX9; and
one or more of the following genes is overexpressed in the biopsy: MYEOV, IL10RA, TLE4, PARP15, CCL17, HMSD, DOCK10, MVP, ASS1P1, GNG2, ETV5, RASGRF1, ACPP, COBLL1, ARPC2, CFLAR, AC104699.1, GALNT6, ARHGAP25, SIGLEC14, PTPRJ, CR2, CAB39, HIVEP1, ADTRP, POU3F1, MREG, TACC1, ST8SIA4, WDFY1, ARID3B, CCL22, SIAH2, CPEB4, ANKRD33B, NCOA1, BCL2A1, DGKG, ALS2, LTA, or FCRL5.

16. The method of claim 2 wherein the subject is a human.

17. A method for determining a prognosis for a subject with an aggressive B-cell lymphoma comprising:
determining the molecular subgroup of the aggressive B-cell lymphoma by preparing a gene expression profile from a biopsy obtained from the subject, the gene expression profile covering all of the following genes: AFMID, ALOX5, BATF, CD24, CD80, CDK5R1, EBI3, GAMT, GPR137B, IL21R, IRF4, JCHAIN, LY75, MIR155HG, MYC, OR13A1, PEG10, QRSL1, RFFL, RGCC, SEMA7A, SGPP2, SLC25A27, SMIM14, SNHG19, STAT3, SYBU, TNFSF8, VASP, and VOPP1;

wherein the molecular subgroup is a positive double hit signature (DHITsig-pos) if:
collectively OR13A1, MYC, SLC25A27, ALOX5, TNFSF8, PEG10, GAMT, SNHG19, QRSL1, RGCC, JCHAIN, CD24, AFMID, SMIM14, and SYBU are overexpressed in the biopsy; and
collectively GPR137B, CDK5R1, LY75, VASP, RFFL, MIR155HG, VOPP1, BATF, STAT3, IRF4, SGPP2, CD80, SEMA7A, EBI3, and IL21R are underexpressed in the biopsy;
and wherein the molecular subgroup is a negative double hit signature (DHITsig-neg) if:
collectively OR13A1, MYC, SLC25A27, ALOX5, TNFSF8, PEG10, GAMT, SNHG19, QRSL1, RGCC, JCHAIN, CD24, AFMID, SMIM14, and SYBU are underexpressed in the biopsy; and
collectively GPR137B, CDK5R1, LY75, VASP, RFFL, MIR155HG, VOPP1, BATF, STAT3, IRF4, SGPP2, CD80, SEMA7A, EBI3, and IL21R are overexpressed in the biopsy;
wherein preparing the gene expression profile comprises using a plurality of DNA probes, a plurality of subsets of the plurality of probes having a nucleic acid sequence of a corresponding one of each of SEQ ID NO:1 through SEQ ID NO:30;
wherein a DHITsig-pos molecular subgroup is predictive of a poor prognosis and a DHITsig-neg molecular subgroup is predictive of a good prognosis.

* * * * *